US011246905B2

(12) United States Patent
Gibbs et al.

(10) Patent No.: US 11,246,905 B2
(45) Date of Patent: Feb. 15, 2022

(54) **TREATING INFECTIONS USING IDSD FROM *PROTEUS MIRABILIS***

(71) Applicant: President and Fellows of Harvard College, Cambridge, MA (US)

(72) Inventors: Karine Gibbs, Brookline, MA (US); Christina Caroline Saak, San Diego, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 46 days.

(21) Appl. No.: 16/325,629

(22) PCT Filed: Aug. 14, 2017

(86) PCT No.: PCT/US2017/046763
§ 371 (c)(1),
(2) Date: Feb. 14, 2019

(87) PCT Pub. No.: WO2018/035046
PCT Pub. Date: Feb. 22, 2018

(65) Prior Publication Data
US 2019/0201479 A1 Jul. 4, 2019

Related U.S. Application Data

(60) Provisional application No. 62/375,248, filed on Aug. 15, 2016.

(51) Int. Cl.

| | |
|---|---|
| ***A61K 38/16*** | (2006.01) |
| ***A61K 35/74*** | (2015.01) |
| ***A61P 31/04*** | (2006.01) |
| ***A01N 63/50*** | (2020.01) |
| ***C12N 1/20*** | (2006.01) |
| ***A61K 38/00*** | (2006.01) |

(52) U.S. Cl.
CPC .............. *A61K 38/16* (2013.01); *A01N 63/50* (2020.01); *A61K 35/74* (2013.01); *A61P 31/04* (2018.01); *C12N 1/20* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 1,722,030 | A | 7/1929 | Belknap |
| 2,045,388 | A | 6/1936 | Guthrie |
| 2,068,655 | A | 1/1937 | Henri et al. |
| 2,091,133 | A | 8/1937 | Robert |
| 2,167,478 | A | 7/1939 | Good |
| 2,176,932 | A | 10/1939 | Clyde |
| 2,193,673 | A | 3/1940 | Emery et al. |
| 2,248,403 | A | 7/1941 | Elliott |
| 2,248,566 | A | 7/1941 | Busch |
| 2,251,908 | A | 8/1941 | Howard |
| 2,339,550 | A | 1/1944 | Bosomworth |
| 2,369,853 | A | 2/1945 | Purtell |
| 2,377,738 | A | 6/1945 | Wineland |
| 2,400,574 | A | 5/1946 | Rea et al. |
| 2,426,080 | A | 8/1947 | James et al. |
| 2,617,493 | A | 11/1952 | Jones |
| 2,627,830 | A | 2/1953 | Herman |
| 2,652,590 | A | 9/1953 | Robert et al. |
| 2,742,108 | A | 4/1956 | Schnabel et al. |
| 2,758,683 | A | 8/1956 | Randol |
| 2,849,949 | A | 9/1958 | Eugene |
| 2,917,502 | A | 2/1959 | Robert et al. |
| 3,058,755 | A | 10/1962 | Baron |
| 3,078,271 | A | 2/1963 | De et al. |
| 3,130,273 | A | 4/1964 | Noecker |
| 3,286,344 | A | 11/1966 | Brainard et al. |
| 3,322,632 | A | 5/1967 | Gerhard et al. |
| 3,483,363 | A | 12/1969 | Ross |
| 4,526,988 | A | 7/1985 | Hertel |
| 4,561,103 | A | 12/1985 | Horiguchi et al. |
| 4,680,299 | A | 7/1987 | Hesson |
| 5,300,671 | A | 4/1994 | Tognella et al. |
| 5,368,853 | A | 11/1994 | Hooks et al. |
| 5,512,658 | A | 4/1996 | Pastan et al. |
| 5,602,689 | A | 2/1997 | Kadlec et al. |
| 5,754,153 | A | 5/1998 | Mizutome et al. |
| 6,110,930 | A | 8/2000 | Taniguchi et al. |
| 6,288,613 | B1 | 9/2001 | Bennett |
| 6,590,153 | B1 | 7/2003 | Kohan |

(Continued)

FOREIGN PATENT DOCUMENTS

| | | | |
|---|---|---|---|
| EP | 0273166 | A1 | 7/1988 |
| GB | 321832 | A | 11/1929 |

(Continued)

OTHER PUBLICATIONS

GenBank CP004022 Jan. 30, 2014 submission version—PDF print-out downloaded Jan. 16, 2021.*
Pearson, M.M. et al., "Complete Genome Sequence of Uropathogenic Proteus mirabilis, a Master of both Adherence and Motility", Journal of Bacteriology, 190(11): 4027-4037 (Jun. 2008) (Year: 2008).*
Gibbs, K.A. et al., "Genetic Determinants of Self Identity and Social Recognition in Bacteria", Science vol. 321 (5886): 256-259 (Jul. 2008) (Year: 2008).*
16325629_SEQIDNO_3_alignment.txt file (Year: 2021).*
US-16-325-629-4_pep_vs_US 10-603-114B_pep_align.txt (Year: 2021).*
US-16-325-629-12_pep_vs_US 10-603-114B_pep_align.txt (Year: 2021).*

(Continued)

*Primary Examiner* — Anand U Desai
(74) *Attorney, Agent, or Firm* — Wolf, Greenfield & Sacks, P.C.

(57) ABSTRACT

The present disclosure provides, in some embodiments, compositions, kits, systems, and methods for reducing bacteria on a surface (e.g., a medical device) and preventing and/or treating a bacterial infection (e.g., urinary tract infection) in a subject using IdsD protein or a fragment thereof.

26 Claims, 8 Drawing Sheets

Specification includes a Sequence Listing.

(56) References Cited

U.S. PATENT DOCUMENTS

| | | | | |
|---|---|---|---|---|
| 6,605,709 | B1 * | 8/2003 | Breton | C07K 14/24 435/320.1 |
| 7,359,517 | B1 | 4/2008 | Rowe | |
| 2001/0014455 | A1 | 8/2001 | Prusiner et al. | |
| 2002/0036488 | A1 | 3/2002 | Ueda | |
| 2002/0038206 | A1 | 3/2002 | Dori | |
| 2003/0030075 | A1 | 2/2003 | Yamaguchi et al. | |
| 2004/0009187 | A1 | 1/2004 | Choi et al. | |
| 2004/0053348 | A1 | 3/2004 | Faris et al. | |
| 2004/0214212 | A1 | 10/2004 | Raitano et al. | |
| 2005/0002210 | A1 | 1/2005 | Moon et al. | |
| 2005/0027875 | A1 | 2/2005 | Deng | |
| 2006/0062784 | A1 | 3/2006 | Grant et al. | |
| 2006/0139251 | A1 | 6/2006 | Morosawa et al. | |
| 2007/0209263 | A1 | 9/2007 | Hohlbein et al. | |
| 2008/0035333 | A1 | 2/2008 | Newman | |
| 2008/0082935 | A1 | 4/2008 | Relyea et al. | |
| 2008/0125385 | A1 | 5/2008 | Hajjar et al. | |
| 2008/0242720 | A1 | 10/2008 | Mangel | |
| 2009/0042769 | A1 | 2/2009 | MacLean | |
| 2009/0055417 | A1 | 2/2009 | Hannuksela | |
| 2009/0119594 | A1 | 5/2009 | Hannuksela | |
| 2009/0215764 | A1 | 8/2009 | Das | |
| 2009/0287493 | A1 | 11/2009 | Janssen et al. | |
| 2010/0093273 | A1 | 4/2010 | Hohl | |
| 2011/0028386 | A1 | 2/2011 | Hodges et al. | |
| 2011/0030908 | A1 | 2/2011 | Sealey et al. | |
| 2011/0062030 | A1 | 3/2011 | Lippert et al. | |
| 2011/0237522 | A1 | 9/2011 | Khvorova et al. | |
| 2012/0001587 | A1 | 1/2012 | Kono et al. | |
| 2012/0237498 | A1 | 9/2012 | Ahrens et al. | |
| 2012/0271610 | A1 | 10/2012 | Phillips et al. | |
| 2013/0332133 | A1 | 12/2013 | Horn et al. | |
| 2013/0338295 | A1 | 12/2013 | Moore et al. | |
| 2014/0050725 | A1 | 2/2014 | Jenkins et al. | |
| 2014/0113950 | A1 | 4/2014 | Khvorova et al. | |
| 2014/0294968 | A1 | 10/2014 | Hofmann et al. | |
| 2014/0358415 | A1 | 12/2014 | McDonald et al. | |
| 2014/0376274 | A1 | 12/2014 | Hosotani et al. | |
| 2015/0255620 | A1 | 9/2015 | Nelson et al. | |
| 2015/0255624 | A1 | 9/2015 | Nelson et al. | |
| 2016/0158179 | A1 | 6/2016 | Baker et al. | |
| 2016/0355798 | A1 | 12/2016 | Lanes et al. | |

FOREIGN PATENT DOCUMENTS

| | | | | |
|---|---|---|---|---|
| GB | 580851 | A | 11/1929 | |
| GB | 375381 | A | 6/1932 | |
| GB | 571698 | A | 9/1945 | |
| IN | 02729MU2012 | A | 9/2012 | |
| WO | WO 9316073 | A1 | 8/1993 | |
| WO | WO 2012/168570 | A1 | 12/2013 | |
| WO | WO 2015/048348 | A4 | 4/2015 | |
| WO | WO-2017178558 | A1 * | 10/2017 | G16B 20/00 |
| WO | WO 2018/035046 | A1 | 2/2018 | |
| WO | WO 2019/036719 | A2 | 2/2019 | |
| ZA | 93958 | B | 8/1994 | |

OTHER PUBLICATIONS

US-16-325-629-10_pep_vs_US 10-603-114B_pep_align.txt (Year: 2021).*

GIBBS_IDSD_SEQIDNO9_alginment_nucleic_acid.txt (Year: 2021).*

US-16-325-629-10_pep_vs_SCIENCE_GIBBS_IDSD-pep_align.txt (Year: 2021).*

Science_Gibbs_IDSD_US-16-325-629-2_pep_vs_ACF41953_1_pep_align.txt (Year: 2021).*

Invitation to Pay Additional Fees for Application No. PCT/US17/46763 dated Oct. 11, 2017.

International Search Report and Written Opinion for Application No. PCT/US17/46763 dated Dec. 15, 2017.

International Preliminary Report on Patentability for Application No. PCT/US17/46763 dated Feb. 28, 2019.

[No Author Listed] UniProtKB—B4F004 (B4F004_PROMI), Proteus mirabilis (strain HI4320), Putative membrane protein. Sep. 23, 2008. Retrieved from ://www.uniprot.org/uniprot/B4F004. Entire document. 4 pages.

[No Author Listed] UniProtKB—B4YPP4 (B4YPP4_PROMI), Proteus mirabilis, IdsD, Sep. 23, 2008. Retrieved from /www.uniprot.org/uniprot/B4YPP4. 2 pages.

Alteri et al., Multicellular Bacteria Deploy the Type VI Secretion System to Preemptively Strike Neighboring Cells. PLOS Pathogens. Sep. 2013;9(9):e1003608. 18 pages.

Armbruster et al., Genome-wide transposon mutagenesis of Proteus mirabilis: Essential genes, fitness factors for catheter-associated urinary tract infection, and the impact of polymicrobial infection on fitness requirements. PLOS Pathogens. Jun. 2017:43 pages.

Budding et al., The Dienes phenomenon: competition and territoriality in Swarming Proteus mirabilis. J Bacteriol. Jun. 2009;191(12):3892-900.

Carderelli et al., Two Proteins Form a Heteromeric Bacterial Self-Recognition Complex in Which Variable Subdomains Determine Allele-Restricted Binding. MBio. Jun. 9, 2015;6(3):e00251. 8 pages.

Colling et al., Hypersensitivity of *Arabidopsis* TAXIMIN1 overexpression lines to light stress is correlated with decreased sinapoyl malate abundance and countered by the antibiotic cefotaxime. Plant Signaling & Behavior. 2016;11(4):e1143998. 4 pages. Epub Mar. 11, 2016.

Feder et al., Identification of a new family of putative PD-(D/E)XK nucleases with unusual phylogenomic distribution and a new type of the active site. BMC Genomics. Feb. 2005;6:21. 13 pages.

Gibbs et al., Genetic determinants of self identity and social recognition in bacteria. Science. Jul. 11, 2008;321(5886):256-9.

Gibbs et al., Identity Gene Expression in *Proteus mirabilis*. Journal of Bacteriology. Jul. 2011;193(13):3286-92.

Gibson et al., Dendrite self-avoidance requires cell-autonomous slit/robo signaling in cerebellar purkinje cells. Neuron. Mar. 2014;81(5):1040-56.

Jackson et al., Evolutionary diversification of an ancient gene family (rhs) through C-terminal displacement. BMC Genomics. Dec. 2009;10:584. 16 pages.

Kosinski et al., The PD-(D/E)XK superfamily revisited: identification of new members among proteins involved in DNA metabolism and functional predictions for domains of (hitherto) unknown function. BMC Bioinformatics. Jul. 2005;6:172. 13 pages.

Koskiniemi et al., Rhs proteins from diverse bacteria mediate intercellular competition. PNAS. Apr. 2013;110(17):7032-7.

Luu et al., PAPC mediates self/non-self-distinction during Snail1-dependent tissue separation. J Cell Biol. Mar. 2015;208(6):839-56.

Mudvari et al., SNPlice: variants that modulate Intron retention from RNA-sequencing data. Bioinformatics. Apr. 2015;31(8):1191-8.

Pearson et al., Complete genome sequence of uropathogenic Proteus mirabilis, a master of both adherence and motility. J Bacteriol. Jun. 2008;190(11):4027-37.

Saak et al., The Self-Identity Protein IdsD Is Communicated between Cells in Swarming *Proteus mirabilis* Colonies. Journal of Bacteriology. Dec. 2016;198(24):3278-86.

Septer et al., Genomic instability contributes to self-recognition behavior in Proteus mirabilis. American Society for Microbiology 2014 National Meeting (ASM 2014). Boston, MA. May 2014:23 slides.

Shao et al., Rapid microfluidic perfusion enabling kinetic studies of lipid ion channels in a bilayer lipid membrane chip. Ann Biomed Eng. Aug. 2011;39(8):2242-51.

Steczkiewicz et al., Sequence, structure and functional diversity of PD-(D/E)XK phosphodiesterase superfamily. Nucleic Acids Research. Aug. 2012;40(15):7016-45.

Sullivan et al., The Complete Genome Sequence of Proteus mirabilis Strain BB2000 Reveals Differences from the P. mirabilis Reference Strain. Genome Announc. Sep. 2013;1(5):e00024-13. 2 pages.

Tipping et al., Peer pressure from a Proteus mirabilis self-recognition system controls participation in cooperative swarm motility. bioRxiv. Dec. 2018:12 pages.

(56) References Cited

OTHER PUBLICATIONS

Wenren et al., Two Independent Pathways for Self-Recognition in *Proteus mirabilis* Are Linked by Type VI-Dependent Export. mBio. Jul./Aug. 2013;4(4):10 pages.
Whitney et al., Genetically distinct pathways guide effector export through the type VI secretion system. Mol Microbiol. May 2014;92(3):529-42.
Zepeda-Rivera et al., A Proposed Chaperone of the Bacterial Type VI Secretion System Functions To Constrain a Self-Identity Protein. Journal of Bacteriology. Jul. 2018;200(14):e00688-17. 16 pages.
International Search Report for Application No. PCT/US2020/031686, dated Aug. 24, 2020.
Bujnicki et al., Identification of a PD-(D/E)XK-like domain with a novel configuration of the endonuclease active site in the methyl-directed restriction enzyme Mrr and its homologs. Gene. Mar. 2001;267(2):183-91.
Claret et al., Functions of the subunits in the FlhD(2)C(2) transcriptional master regulator of bacterial flagellum biogenesis and swarming. J Mol Biol. Nov. 2000;303(4):467-78.
Colonnello et al., Oxytocin sharpens self-other perceptual boundary. Psychoneuroendocrinology. Dec. 2013;38(12):2996-3002.
Delucia et al., Visual memory for moving scenes. Q J Psychol. Feb. 2006;59(2):340-60.
Dienes, Reproductive processes in Proteus cultures. Proc Soc Exp Biol Med. Nov. 1946;63(2):265-70.
Fusseis et al., Creep cavitation can establish a dynamic granular fluid pump in ductile shear zones. Nature. Jun. 2009;459(7249):974-7.
Léveillé et al., Running as fast as it can: how spiking dynamics form object groupings in the laminar circuits of visual cortex. J Comput Neurosci. Apr. 2010;28(2):323-46.
Lin et al., A repetitive DNA sequence, rhs, responsible for duplications within the *Escherichia coli* K-12 chromosome. J Mol Biol. Jul. 1984;177(1):18 pages.
Saak et al., A single point mutation in a TssB/VipA homolog disrupts sheath formation in the type VI secretion system of Proteus mirabilis. PLoS One. Sep. 26, 2017;12(9):e0184797. doi: 10.1371/journal.pone.0184797. eCollection 2017.
Weise et al., Visualizing association of lipidated signaling proteins in heterogeneous membranes—partitioning into subdomains, lipid sorting, interfacial adsorption, and protein association. Biochim Biophys Acta. Jul. 2010;1798(7):1409-17.

* cited by examiner

TREATING INFECTIONS USING IDSD FROM *PROTEUS MIRABILIS*

RELATED APPLICATIONS

This application is a national stage filing under 35 U.S.C. § 371 of international PCT application, PCT/US2017/046763, filed Aug. 14, 2017, which claims priority under 35 U.S.C § 119(e) to U.S. provisional application, U.S. Ser. No. 62/375,248, filed Aug. 15, 2016, each of which is-incorporated herein by reference.

BACKGROUND OF THE INVENTION

Initial colonization of hosts by many species of bacteria is conferred, in part, by their ability to swarm. Swarming is a type of bacterial motility in which colonies of bacteria expand outward on a surface at centimeter-scale distances. In some species, bacterial colonies of identical populations will merge while colonies of genetically distinct populations will remain separate forming a visually apparent boundary. A boundary formed between genetically distinct populations requires that the bacteria have the ability to discriminate between self and non-self.

*Proteus mirabilis* is a swarming gram-negative bacterium and causative agent of urinary tract infections. Boundary formation between genetically distinct populations of the swarming bacterium *P. mirabilis* requires, in at least one strain, three gene clusters termed idr, tss, and ids. The idr and tss genes, which encode putative cytotoxic elements and type VI secretion (T6S) system, respectively, are needed for competition with other *P. mirabilis* strains and appear to evoke contact-dependent growth inhibition. The ids genes encode proteins necessary for self-recognition including IdsD protein that is exported by one cell and received by another cell. When IdsD from a donor cell (e.g., IdsD from *P. mirabilis* strain BB2000) interacts with IdsE in the recipient cell (e.g., IdsE from *P. mirabilis* strain BB20000), *P. mirabilis* populations are recognized as self (kin) and merge. When IdsD from a donor cell (e.g., IdsD from *P. mirabilis* strain BB2000) remains unbound to IdsE in the recipient cell (e.g., IdsE from *P. mirabilis* strain HI4320), *P. mirabilis* populations are recognized as non-self and form a boundary. Unbound IdsD in the recipient cell is non-lethal. Thus, IdsD and IdsE form a heteromeric bacterial self-recognition system.

SUMMARY OF THE INVENTION

Provided herein are compositions, kits, systems, and methods for reducing bacterial growth and/or swarming (e.g., on a surface) and for treating a subject having a bacterial infection (e.g., a urinary tract infection) using IdsD protein or a fragment thereof.

Bacteria, such as the swarming bacterium *P. mirabilis*, can come together in colonies that move rapidly across surfaces. During this swarm migration, *P. mirabilis* exhibits self versus non-self recognition. Populations of genetically identical organisms merge while populations of genetically different organisms separate and form a visible boundary (1-4). The ids operon, encoding six proteins IdsA to IdsF, is one of the genetic loci responsible for boundary formation (2, 5, 6). Three Ids proteins (IdsA, IdsB, and IdsD) are exported in a Type VI Secretion System (T6SS) (5, 7). T6SSs, which are widely distributed among gram-negative bacteria, are machines that can translocate proteins, primarily lethal proteins, from the inside of one cell directly into another (8-28). T6SSs have been shown to transfer lethal proteins to recipient cells, however, recipient cells many remain viable if they have an inhibitory protein that binds to and inhibits the transferred lethal protein (15, 16, 18, 21, 22, 28-30).

The present disclosure provides that IdsD protein is transferred from one cell to another in a T6SS-dependent manner where IdsD and IdsE proteins function as a bacterial self-recognition system that determines bacterial behaviors (e.g., expansion of a swarming colony) within the recipient cell. IdsD and IdsE proteins each contain a variable region, predicted to be a transmembrane region, that has a stretch of amino acids that is generally unique among strains (2, 31). IdsD and IdsE bind in vitro when the variable regions of both proteins originate from the same strain. Binding pairs of IdsD and IdsE are termed cognate (31). By contrast, when the variable regions of IdsD and IdsE do not originate from the same strain, these proteins do not bind in vitro, and the IdsD-IdsE pair is thus termed non-cognate (31).

Swarming populations of strains producing cognate IdsD-IdsE pairs merge and thus recognize each other as self; however, swarming populations of strains producing non-cognate IdsD-IdsE pairs form a visible boundary and are considered non-self (31). Without being bound by theory, the present disclosure provides that IdsD from a donor cell likely interacts with IdsE in a recipient cell, thereby merging swarming populations of donor and recipient cells. Lack of IdsD and IdsE interaction in recipient cells negatively impacts swarm colony expansion, but not viability.

The present disclosure provides compositions, kits, systems, and methods for reducing bacteria on a surface (e.g., a medical device) and preventing and/or treating a bacterial infection (e.g., urinary tract infection) in a subject using IdsD protein or a fragment thereof.

In some embodiments, the IdsD protein comprises an amino acid sequence as provided by SEQ ID NO:2 or SEQ ID NO:4, or a fragment thereof, wherein the IdsD protein comprises a variable region that is at least 70%, at least 75%, at least 80%, at least 85%, at least 90%, at least 92%, at least 95%, at least 96%, at least 97%, at least 98%, at least 99%, or at least 99.5% identical to the amino acid sequence of IdsD protein as provided by SEQ ID NO:10 or SEQ ID NO:12, and wherein the amino acid sequence of the IdsD protein is not identical to the amino acid sequence of a naturally occurring *Proteus mirabilis* IdsD protein.

In some embodiments, the IdsD protein fragment comprises the variable region. In some embodiments, the variable region comprises an amino acid sequence as provided by SEQ ID NO:10 or SEQ ID NO:12. In some embodiments, the variable region comprises one or more mutations. In some embodiments, the one or more mutations are mutations to amino acid residues 761 and/or 765 of amino acid sequences provided by SEQ ID NO:2 or SEQ ID NO:4 or the one or more mutations are mutations to amino acid residues 1 and/or 5 of amino acid sequences provided by SEQ ID NO:10 or SEQ ID NO:12.

In some embodiments, the IdsD protein or fragment thereof is provided by nucleic acids encoding the IdsD protein or fragment thereof. In some embodiments, the nucleic acids encoding the IdsD protein or fragment thereof are provided by SEQ ID NO:1 or SEQ ID NO:3. In some embodiments, the nucleic acids encoding the IdsD protein or fragment thereof are provided by SEQ ID NO:9 or SEQ ID NO:11.

In some embodiments, the IdsD protein is provided by a bacterial composition comprising the IdsD protein. In some embodiments, the bacterial composition comprises *Proteus mirabilis*.

In some embodiments, the IdsD protein is provided by a pharmaceutical composition comprising the IdsD protein and a pharmaceutically acceptable carrier. In some embodiments, the IdsD protein further comprises one or more therapeutic agents. In some embodiments, the therapeutic agent is an antibiotic.

In some embodiments, the disclosure provides a method of reducing bacterial growth and/or swarming on a surface comprising contacting or coating the surface with IdsD protein. In some embodiments, contacting or coating comprises spraying, brushing, applying, and/or treating the surface with IdsD protein.

In some embodiments, the disclosure provides a method for reducing the occurrence of urinary tract infections in a subject with a medical device comprising coating of a medical device with IdsD protein and implanting the device in a subject. In some embodiments, the medical device is a catheter, sphincter, dilator, stent, tissue bonding device, graft, drain tube, shunt, joint replacement, pacemaker system, valve, or prosthesis. In some embodiments, the subject is a human.

In some embodiments, the disclosure provides a method for treating or preventing a bacterial infection, the method comprising administering to a subject in need thereof a therapeutically effective amount of IdsD protein. In some embodiments, the bacterial infection is a urinary tract infection. In some embodiments, the urinary tract infection is a catheter-associated urinary tract infection. In some embodiments, the bacterial infection is a *Proteus mirabilis* infection. In some embodiments, the method further comprises screening the *Proteus mirabilis* infection for IdsD and/or IdsE. In some embodiments, screening the *Proteus mirabilis* infection for IdsD and/or IdsE comprises sequencing assays, binding assays, and/or boundary formation assays. In some embodiments, the method further comprises administering one or more other therapeutic agents. In some embodiments, the other therapeutic agent is an antibiotic. In some embodiments, the subject is human.

In some embodiments, the disclosure provides a medical device kit comprising a medical device and IdsD protein. In some embodiments, the medical device is a catheter, sphincter, dilator, stent, tissue bonding device, graft, drain tube, shunt, joint replacement, pacemaker system, valve, or prosthesis.

These and other aspects and embodiments of the invention will be described in greater detail herein. The description of exemplary embodiments of IdsD protein is provided for illustration purposes only and not meant to be limiting. Additional compositions, kits, systems, and methods (e.g., variations of IdsD protein described in detail above) are also embraced by this disclosure.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

FIG. 1A shows a plot of colony expansion of monoclonal *P. mirabilis* swarms after 16 hours on swarm-permissive agar surfaces. Variable region (VR) identities of the produced IdsD and IdsE variants are indicated for each strain. Widths of individual swarm rings within a swarm colony are marked by different shades. N=16, error bars show standard deviations of individual swarm ring widths.

FIG. 1B shows representative pictures of each strain from FIG. 1A that were taken 24 hours after inoculation.

FIG. 1C shows a plot of viable cells per monoclonal swarm colony after 16 hours on swarm-permissive agar surfaces. Strain descriptions are found in FIG. 1D. N=12.

FIG. 1D shows a plot of diameters of monoclonal colonies in 0.3% LB medium after 9 hours. N=6.

FIG. 2A shows representative pictures of swarm colony expansion and competing mechanistic models for the mode of IdsD-IdsE interactions. FIG. 2A, left panel, shows a schematic depiction of intercellular, T6SS459 dependent (grey arrow) communication of IdsD from one cell (double-walled oval) to a neighboring cell. Binding to IdsE in the recipient cell allows for colony expansion to proceed, while lack thereof impairs colony expansion. This communication is bidirectional if both cells have a functional T6SS. FIG. 2A, right panel, shows a schematic depiction of swarm colony expansion depending on the binding states of the IdsD and IdsE variants produced within an individual cell.

FIG. 2B shows representative western blots of supernatants of strains carrying either the 464 empty vector pKG101 (6) or pLW101, which produces IdsA [T6SS_Hcp (PF05638)] with a C-terminal FLAG tag, were subjected to trichloroacetic acid precipitations. Whole cell extracts were obtained as well. All samples were analyzed using Western blot analysis. The BB2000-derived vipA::Tn5 strain contains a chromosomal transposon insertion in the gene encoding VipA [T6SS_VipA (PF05591)] (5), which is essential for export of T6SS-related factors and was used as a control. Blots were probed with antibodies against FLAG to detect IdsA-FLAG and against $\sigma^{70}$, a bacterial protein transcription initiation factor used as a cell lysis control.

FIG. 2C shows representative pictures of swarm-permissive agar surfaces inoculated with Aids-derived (export-active, donor) strains on the left side and CCS05-derived (export-inactive, recipient) strains on the right side. Each strain produces the indicated IdsD and IdsE variants. Variable region exchanges from BB2000 (BB) to HI4320 (HI) are indicated with the prefix "VR". $D_{HI}$ and $E_{HI}$ are IdsD and IdsE variants derived completely from HI4320. Black outlines are shows combinations of swarms that merged. Arrowheads indicate where opposing swarm colonies intersect.

FIG. 3A shows a plot of colony expansion as described in FIG. 1A. Strains were inoculated either as monoswarms (export-active donor CCS06 or export-inactive recipient CCS05-derivatives) or as coswarms (CCS06 and CCS05-derivatives) at a 1:1 ratio. IdsD and IdsE variants produced by strains derived from CCS05 are indicated. CCS06 lacks IdsE, but produces $D_{VR\text{-}BB}$. Error bars, standard deviations for each swarm ring width (N=3 for monoswarms and coswarms of $D_{VR\text{-}BB}E_{VR\text{-}HI}$ and $D_{VR\text{-}HI}E_{VR\text{-}HI}$, n=6 for all others). Fold changes of total colony expansion between monoswarms and coswarms are indicated. *marks a significant change ($p<0.005$, two-tailed t test). na, not applicable.

FIG. 3B shows representative pictures of monoswarms and coswarms taken 24 hours after inoculation. Insets show models of intercellular, T6SS-dependent (grey arrow) communication of $D_{VR\text{-}BB}$ from an export-active cell (CCS06, grey) to its neighboring cell, whether export-active (grey) or export inactive (CCS05-derivative, white).

FIG. 5A shows a plot of viable cells per swarm colony over time on swarm-permissive agar surfaces. IdsD and IdsE variants produced by the different strains are indicated in FIG. 4B. N=4, error bars show standard deviations. Viability on surfaces are unaltered when IdsD and IdsE are noncognate.

FIG. 5B shows a plot of generation times during logarithmic growth in liquid medium. N=6. Boxes range from the $25^{th}$ to the $75^{th}$ percentile, lines within boxes indicate medians, and whiskers indicate minima and maxima.

DEFINITIONS

Figure 1A:
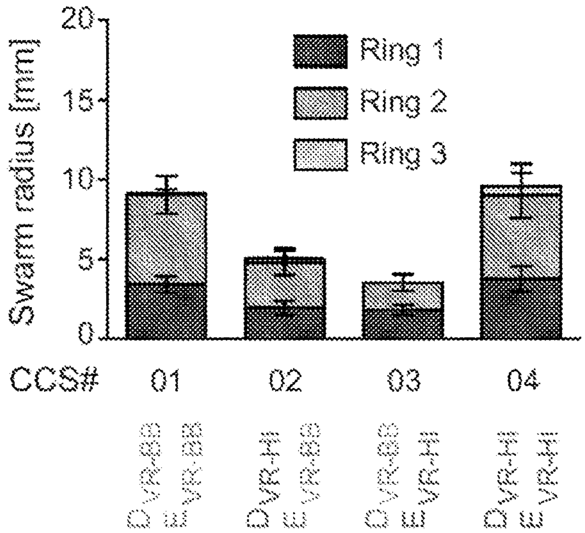
FIG. 1A-1D shows binding of IdsD (D) and IdsE (E) regulate *P. mirabilis* swarming.

The term "administer," "administering," or "administration" refers to implanting, absorbing, ingesting, injecting, inhaling, or otherwise introducing recombinant IdsD protein as described herein, or a composition thereof, in or on a subject.

Bacterial infections include, but are not limited to, gram-negative bacterial infections, gram-positive bacterial infections, and other bacterial infections. Exemplary bacterial infections include, but are not limited to, infections with a gram positive bacteria (e.g., of the phylum Actinobacteria, phylum Firmicutes, or phylum Tenericutes); gram negative bacteria (e.g., of the phylum Aquificae, phylum Deinococcus-*Thermus*, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

The term "boundary formation," as used herein refers to a macroscopically visible boundary of up to 3 mm formed when swarming populations of bacteria (e.g., *P. mirabilis*) meet and recognize each other as non-self. In contrast, swarming populations of bacteria (e.g., *P. mirabilis*) that meet and recognize each other as self merge to form a single larger swarm.

The term "coating", as used herein, refers to a layer of recombinant IdsD protein covering a surface. The coating can be applied to the surface or impregnated into the material of the surface. The coating may comprise any recombinant IdsD protein suitable for inhibiting the growth or motility of bacteria.

The term "cognate," as used herein, refers to IdsD and IdsE proteins that interact. Cognate IdsD-IdsE proteins may refer to recombinant proteins or proteins in *P. mirabilis.*

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "inhibition," as used herein, refers to inhibition of a pathogenic bacteria including the inhibition of any desired function or activity of the bacteria such as bacterial growth, colonization, or swarming. Inhibition of bacterial growth may include inhibition of the size of the pathogenic bacteria and/or inhibition of the proliferation or multiplication of the pathogenic bacteria. Inhibition of colonization of a pathogenic bacteria may include inhibition of the amount of bacteria and may be demonstrated by measuring the amount of the pathogenic bacteria before and after a treatment. Inhibition or inhibiting includes total and partial reduction of one or more activities of a pathogenic bacteria.

The term "medical device," as used herein, refers to any material, natural or artificial, that is inserted into a subject (e.g., mammal, such as a human). Examples of medical devices suitable for coating with *Proteus mirabilis* IsdD, as provided herein, include, but are not limited to, catheters such as urinary catheters, venous catheters, arterial catheters, dialysis catheters, peritoneal catheters, urinary sphincters, urinary dilators, urinary stents, tissue bonding urinary devices, vascular grafts, vascular dialtors, extravascular dilators, vascular stents, extravascular stents, wound drain tubes, shunts, pacemaker systems, joint replacements, heart valves, cardiac assist valves, bone prosthesis, joint prosthesis, or dental prosthesis.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* ($4^{th}$ ed., Cold Spring Harbor Laboratory Press, Cold Spring Harbor, N.Y. (2012)).

The term "non-cognate," as used herein, refers to IdsD and IdsE proteins that do not interact. Non-cognate IdsD-IdsE proteins may refer to recombinant proteins or proteins in *P. mirabilis.*

The term "non-pathogenic bacteria," as used herein, refers to any known or unknown non-pathogenic bacteria (gram positive or gram negative) and any pathogenic bacteria that has been mutated or converted to a non-pathogenic bacteria. Bacteria may be pathogenic to specific species and non-pathogenic to other species, and thus bacteria can be utilized in the species in which it is non-pathogenic.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "pathogenic bacteria," as used herein, refers to any bacteria or any other organism that is capable of causing or affecting a disease, disorder, or condition of a host organism.

The term "pharmaceutical compositions," as used herein, refer to any compositions prepared by any method known in the art of pharmacology. In general, such preparatory methods include bringing the "active ingredient," for example, recombinant IdsD protein as described herein, into association with a carrier or excipient, and/or one or more other accessory ingredients, and then, if necessary and/or desirable, shaping and/or packaging the product into a desired single- or multi-dose unit.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A protein may comprise different domains, for example, a variable domain (e.g., the variable domain in IdsD) and a T6S-associated motif. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* ($4^{th}$ ed., Cold Spring Harbor Laboratory Press, Cold Spring Harbor, N.Y. (2012)), the entire contents of which are incorporated herein by reference.

The term "*Proteus mirabilis* IdsD" and "D," as used herein, refers interchangeably to *Proteus mirabilis* IdsD. In some embodiments, *Proteus mirabilis* IdsD corresponds to IdsD from *Proteus mirabilis* strain BB2000 (NCBI Reference Sequence: EU635876.1:6035 . . . 9139, SEQ ID NO:1 (nucleotide) or SEQ ID NO:2 (amino acid)).

(SEQ ID NO: 1)

ATGACTGGAGAAGTGAATGAGAAATATTTAACACCGCAAGAGCGCAAAG
CGCGTCAGATGGTGAAGGCGGTAAACGAAGCGAGCCCACGAAACTTACC
GGCCGACGCGGTGGTATGCCCATGTGAAAATGAACATCGCCCTGTTTAT
CCGGTGCGTTATGCATATACCAACTTTTATTGTGATTTACATTTTTCTA
CAATTGAACAAGCACCAAATAAAACGTTAGAAGCGAGTATTCCTCCTTC
TATTAATCAATTATTGAATGCGAAAGATGTTACTGCTAGTAAAGGATTT
TCTGCAAGATTATTAAGACAAGGTTGGGTTTATGTTTTTGAAGAAGGCA
ATTACCCTACTAGAAGTAATTCTAGCAATAAAAGTTATCAAGAACAAAA
TGTTGATGCAACAAAAGGACGCCTATTAGTTTTTCAACATCAAGTGACA
ACCAGTGATGGCAATGAAAATTTCATTCCATATATATTTAAGCAATTAA
AAAATGGGGGTGTCACTTTAAAGAAAAACGGAAATAGTAATCCTTATTT
AGCTATACCGAAAGATGTGAAGGAAGCGACTATCTTATTCAGCGAAAGT
AAATTATCTGATTACACACTTAAAAAAATCATTTCATCTTCTAAGTTTA
GATCGAAATTAATGCAAAAAATCAATTTTATTGATTACAATAATAACGA
TTATTGTATTGAGCTAAATAAAGATAATTTAAATCGACTTGTTGAGGAT
TATAAAGAAGAAGTTGATAAATTTAAGCTATTTGTTAAAGAATTCACGC
ATTCAAATATACCCTCTTCTTTTTTTTCTGATACCACAAAAATACCCGA
CTTACCACAAGATGCAACTGTTTTGATTAATCAAGTAAATAGTGTTCTA
GATTATAATGAAAAAGCGACATTGCTTATTTTAAAAGATCCCGTAGGAT
ACCAAAAAGATATTTTATCTTATTATAATATTGTAACAAAATTACATTT
ATTATATCAGAACTATTATAGCCATCCGGATAAAATTGGCCAATTTATT
ACGAGTATACAAGAAGCTAGTCATCACATTAAAGATACTGATGAAAAAG
AAAAAATGCAAACAATACTAAAAGAGAGTATTAATCAGAATGCATTAGA
TAATGAGTGGAAAAATATTCATAAAACATTTATTTTTTTTGAGAAACAT
CAACGTATTGTATTATCATTGTATGAAAGCTTTATGAATAATCCGGCAA
TCATTAATGAAAACGGTGGCTTAAAACATTATTTTGATTATGCTTTTTC
ATATCACGAACGTATAACTAAAGAAGATGTCTTTAGTATTGATTTTTTT
AAGGACCTTAATCAAGCTTTTGATTTATATTTTGATTTAGTATCTCCAT
TAATGAATTCTATCGAAGGACAAAGAACATTAGATAAATTATATTCAAT
TAATGATGAAGAAAATAATAGCCTGTGGGTGGGAGTGACAAAGAAAGTA
ATTAGTCTTATTGCTAATTCAAAAATTAAGGACGCTCTTTTAAATGTAC
AAGAATATGCAATGCATATCGAAAATTTTGTTAATAAGCTTGCATTTAT
TTGCTCAGATAGCATTGGTTTCGCGTTTACAAAAACAAGTAAGGTACTT
TCTCATTACGATATTAAAAATAGACTAATTAATACTAAGGGTATTGACT
ATTTAGCCCAAAAGATACTTCCGATGATACTGGCATTTTGCAACACAAA
AATTTCATTAACCGAGTTTGTTAAATTATCGGGTAATGAGCTTAACCAG
TGGATGGAACAACTCCGTAAATTAACGGGACAAATAGTACCAAATCTGC
AACATCCTAAATTAAATAAGCTTTTTTCTTGGAAACAAAAAATAATAAA
TCTAGGCGAAGAGACTGCCGTTCTTATTCCGAAGATTGAGATCATAGAT
ATTACTAAAAATAAGATTTATATTTATGGCAAAGATGCATTACAGGTTT

-continued

CCACTAAGCTATTTTTAAACGGTTTCAGCATGATCACCGGATCAATCCA
AGCTTATACATTACAAGGTATGAGTTTGTATGAACGTAATGACCCATTA
AAACTATCCCCCTATAATCTGTATACAGCACAGATTATTGCGAATTTAT
TTGTAGCAAGCTACAGTATTTTAAAAGTTTCTCAAGAGGCGACAAAATT
ATCTCAAACAGTATCGAGCACCACACTGAAATTCTTTTTAGATAAAATA
AAATTACCTATGCTAACAACAGAAGTGGGAACCAAAAGAATGGCAGCAT
TAGGTAAGATTGCAGGTGCCGTTGGTGCCGCTCTTGCCGCTCGTGACGC
ATTAGAAGCTTTTCATATTGGAAATTATAAACAATCTGTATCAAATATA
GCTATTGTGATTGGTTCTATAATTTTAATTACTGCTGTTACTGGAGGAT
GGGCTTTATTTGCTGGGGCACTTATTTTGGGGGGATTTATCTCAAGCCA
ACTCACCAGTTGGAGTCATTTAGAAACTTTACTAAAACATAGTTTTTGG
GGGAATGAAAAAAGGTCTAATTTTTGGGATAATGATAGACCAACACCGA
TAGGAGAACAATTAAAACAATATATAAAAGAATTTGAATTCTATAAACA
AAAAGGGCTAATTGAATTACAAGAGTTTTATAATCTATTTTATACAGCT
AAAATGACTCAAGAAAAAATACCAAATGGAAAACTCCGCTTATCTTTTG
AATTTACTAATTTTACCCCAGGGATTTCAGAAGTATATTTTCACTTTGT
TACAGAGGTTGGTTATCACAGCGGCTTGGCAGAAGAAATAAAAACACCT
AGTTCAGCTTATGTTCTAAATAAACGAAAAGACCTCTTAGAAATTAGCG
AACAATTAAAAATGGCAAGTGAAAAAGGTGATTGGAACCCTGAAACAGG
TATATTTAAATTTAGTTTGGAAGTACAGTCTCAATTAGTAAATACATAT
TCTGCTTTTGGTGCACATCCTAATAGCCGTATAGGTATTGAAGATTTAT
ATTGGTATTATCAAGTCAATCCCGAGGTAACAACACCGATGCGTTATAT
CAATTGGGGGGGAGATACCCAAGAAAACAATCAGCTTTTAGGCTTTATT
AACAGTGAGAATATCTAA (SEQ ID NO: 2)

MTGEVNEKYLTPQERKARQMVKAVNEASPRNLPADAVVCPCENEHRPVY
PVRYAYTNEYCDLHFSTIEQAPNKTLEASIPPSINQLLNAKDVTASKGF
SARLLRQGWVYVFEEGNYPTRSNSSNKSYQEQNVDATKGRLLVFQHQVT
TSDGNENFIPYIFKQLKNGGVTLKKNGNSNPYLAIPKDVKEATILFSES
KLSDYTLKKIISSSKFRSKLMQKINFIDYNNNDYCIELNKDNLNRLVED
YKEEVDKFKLFVKEFTHSNIPSSFFSDTTKIPDLPQDATVLINQVNSVL
DYNEKATLLILKDPVGYQKDILSYYNIVTKLHLLYQNYYSHPDKIGQFI
TSIQEASHHIKDTDEKEKMQTILKESINQNALDNEWKNIHKTFIFFEKH
QRIVLSLYESFMNNPAIINENGGLKHYFDYAFSYHERITKEDVFSIDFF
KDLNQAFDLYFDLVSPLMNSIEGQRTLDKLYSINDEENNSLWVGVTKKV
ISLIANSKIKDALLNVQEYAMHIENFVNKLAFICSDSIGFAFTKTSKVL
SHYDIKNRLINTKGIDYLAQKILPMILAFCNTKISLTEFVKLSGNELNQ
WMEQLRKLTGQIVPNLQHPKLNKLFSWKQKIINLGEETAVLIPKIEIID
ITKNKIYIYGKDALQVSTKLFLNGFSMITGSIQAYTLQGMSLYERNDPL
KLSPYNLYTAQIIANLFVASYSILKVSQEATKLSQTVSSTTLKFFLDKI
KLPMLTTEVGTKRMAALGKIAGAVGAALAARDALEAFHIGNYKQSVSNI

-continued

AIVIGSTILTTAVTGGWALFAGALILGGFISSQLTSWSHLETLLKHSFW

GNEKRSNFWDNDRPTPIGEQLKQYIKEFEFYKQKGLIELQEFYNLFYTA

KMTQEKIPNGKLRLSFEFTNFTPGISEVYFHFVTEVGYHSGLAEEIKTP

SSAYVLNKRKDLLEISEQLKMASEKGDWNPETGIFKFSLEVQSQLVNTY

SAFGAHPNSRIGIEDLYWYYQVNPEVTTPMRYINWGGDTQENNQLLGFI

NSENI (underline: variable region)

In some embodiments, *Proteus mirabilis* IdsD corresponds to IdsD from *Proteus mirabilis* strain HI4320 (NCBI Reference Sequence: NC_010554.1:3282912 . . . 3286013, SEQ ID NO:3 (nucleotide) or SEQ ID NO:4 (amino acid)).

(SEQ ID NO: 3)

ATGACTGGAGAAGTGAATGAGAAATATTTAACACCGCAAGAGCGCAAAG

CGCGTCAGATGGTGAAGGCGGTAAACGAAGCGAGCCCACGAAACTTACC

GGCCGACGCGGTGGTATGCCCATGTGAAAATGAACATCGCCCTGTTTAT

CCGGTGCGTTATGCATATACCAACTTTTATTGTGATTTACATTTTTCTA

CAATTGAACAAGCACCAAATAAAACGTTAGAAGCGAGTATTCCTCCTTC

TATTAATCAATTATTGAATGCGAAAGATGTTACTGCTAGTAAAGGATTT

TCTGCAAGATTATTAAGACAAGGTTGGGTTTATGTTTTTGAAGAAGGCA

ATTACCCTACTAGAAGTAATTCTAGTAATAAAAGTTATCAAGAACAAAA

TGTTGATGCGACAAAAGGACGCCTATTAGTTTTTCAACATCAAGTTACA

ACCAGTGATGGCAATGAAAATTTCATTCCATATATATTTAAGCAATTAA

AAAATGGGGGTGTCACTTTAAAGAAAAACGGAAATAGTAATCCTTATTT

AGCTATACCGAAAGATGTGAAGGAAGCGACTATCTTATTCAGCGAAAGT

AAATTATCTGATTACACACTTAAAAAAATCATTTCATCTTCTAAGTTTA

GATCGAAATTAATGCAAAAAATCAATTTTATTGATTACAACAATAACGA

TTATTGTATTGAGCTAAATAAAGATAATTTAAATCGACTTGTTGAGGAT

TATAAAGAAGAAGTTGATAAATTTAAGCTATTTGTTAAAGAATTCACGC

ATTCAAATATACCCTCTTCTTTTTTTTCTGATACCACAAAAATACCCGA

CTTACCACAAGATGCAACTGTTTTGATTAATCAAATAAATAGTGTTCTA

GATTATAATGAAAAAGCGACATTGCTTATTTTAAAAGATCCCGTAGGAT

ACCAAAAAGATGTTTTATCTTATTATAATATTGTAACAAAATTACATTT

ATTATATCAGAACTATTATAGCCATCCGGATAAAATTGGCCAATTTATT

ACGAGTATACAAGAAGCTAGTCATCACATTAAAGATACTGATGAAAAAG

AAAAAATGCAAACAATACTAAAAGAGAGTATTAATCAGAATGCATTAGA

TAATGAGTGGAAAAAATATTCATAAAACATTTATTTTTTTTGAGAAACAT

CAACGTATTGTATTATCATTGTATGAAAGCTTTATGAATAATCCGGCAA

TCATTAATGAAAACGGTGGCTTAAAACATTATTTTGATTATGCTTTTTC

ATATCACGAACGTATAACGAAAGAAGATGTCTTTAGTATTGATTTTTTT

AAGGACCTTAATCAAGCTTTTGATTTATATTTTGATTTAATATCTCCAT

TAATGAATTCTACCGAAGGACAAAGAACATTAGATAAATTATATTCAAT

TAATGATGAAGAAAATAATAGCCTGTGGGTGGGAGTGACAAAGAAAGTA

-continued

ATTAGTCTTGTTGCTAATTCAAAAATTATGGACGCACTTTTAAATGCAC

AAGAATATGCAGAGAATATCGAAAATTTTGTTAATAAGCTTGCGTTTAT

TTGCTCAGATAGCATTGGTTTTGCATTTACAAAAACAAGTAAGATGCTT

TCTCATTACGATATTAAAAATAGACTAATTAATACTAAGGGTATTGACT

ATTTAGCTCAAAAGATACTTCCGATGATACTGGCATTTTGCAACACAAA

AATTTCATTAACCGAGTTTGTTAAATTATCGGGTAATGAGCTTAACCAG

TGGGTGGAACAACTCCGTAAATTAACGGAACAAATAGTACCAAATCTGC

AACATCCTAAATTAAATAAGCTTTTTTCTTGGAAACAAAAAAATAATAAA

TCTAGGCGAAGAGACTGCCGTTCTTATTCCGAAGATTGAGATCACAGAT

ATTACTAAAAATAAGATTTATATTTATGGTAAAGATGCATTACAGGTTT

CCACTAAGCTATTTTTAAACGGTTTCAGCATGATCACCGGATCAATCCA

AGCTTATACATTACAAGGTATGAGTTTGTATGAACGTAATGACCCATTA

AAACTATCCCCCTATAATCTGTATACAGCACAGATTATTGCGAATTTAT

TTGTAGCAAGCTACAGTATTTTAAAAGTTTCTCAAGAGGCGACAAAATT

ATCTCAAACAGTATCGAGCACCACACTGAAATTCTTTTTAGATAAAATA

AAATTACCTATGCTAACAACAGAAGTGGGAACCAAAAGAATGGCAGCAT

TAGGTAAGATTGCAGGTGCCGTTGGTGTTGCTCTTGCCACTCGAGATGC

ATTAGAAGCTTTTCATATTGGAAATAATAAACAAGGTTTATCAAATGTA

GCCATTGCCATTGGTTCTTTCATGCTAATTTTTGTTACAGGGGGATGGG

CTCTATTTGCAGGACTGCTAATATTAGGAGGCTTCTTCTCAAGTCAACT

CACCAGTTGGAGTCATTTGGAAACTTTGCTAAGGCACAGTTTTTGGGGA

AATGAAGAAAGTTCAAATTTTTGGGATAATAATAGACCAACACCGATAG

GAGAACAATTAAAACAATATATAAAAGAATTTGAATTCTATGAACAAAA

AGGGCTAATTGAATTACAAGAGTTTTATAATCTATTTTATACAGCTAAA

ATGACTCAAGAAAAAAATACCAAATGGAAAACTCCGCTTATCTTTTGAAT

TTACTAATTTTACCCCAGGGATTTCAGAAGTATATTTTCACTTTGTTAC

AGAGGTTGGTTATCACAGCGGCTTGGCAGAAGAAATAAAAACACCTAGT

TCAGCTTATGTTCTAAATAAACGAAAAGACCTCTTAGAAATTAGCGAAC

AATTAAAAATGGCAAGTGAAAAAGGTGATTGGAACCCTGAAACAGGTAT

ATTGAAATTTAGTTTGGAAGTACAGTCTCAATTAGTAAATACATATTCT

GCTTTTGGTGCACATCCTAATAGCCGTATAGGTATTGAAGATTTATATT

GGTATTATCAAGTCAATCCCGAGGTAACAACACCGATGCGTTATATCAA

TTGGGGGGGAGATACCCAAGAAAACAATCGGCTTTTAGGCTTTATTAAC

AGTGAGAATATCTAA (SEQ ID NO: 4)

MTGEVNEKYLTPQERKARQMVKAVNEASPRNLPADAVVCPCENEHRPVY

PVRYAYTNEYCDLHFSTIEQAPNKTLEASIPPSINQLLNAKDVTASKGF

SARLLRQGWVYVFEEGNYPTRSNSSNKSYQEQNVDATKGRLLVFQHQVT

TSDGNENFIPYIFKQLKNGGVTLKKNGNSNPYLAIPKDVKEATILFSES

KLSDYTLKKIISSSKFRSKLMQKINFIDYNNNDYCIELNKDNLNRLVED

YKEEVDKFKLFVKEFTHSNIPSSFFSDTTKIPDLPQDATVLINQINSVL

-continued

```
DYNEKATLLILKDPVGYQKDVLSYYNIVTKLHLLYQNYYSHPDKIGQFI
TSIQEASHHIKDTDEKEKMQTILKESINQNALDNEWKNIHKTFIFFEKH
QRIVLSLYESFMNNPAIINENGGLKHYFDYAFSYHERITKEDVFSIDFF
KDLNQAFDLYFDLISPLMNSTEGQRTLDKLYSINDEENNSLWVGVTKKV
ISLVANSKIMDALLNAQEYAENIENFVNKLAFICSDSIGFAFTKTSKML
SHYDIKNRLINTKGIDYLAQKILPMILAFCNTKISLTEFVKLSGNELNQ
WVEQLRKLTEQIVPNLQHPKLNKLFSWKQKIINLGEETAVLIPKIEITD
ITKNKIYIYGKDALQVSTKLFLNGFSMITGSIQAYTLQGMSLYERNDPL
KLSPYNLYTAQIIANLFVASYSILKVSQEATKLSQTVSSTTLKFFLDKI
KLPMLTTEVGTKRMAALGKIAGAVGVALATRDALEAFHIGNNKQGLSNV
AIAIGSFMLIFVTGGWALFAGLLILGGFFSSQLTSWSHLETLLRHSFWG
NEESSNFWDNNRPTPIGEQLKQYIKEFEFYEQKGLIELQEFYNLFYTAK
MTQEKIPNGKLRLSFEFTNFTPGISEVYFHFVTEVGYHSGLAEEIKTPS
SAYVLNKRKDLLEISEQLKMASEKGDWNPETGILKFSLEVQSQLVNTYS
AFGAHPNSRIGIEDLYWYYQVNPEVTTPMRYINWGGDTQENNRLLGFIN
SENI
```

(underline: variable region)

The terms "*P. mirabilis* IdsE" and "E," as used herein, refers interchangeably to *Proteus mirabilis* IdsE. In some embodiments, *Proteus mirabilis* IdsE corresponds to IdsE from *Proteus mirabilis* strain BB2000 (NCBI Reference Sequence: EU635876.1:9139 . . . 10077, SEQ ID NO:5 (nucleotide) or SEQ ID NO:6 (amino acid)).

(SEQ ID NO: 5)

```
ATGAGTATTTTTTTTAATCCCGCTAAACACCCACATCGCTTAAAGCCAC
AACCATTAGGGACGCAAGGCGAGCACTATAACGAAGATTGGCCCATGCC
TGAGCTCGATTTTTTAGAGACCGTAGATAAACAACAGTGCATTCTGGTT
GATAAAGAAATACGCCGACGTGATGCGTTTGCTTTCCCTGGGTTTATTA
CCGGTATTATTACCTTTATTATGGTGTTTCATTTTGTTTTTACAGAACA
TAATTCAAAGTATATCCGTTTTAATAAAAATCTTCATGACTATACATTA
GAATATAAAGCCCAATATGAAGATAAAGCCCAAAGAGATAAACTACCTT
CATTTATACTTGATAAGTACGCCCCTTATTTCAATCAAGAAAAACTGTC
TATTTTAGATTATATTCATGTTTATTTTGGGGGTCATATTACATCAACC
CCTTATATTGATACTTCCATTTTGTCTACCCTACTCATTTCATTAGTTT
ATTTAATTGTAGTATCTGGCTATCAATCTTTTTTCAAAAAAAATCCAAT
ACTCGTTTTTAATCGTGAAAGAAATCTGGTCTATACTTGGCGCAAAAAT
AAGGTATTTATTGCCCGCTATCCTGAAATTGGTATCGGTAAAATTGGTA
AAACACTTACCTTTCAATTATTCGGGTTAGATAAGTCAAAACAAACTTT
AGTTTCTGAATTGTTTTTCCCTAATGTCTATGTTTATTCAGTCTACAAT
ACCAGTACTGACTATCACGACCAGCGCTTCATTAATTTTATCAATACTT
ATATGCGCGAAGGGCGTGATGCCATTATTCCATTCGATTATCACCGTAA
AAAACCCAAAGTGTATTTTGGCAAAAACCCACCTCCTGCTGATTTTGAA
CAACAGGTCGAACAAATTTTAGCAAAGCTTGATCAGGAGAAAGAACACC
ATGCGTAG
```

(SEQ ID NO: 6)

```
MSIFFNPAKHPHRLKPQPLGTQGEHYNEDWPMPELDFLETVDKQQCILV
DKEIRRRDAFAFPGFITGIITFIMVFHFVFTEHNSKYIRFNKNLHDYTL
EYKAQYEDKAQRDKLPSFILDKYAPYFNQEKLSILDYIHVYFGGHITST
PYIDTSILSTLLISLVYLIVVSGYQSFFKKNPILVFNRERNLVYTWRKN
KVFIARYPEIGIGKIGKTLTFQLFGLDKSKQTLVSELFFPNVYVYSVYN
TSTDYHDQRFINFINTYMREGRDAIIPFDYHRKKPKVYFGKNPPPADFE
QQVEQILAKLDQEKEHHA
```

(underline: variable region)

In some embodiments, *Proteus mirabilis* IdsE corresponds to IdsE from *Proteus mirabilis* strain HI4320 (NCBI Reference Sequence: NC_010554.1:3286013 . . . 3286951, SEQ ID NO:7 (nucleotide) or SEQ ID NO:8 (amino acid)).

(SEQ ID NO: 7)

```
ATGAGTATTTTTTTCAATCCCGCTAAACACCCACATCGCTTGAAGCCAC
AACCATTGGGGGAGCAAGGTGAGCGCTATAACGAAGATTGGCCCATGCC
TGAGCTCGATTTTTTAGAGACCGTGGATAAACAACAGTGCATTCTGGTT
GATAAAGAAATACGCCGACGTGATGCGTTTGCTTTCCCTGGGTTTATTA
CCGGTATTATTACCTTTATTATGGTATTTCATTTTGTTTTTACAGAACA
TAATTCAAAGTATATCCGTTTTAATAAAAATCTTCATGACTATACATTA
GAATATAAAGCGCAATATGAAGATAAAACTCAAAGAGATAAACTACCTT
CATTTATACTTGATAAGTACGCCCCTTATTTCAATCAAGAAAAACTGTC
TATTTTAGATTATATTCATGTTTATTTTGGGGGACATATTACATCAAAA
CCCTATCAAAATACGCTATTTTTTCTTTCTACTTTCATCGCACCTTTCT
TCTTAATTGGCTTGGGTGGCTATCAATCTTTTTTCAAAAAAAATCCAAT
ACTCGTTTTTAATCGTGAAAGAAATCTGGTTTATACTTGGCGCAAAAAT
AAGGTATTTATTGCCCGCTATCCTGAAATTGGTATCGGTAAAATTGGTA
AAACACTTACCTTTCAATTATTCGGGTTAGATAAGTCAAAACAAACTTT
AGTTTCTGAATTATTTTTCCCTAATGTCTATGTTTATTCAGTGTACAAT
ACCAGTACTGACTATCACGACCAGCGCTTCATTAATTTTATCAATACTT
ATATGCGCGAAGGGCGTGATGCCATTATTCCATTCGATTATCACCGTAA
AAAACCCAAAGTGTATTTTGGCAAAAACCCACCTCCTGCTGATTTTGAG
CAACAGGTCGAACAGATTTTAGCAAAGCTTGATCAGGAGAAAAAACACC
ATGCGTAG
```

(SEQ ID NO: 8)

```
MSIFFNPAKHPHRLKPQPLGEQGERYNEDWPMPELDFLETVDKQQCILV
DKEIRRRDAFAFPGFITGIITFIMVFHFVFTEHNSKYIRFNKNLHDYTL
EYKAQYEDKTQRDKLPSFILDKYAPYFNQEKLSILDYIHVYFGGHITSK
PYQNTLFFLSTFIAPFFLIGLGGYQSFFKKNPILVFNRERNLVYTWRKN
KVFIARYPEIGIGKIGKTLTFQLFGLDKSKQTLVSELFFPNVYVYSVYN
```

-continued

TSTDYHDQRFINFINTYMREGRDAIIPFDYHRKKPKVYFGKNPPPADFE

QQVEQILAKLDQEKKHHA (underline: variable region)

The term "recombinant" as used herein in the context of proteins or nucleic acids refers to proteins or nucleic acids that do not occur in nature, but are the product of human engineering. For example, in some embodiments, a recombinant protein or nucleic acid molecule comprises an amino acid or nucleotide sequence that comprises at least one, at least two, at least three, at least four, at least five, at least six, or at least seven mutations as compared to any naturally occurring sequence.

The term "subject," as used herein, refers to any animal subject including humans, laboratory animals (e.g., primates, rats, mice), livestock (e.g., cows, sheep, goats, pigs, turkeys, chickens), and household pets (e.g., dogs, cats, rodents). The subject may be healthy, or may be suffering from a bacterial infection, or may be at risk of developing or transmitting to others a bacterial infection.

The term "swarming," as used herein, refers to rapid (approximately 2-10 μm/s) and coordinated translocation of a bacterial population across solid or semi-solid surfaces. Flagellated bacteria are capable of both moving in association with other cells in a thin film of liquid over a moist surface (i.e., swarming) or moving independently in bulk liquid (i.e., swimming).

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term "urinary tract infection," as used herein, refers to infection of the kidney, ureter, bladder, or urethra. Cystitis is a related condition caused by bacteria entering the urethra and then the bladder, leading to inflammation and infection in the lower urinary tract. Pyelonephritis is a related condition comprising infection of the kidney and/or the ureters. Urinary tract infections may be infections of the upper urinary tract, the lower urinary tract, or both. Urinary tract infections may be chronic or acute.

The term "variable region," as used herein, refers to interacting regions in *Proteus mirabilis* IdsD and IdsE that are characterized by high sequence variability and predicted transmembrane localization.

In some embodiments, the variable region in *P. mirabilis* IdsD corresponds to the variable region in IdsD from *Proteus mirabilis* strain BB2000 (NCBI Reference Sequence: EU635876.1:8316 . . . 8631, SEQ ID NO:9 (nucleotide) or SEQ ID NO:10 (amino acid)).

(SEQ ID NO: 9)

GCCGCTCTTGCCGCTCGTGACGCATTAGAAGCTTTTCATATTGGAAATT

ATAAACAATCTGTATCAAATATAGCTATTGTGATTGGTTCTATAATTTT

AATTACTGCTGTTACTGGAGGATGGGCTTTATTTGCTGGGGCACTTATT

TTGGGGGGATTTATCTCAAGCCAACTCACCAGTTGGAGTCATTTAGAAA

CTTTACTAAAACATAGTTTTTGGGGGAATGAAAAAAGGTCTAATTTTTG

GGATAATGATAGACCAACACCGATAGGAGAACAATTAAAACAATATATA

AAAGAATTTGAATTCTATAAA (SEQ ID NO: 10)

AALAARDALEAFHIGNYKQSVSNIAIVIGSIILITAVTGGWALFAGALI

LGGFISSQLTSWSHLETLLKHSFWGNEKRSNFWDNDRPTPIGEQLKQYI

KEFEFYK

In some embodiments, the variable region in *Proteus mirabilis* IdsD corresponds to the variable region in IdsD from *Proteus mirabilis* strain HI4320 (NCBI Reference Sequence: NC_010554.1:3287473 . . . 3287788, SEQ ID NO:11 (nucleotide) or SEQ ID NO:12 (amino acid)).

(SEQ ID NO: 11)

GTTGCTCTTGCCACTCGAGATGCATTAGAAGCTTTTCATATTGGAAATA

ATAAACAAGGTTTATCAAATGTAGCCATTGCCATTGGTTCTTTCATGCT

AATTTTTGTTACAGGGGGATGGGCTCTATTTGCAGGACTGCTAATATTA

GGAGGCTTCTTCTCAAGTCAACTCACCAGTTGGAGTCATTTGGAAACTT

TGCTAAGGCACAGTTTTTGGGGAAATGAAGAAAGTTCAAATTTTTGGGA

TAATAATAGACCAACACCGATAGGAGAACAATTAAAACAATATATAAAA

GAATTTGAATTCTATGAACAA (SEQ ID NO: 12)

VALATRDALEAFHIGNNKQGLSNVAIAIGSFMLIFVTGGWALFAGLLIL

GGFFSSQLTSWSHLETLLRHSFWGNEESSNFWDNNRPTPIGEQLKQYIK

EFEFYEQ

In some embodiments, the variable region in *Proteus mirabilis* IdsE corresponds to the variable region in IdsE from *Proteus mirabilis* strain BB2000 (NCBI Reference Sequence: EU635876.1:9578 . . . 9647, SEQ ID NO:13 (nucleotide) or SEQ ID NO:14 (amino acid)).

(SEQ ID NO: 13)
ACCCCTTATATTGATACTTCCATTTTGTCTACCCTACTCATTTCATTAG

TTTATTTAATTGTAGTATCT (SEQ ID NO: 14)
TPYIDTSILSTLLISLVYLIVVS

In some embodiments, the variable region in *Proteus mirabilis* IdsE corresponds to the variable region in IdsE from *Proteus mirabilis* strain HI4320 (NCBI Reference Sequence: NC_010554.1:3286452 . . . 3286521, SEQ ID NO:15 (nucleotide) and/or SEQ ID NO:16 (amino acid)).

(SEQ ID NO: 15)
AAACCCTATCAAAATACGCTATTTTTTCTTTCTACTTTCATCGCACCTT

TCTTCTTAATTGGCTTGGGT (SEQ ID NO: 16)
KPYQNTLFFLSTFIAPFFLIGLG

The term "vector," as used herein, refers to any nucleic acids capable of transferring genetic material into a cell (e.g., bacteria). The vector may be linear or circular in topology and includes, but is not limited to, plasmids or bacteriophages. The vector may include amplification genes, enhancers, or selection markers and may or may not be integrated into the genome of the host organism.

DETAILED DESCRIPTION OF CERTAIN EMBODIMENTS OF THE INVENTION

The present disclosure provides compositions, kits, systems, and methods for reducing bacteria on a surface (e.g., a medical device) and preventing and/or treating a bacterial infection (e.g., urinary tract infection) in a subject using IdsD protein or a fragment thereof.

In some embodiments, the IdsD protein or fragment thereof comprises an amino acid sequence that is not identical to the amino acid sequence of a naturally occurring *Proteus mirabilis* IdsD protein. In some embodiments, the IdsD protein fragment comprises the variable region. In some embodiments, the variable region comprises one or more mutations. In some embodiments, the IdsD protein or fragment thereof is provided by nucleic acids encoding the IdsD protein or fragment thereof. In some embodiments, the IdsD protein is provided by a bacterial composition comprising the IdsD protein. In some embodiments, the bacterial composition comprises *Proteus mirabilis*. In some embodiments, the IdsD protein is provided by a pharmaceutical composition comprising the IdsD protein and a pharmaceutically acceptable carrier. In some embodiments, the IdsD protein further comprises one or more therapeutic agents.

In some embodiments, the disclosure provides a method of reducing bacterial growth and/or swarming on a surface comprising contacting or coating the surface with IdsD protein. In some embodiments, contacting or coating comprises spraying, brushing, applying, and/or treating the surface with IdsD protein.

In some embodiments, the disclosure provides a method for reducing the occurrence of urinary tract infections in a subject with a medical device comprising coating of a medical device with IdsD protein and implanting the device in a subject. In some embodiments, the medical device is a catheter, sphincter, dilator, stent, tissue bonding device, graft, drain tube, shunt, joint replacement, pacemaker system, valve, or prosthesis. In some embodiments, the subject is a human.

In some embodiments, the disclosure provides a method for treating or preventing a bacterial infection, the method comprising administering to a subject in need thereof a therapeutically effective amount of IdsD protein. In some embodiments, the bacterial infection is a urinary tract infection. In some embodiments, the urinary tract infection is a catheter-associated urinary tract infection. In some embodiments, the bacterial infection is a *Proteus mirabilis* infection. In some embodiments, the method further comprises screening the *Proteus mirabilis* infection for IdsD and/or IdsE. In some embodiments, screening the *Proteus mirabilis* infection for IdsD and/or IdsE comprises sequencing assays, binding assays, and/or boundary formation assays. In some embodiments, the method further comprises administering one or more other therapeutic agents. In some embodiments, the other therapeutic agent is an antibiotic. In some embodiments, the subject is human.

In some embodiments, the disclosure provides a medical device kit comprising a medical device and IdsD protein. In some embodiments, the medical device is a catheter, sphincter, dilator, stent, tissue bonding device, graft, drain tube, shunt, joint replacement, pacemaker system, valve, or prosthesis.

*Proteus mirabilis* IdsD Protein

*Proteus mirabilis* comprises six ids genes, idsABCDEF, encoding six proteins, IdsABCDEF. IdsD and IdsE function as a heteromeric bacterial self-recognition system as exemplified in *P. mirabilis* strains BB2000 and HI4320. It should be understood that *P. mirabilis* strains BB2000 and HI4320 are used throughout this disclosure as an exemplary embodiment and in a non-limiting manner. Thus, the various aspects and embodiments of this disclosure that refer to IdsD and IdsE from *P. mirabilis* strains BB2000 and HI4320 apply equally to IdsD and IdsE from any strain of *P. mirabilis* unless otherwise stated.

IdsD protein comprises 1,034 amino acids corresponding to SEQ ID NO:2 (strain BB2000) or SEQ ID NO:4 (strain HI4320). IdsE protein comprises 312 amino acids corresponding to SEQ ID NO:6 (strain BB2000) or SEQ ID NO:8 (strain HI4320). Without being bound by theory, IdsD and IdsE proteins function as a heteromeric bacterial self-recognition system when IdsD protein from a donor cell (e.g., donor cell is strain BB2000) interacts with IdsE protein in a recipient cell (e.g., recipient cell is strain BB2000), thereby merging swarming populations of donor and recipient cells. When IdsD protein from a donor cell (e.g., donor cell is strain BB2000) is transferred but does not interact with IdsE protein in a recipient cell (e.g., recipient cell is strain HI4320), swarm colony expansion is negatively impacted, thereby forming a boundary between swarming populations of genetically distinct bacteria. The lack of IdsD and IdsE protein interaction in recipient cells does not impact bacterial viability.

IdsD and IdsE proteins that interact, thereby merging swarming populations of bacteria are referred to as cognate IdsD-IdsE pairs. IdsD and IdsE proteins that do not interact, thereby forming a boundary between populations of bacteria are referred to as non-cognate IdsD-IdsE pairs. Interacting regions in IdsD and IdsE proteins are characterized by high sequence variability and predicted transmembrane localization. The variable region in IdsD comprises amino acid residues 761 to 865 corresponding to SEQ ID NO:2 (BB2000) or SEQ ID NO:4 (HI4320). Two residues in IdsD located at positions 761 and 765 are important for mediating interaction with the variable region in IdsE. The variable region in IdsE comprises amino acid residues 147-169 corresponding to SEQ ID NOS: 6 (BB2000) or SEQ ID NO:8 (HI4320).

Some aspects of this disclosure provide IdsD protein, or a fragment thereof, for reducing bacterial growth and/or swarming (e.g., on a surface) and for treating a subject having a bacterial infection (e.g., a urinary tract infection). Non-limiting, exemplary compositions comprising IdsD protein, or a fragment thereof, are provided herein.

IdsD Protein

Some aspects of this disclosure provide IdsD protein comprising an amino acid sequence as provided by SEQ ID NO:2 or SEQ ID NO:4, or a fragment thereof, wherein the IdsD protein comprises a variable region that is at least 70%, at least 75%, at least 80%, at least 85%, at least 90%, at least 92%, at least 95%, at least 96%, at least 97%, at least 98%, at least 99%, or at least 99.5% identical to the amino acid sequence of IdsD protein as provided by SEQ ID NO:10 or SEQ ID NO:12, and wherein the amino acid sequence of the IdsD protein is not identical to the amino acid sequence of a naturally occurring *Proteus mirabilis* IdsD protein.

In some embodiments, the IdsD protein is a fragment comprising the variable region. In some embodiments, the IdsD protein fragment is at least 70%, at least 75%, at least 80%, at least 85%, at least 90%, at least 92%, at least 95%, at least 96%, at least 97%, at least 98%, at least 99%, or at least 99.5% identical to the IdsD variable region from *P. mirabilis* strain BB2000 corresponding to SEQ ID NO:2 (underline: variable region) or SEQ ID NO:10. In some embodiments, the IdsD protein fragment is at least 70%, at least 75%, at least 80%, at least 85%, at least 90%, at least 92%, at least 95%, at least 96%, at least 97%, at least 98%, at least 99%, or at least 99.5% identical to the IdsD variable region from *P. mirabilis* strain HI4320 corresponding to SEQ ID NO:4 (underline: variable region) or SEQ ID NO:12.

In some embodiments, the variable region comprises one or more mutations. In some embodiments, the one or more mutations is at least one, at least two, at least three, at least four, at least five, at least six, at least seven, at least eight, at least nine, at least ten, at least fifteen, at least twenty, or at least twenty five mutations in the variable region. In some embodiments, the one or more mutations are mutations to amino acid residues 761 and/or 765 of amino acid sequences provided by SEQ ID NO:2 or SEQ ID NO:4. In some embodiments, the one or more mutations are mutations to amino acid residues 1 and/or 5 of amino acid sequences provided by SEQ ID NO:10 or SEQ ID NO:12.

In some embodiments, the IdsD protein is a recombinant IdsD protein. In some embodiments, the IdsD protein is an IdsD fusion protein. In some embodiments, the IdsD fusion protein is formed, for example, by an in-frame gene fusion to result in the expression of IdsD protein or polypeptide fragment thereof fused to a second polypeptide, such as an affinity tag for purification or identification, a fluorescent polypeptide for in situ visualization of the fusion protein, or any polypeptides that promote bacterial uptake of the fusion protein.

In some embodiments, the IdsD protein may comprise one or more distinct amino acid sequences. For example, the IdsD protein may comprise a mixture of IdsD protein having sequence similarity to IdsD protein from *P. mirabilis* strain BB2000 and IdsD protein having sequence similarity to IdsD protein from *P. mirabilis* strain HI4320.

Some aspects of this disclosure provide IdsD protein in a therapeutically effective amount. In some embodiments, a therapeutically effective amount of IdsD protein as provided herein may vary depending upon known factors such as use and length of use, pharmaceutical characteristics of the composition, and age, sex, weight, and health of the subject. In some embodiments, the therapeutically effective amount of IdsD protein is between 0.1 and 0.5 mg. In some embodiments, the therapeutically effective amount of IdsD protein is between 0.5 and 1 mg. In some embodiments, the therapeutically effective amount of IdsD protein is between 1 and 10 mg.

In some aspects of this disclosure, IdsD protein is provided by nucleic acids. In some embodiments, the nucleic acids encoding the IdsD protein are provided by SEQ ID NO:1 or SEQ ID NO:3. In some embodiments, the nucleic acids encoding the IdsD protein are provided by SEQ ID NO:9 or SEQ ID NO:11. In some embodiments, the nucleic acid encoding IdsD protein is a vector that renders a bacteria capable of expressing IdsD protein. In some embodiments, the nucleic acid encoding IdsD protein is DNA. In some embodiments, the nucleic acid encoding IdsD protein is RNA.

In some aspects of this disclosure, IdsD protein is provided by a bacterial composition secreting IdsD protein. In some embodiments, the bacterial composition comprises a non-pathogenic bacteria. In some embodiments, the bacterial composition comprises *Proteus mirabilis.*

In some embodiments, a bacterial composition secreting IdsD protein is coated onto a surface. In some embodiments, the surface is coated with between $10^2$ and $10^3$ colony forming units per centimeter of surface. In some embodiments, the surface is coated with between $10^3$ and $10^4$ colony forming units per centimeter of surface. In some embodiments, the surface is coated with between $10^4$ and $10^5$ colony forming units per centimeter of surface.

In some embodiments, the bacteria composition comprises viable whole cells of the bacteria. In some embodiments, the bacteria composition comprises non-viable whole cells or cellular extracts of the bacteria. In some embodiments, the bacteria composition comprises viable whole cells and non-viable whole cells or cellular extracts of the bacteria. In some embodiments, the bacteria composition comprises two or more types of bacteria.

In some aspects of this disclosure, IdsD protein is provided by a pharmaceutical composition comprising the IdsD protein and a pharmaceutically acceptable carrier. In some embodiments, the IdsD protein further comprises one or more therapeutic agents. In some embodiments, the therapeutic agent is an antibiotic.

Pharmaceutical Compositions

The present invention provides pharmaceutical compositions comprising *P. mirabilis* IdsD for use in inhibiting bacterial growth and/or swarming. Pharmaceutical compositions may comprise any suitable *P. mirabilis* IdsD compositions as provided herein. In some embodiments, the pharmaceutical composition comprises *P. mirabilis* IdsD protein. In some embodiments, the pharmaceutical composition comprises nucleic acids encoding *P. mirabilis* IdsD. In some embodiments, the pharmaceutical composition comprises a bacterial composition that secretes *P. mirabilis* IdsD. In some embodiments, the pharmaceutical composition comprises a pharmaceutical composition comprising *P. mirabilis* IdsD.

In some embodiments, the pharmaceutical composition is coated onto a medical device. In some embodiments, the pharmaceutical composition is for use in preventing and/or treating a bacterial infection. In some embodiments, the pharmaceutical composition is for use in preventing and/or treating a urinary tract infection. In some embodiments, the pharmaceutical composition is for use in preventing and/or treating a catheter-associated urinary tract infection.

In some embodiments, *P. mirabilis* IdsD is provided in an effective amount in the pharmaceutical composition. In some embodiments, the effective amount is effective for preventing and/or treating a bacterial infection in a subject in need thereof. In some embodiments, the effective amount is effective for preventing and/or treating a urinary tract infection in a subject in need thereof. In some embodiments, the effective amount is effective for preventing and/or treating a catheter-associated urinary tract infection in a subject in need thereof. In some embodiments, the effective amount is effective for preventing and/or reducing bacterial growth. In some embodiments, the effective amount is effective for preventing and/or reducing bacterial swarming. In some embodiments, the effective amount is a therapeutically effective amount. In some embodiments, the effective amount is a prophylactically effective amount.

The pharmaceutical compositions described herein may be useful in preventing and/or treating bacterial infection in a subject. In some embodiments, the bacterial infection is a *Proteus mirabilis* infection. In some embodiments, the bacterial infection is a gram-negative bacterial infection. Examples of gram-negative bacteria that may infect a subject include, but are not limited to, *Escherichia, Shigella, Edwardsiella, Salmonella, Citrobacter, Klebsiella, Enterobacter, Hafnia, Serratia, Morganella, Providencia, Yersinia, Erwinia, Buttlauxella, Cedecea, Ewingella, Kluyvera, Tatumella, Rahnella, Pseudomonas aeruginosa, Stenotrophomonas maltophilia, Burkholderia, Cepacia, Gardenerella, Vaginalis*, or *Acinetobacter*. In some embodiments, the bacterial infection is a gram-positive bacterial infection. Examples of gram-negative bacteria that may infect a subject include, but are not limited to, *Staphylococcus*, Streptococci, Enterococci, Corynebacteria, and *Bacillus* species.

It will also be appreciated that the compositions described herein can be employed in combination therapies, that is, the compositions or pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

In addition to *P. mirabilis* IdsD, the pharmaceutical composition described herein may comprise one or more additional pharmaceutical agents. In some embodiments, the additional pharmaceutical agent is an antimicrobial including, but not limited to, an antibiotic, an antifungal, or an antiviral.

Examples of antibiotics include, but are not limited to penicillins, cephalosporins, carbepenems, other beta-lactams antibiotics, aminoglycosides, macrolides, lincosamides, glycopeptides, tetracylines, chloramphenicol, quinolones, fucidins, sulfonamides, trimethoprims, rifamycins, oxalines, streptogramins, lipopeptides, ketolides, polyenes, azoles, and echinocandins.

Examples of antifungals include, but are not limited to, polyene antifungals—natamycin, rimocidin, filipin, nystatin, amphotericin B, candicin, and hamycin; imidazole antifungals—miconazole, ketoconazole, clotrimazole, econazole, omoconazole, bifonazole, butoconazole, fenticonazole, isoconazole, oxiconazole, sertaconazole, sulconazole, and tioconazole; triazole antifungals—fluconazole, itraconazole, isavuconazole, ravuconazole, posaconazole, voriconazole, terconazole, and albaconazole; thiazole antifungals—abafungin; allylamine antifungals—terbinafine, naftifine, and butenafine; and echinocandin antifungals—anidulafungin, caspofungin, and micafungin. Other compounds that have antifungal properties include, but are not limited to polygodial, benzoic acid, ciclopirox, tolnaftate, undecylenic acid, flucytosine or 5-fluorocytosine, griseofulvin, and haloprogin.

Examples of antivirals include, but are not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, Foscarnet, Fomivirsen, Ganciclovir, Indinavir, Idoxuridine, Lamivudine, Lopinavir Maraviroc, MK-2048, Nelfinavir, Nevirapine, Penciclovir, Raltegravir, Rilpivirine, Ritonavir, Saquinavir, Stavudine, Tenofovir Trifluridine, Valaciclovir, Valganciclovir, Vidarabine, Ibacitabine, Amantadine, Oseltamivir, Rimantidine, Tipranavir, Zalcitabine, Zanamivir and Zidovudine.

In some embodiments, the compound or pharmaceutical composition is a solid. In some embodiments, the compound or pharmaceutical composition is a powder. In some embodiments, the compound or pharmaceutical composition can be dissolved in a liquid to make a solution. In some embodiments, the compound or pharmaceutical composition is dissolved in water to make an aqueous solution. In some embodiments, the pharmaceutical composition is a liquid for topical administration (e.g., skin of a subject in need thereof). In some embodiments, the pharmaceutical composition is a liquid for coating a medical device (e.g., catheter). In some embodiments, the pharmaceutical composition is a liquid for oral administration (e.g., ingestion). In some embodiments, the pharmaceutical composition is a liquid for parental injection. In some embodiments, the pharmaceutical composition is a liquid (e.g., aqueous solution) for intravenous injection. In some embodiments, the pharmaceutical composition is a liquid (e.g., aqueous solution) for subcutaneous injection.

After formulation with an appropriate pharmaceutically acceptable excipient in a desired dosage, the pharmaceutical compositions of this invention can be administered to humans and other animals orally, parenterally, intracisternally, intraperitoneally, topically, bucally, or the like, depending on the disease or condition being treated. In some embodiments, a pharmaceutical composition comprising IdsD protein is administered, orally or parenterally, at dosage levels of each pharmaceutical composition sufficient to deliver from about 0.001 mg/kg to about 200 mg/kg in one or more dose administrations for one or several days (depending on the mode of administration).

In some embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In some embodiments, the compounds described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In some embodiments, the desired dosage may be delivered using multiple administrations (e.g., two, three, four, five, six, seven, eight, nine, ten, eleven, twelve, thirteen, fourteen, or more administrations). In some embodiments, each composition described herein is administered at a dose that is below the dose at which the agent causes non-specific effects.

In some embodiments, the pharmaceutical composition is administered at a dose of about 0.001 mg to about 200 mg a day. In some embodiments, the pharmaceutical composition is administered at a dose of about 0.01 mg to about 100 mg a day. In some embodiments, pharmaceutical composition is administered at a dose of about 0.01 mg to about 50 mg a day. In some embodiments, the pharmaceutical composition is administered at a dose of about 0.01 mg to about 10 mg a day. In some embodiments, the pharmaceutical composition is administered at a dose of about 0.1 mg to about 10 mg a day.

Pharmaceutical compositions described herein can be prepared by any method known in the art of pharmacology. In general, such preparatory methods include the steps of bringing the composition comprising IdsD protein, into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present invention contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., quids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

Methods of Coating a Surface

In one aspect, the present disclosure provides IdsD protein for use in inhibiting bacterial growth and/or swarming on a surface. In some embodiments, the IdsD protein is coated onto a surface that may be prone to bacterial contamination. In some embodiments, the IdsD protein is coated onto a surface contaminated by a bacteria. In some embodiments, the IdsD protein is applied prophylactically over a "clean" surface that is not contaminated by bacteria.

In some embodiments, the IdsD protein is coated onto a medical device. Exemplary medical devices include, but are not limited to, catheters such as urinary catheters, venous catheters, arterial catheters, dialysis catheters, peritoneal catheters, urinary sphincters, urinary dilators, urinary stents, tissue bonding urinary devices, vascular grafts, vascular dilators, extravascular dilators, vascular stents, extravascular stents, wound drain tubes, shunts, pacemaker systems, joint replacements, heart valves, cardiac assist valves, bone prosthesis, joint prosthesis, or dental prosthesis.

The area of a surface coated by IdsD protein should be sufficient for inhibiting bacterial growth and/or swarming on the surface. In some embodiments, the IdsD protein is coated on at least a part of the surface. In some embodiments, the IdsD protein is coated on at least 1%, at least 5%, at least 10%, at least 20%, at least 30%, at least 40%, at least 50%, at least 60%, at least 70%, at least 80%, at least 90%, or at least 99.5% of the surface.

Any suitable IdsD protein for use in inhibiting bacterial growth and/or swarming on a surface may be coated onto the surface. In some embodiments, the IdsD protein is a liquid. In some embodiments, the IdsD protein is a powder. In some embodiments, the IdsD protein can be dissolved in a liquid to make a solution. In some embodiments, the IdsD protein-containing liquid can be a solution, a suspension, a colloid, or a dispersion.

Any method suitable for coating IdsD protein onto a surface may be used. In some embodiments, coating IdsD protein onto a surface comprises spraying IdsD protein onto the surface. In some embodiments, coating IdsD protein onto a surface comprises brushing IdsD protein onto the surface. In some embodiments, coating IdsD protein onto a surface comprises applying IdsD protein onto the surface. In some embodiments, coating IdsD protein onto a surface comprises treating IdsD protein onto the surface.

Any amount of IdsD protein suitable for inhibiting bacterial growth and/or swarming on a surface may be used. In some embodiments, the surface has between 0.1 and 1.0 mg of IdsD protein per $cm^2$ of surface area. In some embodiments, the surface has between 1 and 10 mg of IdsD protein per $cm^2$ of surface area. In some embodiments, the surface has between 10 and 100 mg of IdsD protein per $cm^2$ of surface area.

Any thickness of IdsD protein coating that does not altering the functionality of a surface may be coated onto the surface. In some embodiments, the IdsD protein coating is between about 0.0001 millimeters and 10 millimeters in thickness. In some embodiments, the IdsD protein coating is between 0.5 and about 5 millimeters in thickness. In some embodiments, the IdsD protein coating is between 1 and about 4 millimeters in thickness.

Methods of Preventing and/or Treating a Bacterial Infection

In one aspect, the present disclosure provides methods for preventing and treating bacterial infections in a subject using IdsD protein. In some embodiments, the bacterial infection is a *Proteus mirabilis* infection. In some embodiments, the bacterial infection is caused by a Gram-positive bacterium. Exemplary Gram-positive bacteria include, but are not limited to, species of the genera *Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium*, and *Corynebacterium*. In some embodiments, the Gram-positive bacterium is a bacterium of the phylum Firmicutes. In some embodiments, the bacterium is a member of the phylum Firmicutes and the genus *Enterococcus*, i.e., the bacterial infection is an *Enterococcus* infection. Exemplary Enterococci bacteria include, but are not limited to, *E. avium, E. durans, E. faecalis, E. faecium, E. gallinarum, E. solitarius, E. casseliflavus*, and *E. raffinosus*. In some embodiments, the *Enterococcus* infection is an *E. faecalis* infection. In some embodiments, the *Enterococcus* infection is an *E. faecium* infection. In some embodiments, the bacteria is a member of the phylum Firmicutes and the genus *Staphylococcus*, i.e., the bacterial infection is a *Staphylococcus* infection. Exemplary Staphylococci bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri*, and *S. xylosus*. In some embodiments, the *Staphylococcus* infection is an *S. aureus* infection. In some embodiments, the *Staphylococcus* infection is an *S. epidermis* infection. In some embodiments, the Gram-positive bacterium is selected from the group consisting of *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae, Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes, Streptococcus salivarius, Streptococcus sanguis, Bacillus anthracis, Clostridium botulinum, Clostridium perfringens, Clostridium tetani, Corynebacterium diphtheriae, Corynebacterium jeikeium, Enterococcus faecalis, Enterococcus faecium, Erysipelothrix rhusiopathiae, Gardnerella vaginalis, Gemella morbillorum, Mycobacterium abcessus, Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans*, and *Peptococcus niger.*

In some embodiments, the bacterial infection being treated and/or prevented is an infection caused by a Gram-negative bacterium. Exemplary Gram-negative bacteria include, but are not limited to, *Escherchia coli, Caulobacter crescentus, Pseudomonas, Agrobacterium tumefaciens, Branhamella catarrhalis, Citrobacter diversus, Enterobacter aerogenes, Klebsiella pneumoniae, Proteus mirabilis, Salmonella typhimurium, Neisseria meningitidis, Serratia marcescens, Shigella sonnei, Neisseria gonorrhoeae, Acinetobacter baumannii, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Morganella morganii, Edwardsiella tarda*, and *Haemophilus influenzae*. In certain embodiments, the Gram-negative bacteria species is *Pseudomonas*. In certain embodiments, the Gram-negative bacteria species is *Pseudomonas aeruginosa.*

In some embodiments, the bacterial infection being treated and/or prevented is a urinary tract infection (most commonly caused by *Escherichia coli, Proteus mirabilis*, and/or *Staphylococcus saprophyticus*). In some embodiments, the bacterial infection is a catheter-associated urinary tract infection. In some embodiments, the bacterial infection is gastritis (most commonly caused by *Helicobacter pylori*), respiratory infection (such as those commonly afflicting patents with cystic fibrosis, most commonly caused by *Pseudomonas aeuroginosa*), cystitis (most commonly caused by *Escherichia coli*), pyelonephritis (most commonly caused by *Proteus* species, *Escherichia coli* and/or *Pseudomonas* sp), osteomyelitis (most commonly caused by *Staphylococcus aureus*, but also by *Escherichia coli*), bacteremia, skin infection, rosacea, acne, chronic wound infection, infectious kidney stones (can be caused by *Proteus mirabilis*), bacterial endocarditis, and/or sinus infection.

In some embodiments, the bacterial infection being treated and/or prevented is caused by an organism resistant to one or more antibiotics. For example, in some embodiments, the bacterial infection is caused by an organism resistant to penicillin. In some embodiments, the bacterial infection is caused by an organism resistant to vancomycin (VR). In some embodiments, the bacterial infection is caused by vancomycin-resistant *E. faecalis*. In some embodiments, the bacterial infection is caused by vancomycin-resistant *E. faecium*. In some embodiments, the bacterial infection is caused by vancomycin-resistant *Staphylococcus aureus* (VRSA). In some embodiments, the bacterial infection is caused by vancomycin-resistant Enterococci (VRE). In some embodiments, the bacterial infection is caused by a methicillin-resistant (MR) organism. In some embodiments, the bacterial infection is caused by methicillin-resistant *S. aureus* (MRSA). In some embodiments, the bacterial infection is caused by methicillin-resistant *Staphylococcus epidermidis* (MRSE). In some embodiments, the bacterial infection is caused by penicillin-resistant *Streptococcus pneumonia*. In some embodiments, the bacterial infection is caused by quinolone-resistant *Staphylococcus aureus* (QRSA). In some embodiments, the bacterial infection is caused by multi-drug resistant *Mycobacterium tuberculosis*.

In some embodiments, the subject administered the IdsD protein or pharmaceutical composition as provided herein is a mammal. In some embodiments, the subject is a human. In certain embodiments, the subject is an immunocompromised subject. In some embodiments, the subject is a domesticated animal, such as a dog, cat, cow, pig, horse, sheep, or goat. In some embodiments, the subject is a companion animal such as a dog or cat. In some embodiments, the subject is a livestock animal such as a cow, pig, horse, sheep, or goat. In some embodiments, the subject is a zoo animal. In another embodiment, the subject is an experimental animal such as a rodent or non-human primate.

The IdsD protein or pharmaceutical composition can be administered concurrently with, prior to, or subsequent to, one or more additional therapeutically active agents (e.g., antibiotics, anti-inflammatory agents). In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

In some embodiments, the subject is administered IdsD protein and one or more additional therapeutic agents. In some embodiments, the additional therapeutic agent is an antimicrobial including, but not limited to, an antibiotic, an antifungal, or an antiviral.

Examples of antibiotics include, but are not limited to penicillins, cephalosporins, carbepenems, other beta-lactams antibiotics, aminoglycosides, macrolides, lincosamides, glycopeptides, tetracylines, chloramphenicol, quinolones, fucidins, sulfonamides, trimethoprims, rifamycins, oxalines, streptogramins, lipopeptides, ketolides, polyenes, azoles, and echinocandins.

Examples of antifungals include, but are not limited to, polyene antifungals—natamycin, rimocidin, filipin, nystatin, amphotericin B, candicin, and hamycin; imidazole antifungals—miconazole, ketoconazole, clotrimazole, econazole, omoconazole, bifonazole, butoconazole, fenticonazole, isoconazole, oxiconazole, sertaconazole, sulconazole, and tioconazole; triazole antifungals—fluconazole, itraconazole, isavuconazole, ravuconazole, posaconazole, voriconazole, terconazole, and albaconazole; thiazole antifungals—abafungin; allylamine antifungals—terbinafine, naftifine, and butenafine; and echinocandin antifungals—anidulafungin, caspofungin, and micafungin. Other compounds that have antifungal properties include, but are not limited to polygodial, benzoic acid, ciclopirox, tolnaftate, undecylenic acid, flucytosine or 5-fluorocytosine, griseofulvin, and haloprogin.

Examples of antivirals include, but are not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, Foscarnet, Fomivirsen, Ganciclovir, Indinavir, Idoxuridine, Lamivudine, Lopinavir Maraviroc, MK-2048, Nelfinavir, Nevirapine, Penciclovir, Raltegravir, Rilpivirine, Ritonavir, Saquinavir, Stavudine, Tenofovir Trifluridine, Valaciclovir, Valganciclovir, Vidarabine, Ibacitabine, Amantadine, Oseltamivir, Rimantidine, Tipranavir, Zalcitabine, Zanamivir and Zidovudine.

Kits

A medical device kit comprises a medical device and IdsD protein. In some embodiments, the medical device kit comprises a medical device that is pre-coated with a therapeutically effective amount of IdsD protein. In some embodiments, the medical device kit comprises a medical device and a therapeutically effective amount of IdsD protein that can be coated onto the surface of the medical device by a health care practitioner.

A medical device kit may comprise any suitable form of IdsD protein. In some embodiments, the IdsD protein is recombinant IdsD protein. In some embodiments, the IdsD protein is nucleic acids encoding the IdsD protein. In some embodiments, the IdsD protein is supplied by a bacterial composition that makes and/or secretes the IdsD protein. In some embodiments, the IdsD protein is a pharmaceutical composition.

The present disclosure encompasses a medical device kit comprising any medical device suitable for coating with IdsD protein. Exemplary medical devices include, but are not limited to, catheters such as urinary catheters, venous catheters, arterial catheters, dialysis catheters, peritoneal catheters, urinary sphincters, urinary dilators, urinary stents, tissue bonding urinary devices, vascular grafts, vascular dilators, extravascular dilators, vascular stents, extravascular stents, wound drain tubes, shunts, pacemaker systems, joint replacements, heart valves, cardiac assist valves, bone prosthesis, joint prosthesis, or dental prosthesis.

EXAMPLES

The following Examples are intended to illustrate and to describe particular embodiments, but are not intended to exemplify the full scope of the invention. Accordingly, it will be understood that the Examples are not meant to limit the scope of the invention.

Example 1: Non-Cognate IdsD-IdsE Pairs Cause Restricted Swarm Colony Expansion but not Reduced Viability or Apparent Swarmer Cell Differentiation Swarming colonies of *P. mirabilis* strain BB2000 carrying mutations in the variable regions (VRs) encoded by the ids operon appear unusually small in diameter (31). To investigate effects of Ids-mediated self-recognition on swarm colony expansion, these *P. mirabilis* strains, which are genetically identical except for the VRs in IdsD and IdsE, were utilized. The VRs either originated from wild-type strain BB2000 (VR-BB) or from wild-type strain HI4320 (VR-HI). The ids operon, including the genes for IdsD and IdsE, was maintained on a low-copy number plasmid under control of the native promoter in the/lids strain, which is a BB2000-derived strain lacking the chromosomal copy of the ids locus (2). This complemented Aids strain and its derivatives are the standard tools for studying the Ids system (2, 5, 31).

Figure 6:
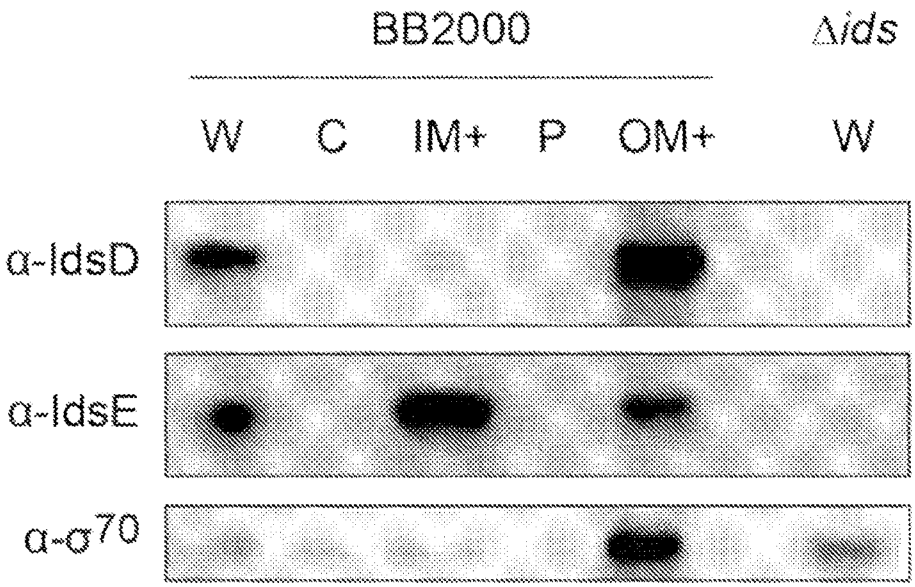
FIG. 6 shows representative western blots of subcellular fractions of swarming BB2000 and of whole cell extract of Aids, probed for the presence of IdsD, IdsE, and $\sigma^{70}$. A band for $\sigma^{70}$ was seen in all fractions. No bands corresponding to IdsD or IdsE were observed in the cytoplasmic fraction. W, whole cell extract; C, cytoplasmic fraction; IM+, inner membrane fraction plus proteins that were not fully solubilized in prior steps; P, periplasm fraction; OM+, outer membrane fraction plus proteins that where not fully solubilized in prior steps.

To determine the cellular locations of IdsD and IdsE, subcellular fractions of swarming BB2000 were prepared and the presence of IdsD, IdsE, and $\sigma^{70}$ was detected by Western blotting. Whole cell extract of Aids was prepared as a control. A band corresponding to $\sigma^{70}$ was seen in all fractions (FIG. 6). No bands corresponding to IdsD or IdsE were observed in the cytoplasmic fraction (FIG. 6). These results indicate that IdsD and IdsE are localized to the cell envelope in *P. mirabilis* strain BB2000.

Figure 1B:
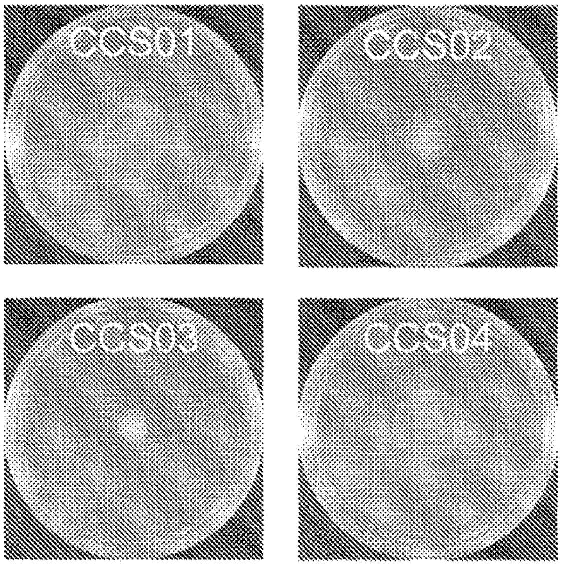
Figure 4:
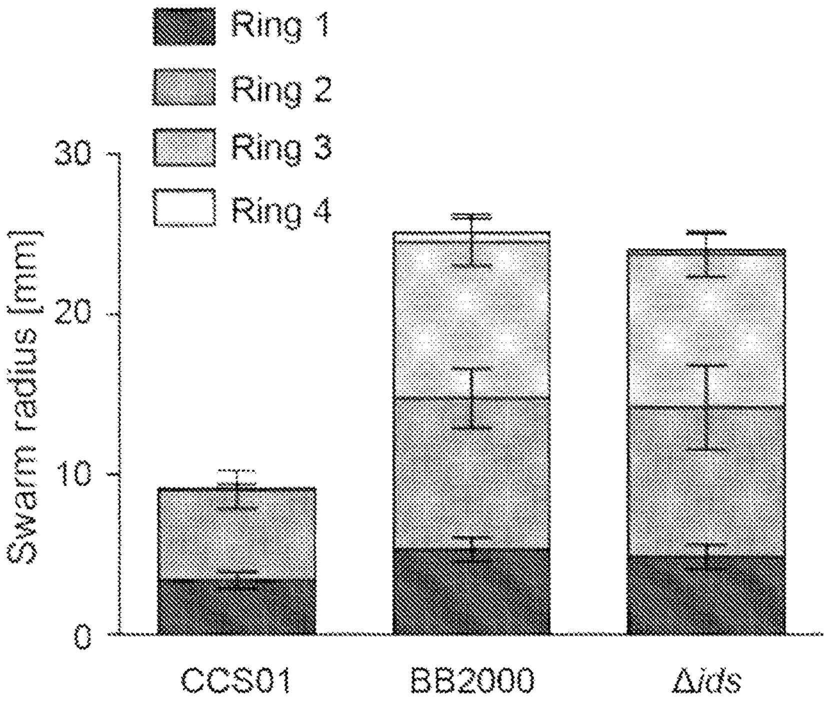
FIG. 4 shows a plot of colony expansion of monoclonal swarms after 16 hours on swarm-permissive agar surfaces. Widths of individual swarm rings within a swarm colony are marked by different shades. N=16, error bars show standard deviations of individual swarm ring widths. Data from strain CCS01 is the same as in FIG. 1A.

After 16 hours on swarm-permissive agar, swarm colonies of a strain producing the cognate $D_{VR\text{-}BB}E_{VR\text{-}BB}$ pair (CCS01) expanded significantly further than swarm colonies of strains producing the non-cognate $D_{VR-HI}E_{VR-BB}$ (CCS02) or $D_{VR-BB}E_{VR-HI}$ (CCS03) pairs (FIG. 1A). In contrast, a strain producing the cognate $D_{VR-HI}E_{VR-HI}$ pair (CCS04) showed recovered swarm expansion (FIG. 1A). Differences in colony expansion persisted even after 24 hours (FIG. 1B). Thus, colony swarm expansion was restricted when non-cognate IdsD and IdsE proteins are present. However, IdsD and IdsE are not essential for swarming (FIG. 4).

Figure 1C:
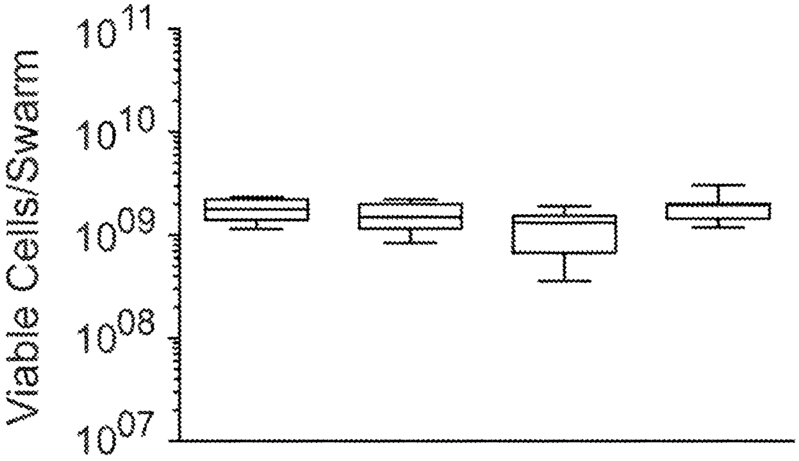
Figure 1D:
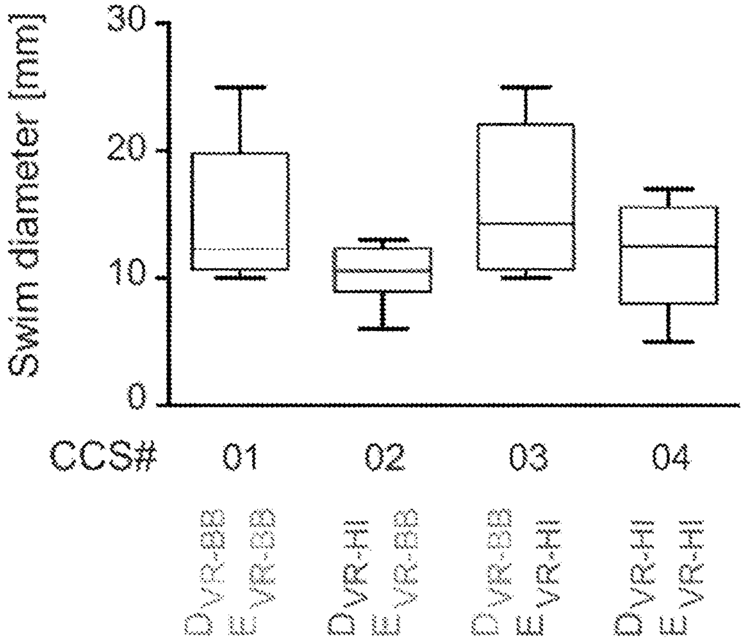
Figure 5A:
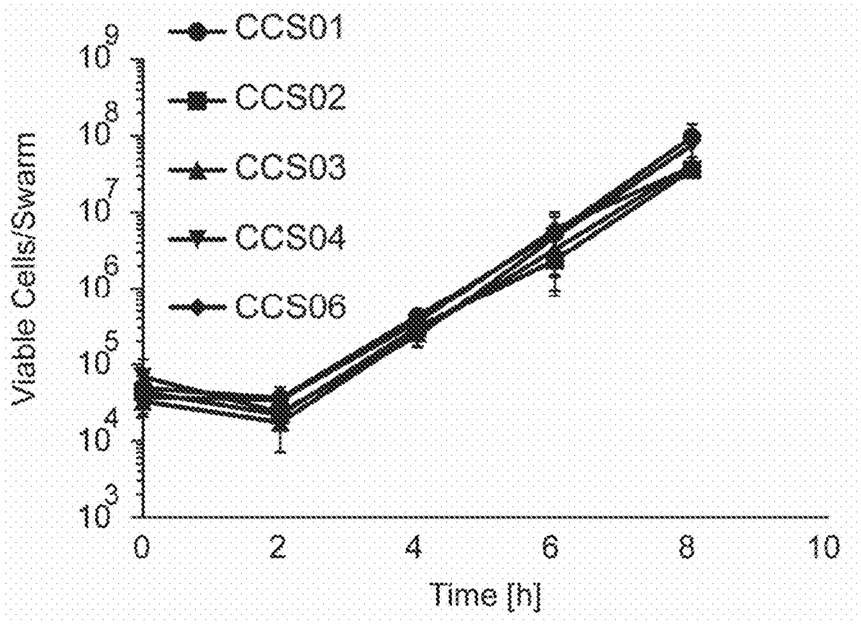
FIG. 5A-5B shows viability on surfaces and generation times in liquid are unaltered when IdsD and IdsE are noncognate.

Whether IdsD and IdsE contained cognate or non-cognate variable regions, however, had no measurable effect on the number of swarm rings per colony (FIG. 1A), on growth on surfaces (FIG. 1C and FIG. 5A), or growth in liquid (FIG. 5B), suggesting that growth and swarm-related developmental cycles were not impaired. No significant differences in colony expansion during swimming in low-percentage agar were observed between any of these strains either (FIG. 1D), and individual cells of all four strains were capable of differentiating into elongated, actively moving swarmer cells (data not shown). Therefore, non-cognate IdsD-IdsE pairs do not appear to inhibit cell viability, swimming motility, or swarm colony development; nevertheless, macroscopic colony swarm expansion was impaired. This stark phenotype may be used to address the outstanding question of how the Ids system communicates identity information between cells within a colony.

Example 2: IdsD Communicates Identity Between Neighboring Cells

Figure 2A:
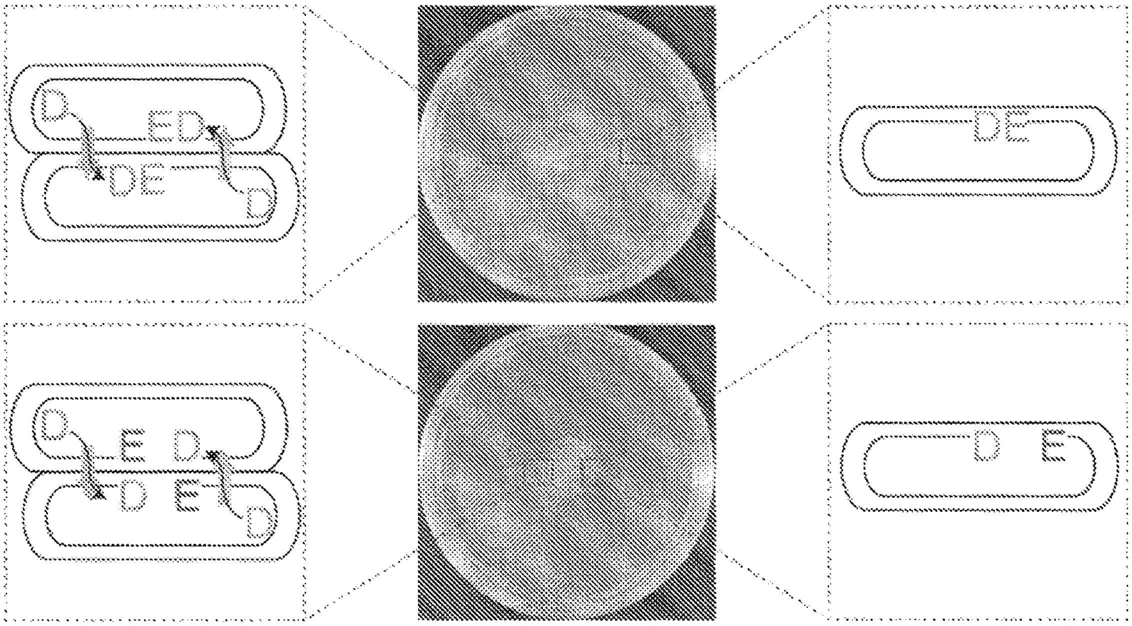
FIG. 2A-2C shows IdsD is transferred between cells.

There are two prevailing mechanistic models for where the causative in vivo interactions between IdsD and IdsE may occur. IdsD and IdsE binding could happen between neighboring cells (FIG. 2A, left panel) or within a single cell (FIG. 2A, right panel). To distinguish between these models, whether IdsD export is necessary for its function was examined. The Δids-derived strain deficient in T6SS-mediated transport (CCS05) was used. CCS05 carries a mutation in vipA; the encoded protein, VipA [T6SS_VipA (PF05591)], is essential for export of T6SS-related factors (11, 33, 34). To confirm loss of T6SS mediated transport, IdsA [T6SS_Hcp (PF05638)] carrying a C-terminal FLAG epitope tag (5) was introduced into CCS05. Export of Hcp homologs, such as IdsA, is a hallmark of T6SS dependent protein transport and has often been used to evaluate T6SS activity (5, 8, 9, 11, 26, 35). Further, the export of IdsD is dependent on a functional T6SS and is correlated with IdsA export (5).

Figure 2B:
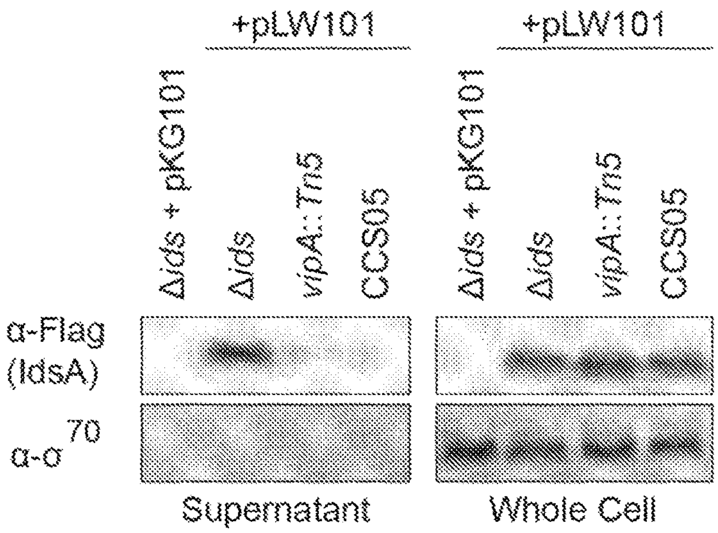

The export of IdsA-FLAG from the CCS05-derived strain was markedly decreased as compared to that from the otherwise genetically equivalent strain expressing wild-type vipA (FIG. 2B). Supernatants isolated from these strains were analyzed by LC-MS/MS. Peptides corresponding to IdsB and IdsD were absent in the CCS05-derived strain expressing mutant vipA and found in the Δids mutant-derived strain expressing wild-type vipA (Table 1). These results indicate that CCS05 is deficient in T6SS-mediated export, including the loss of IdsA, IdsB, and IdsD transport.

TABLE 1

LC-MS/MS results for supernatant fractions, from ~70 to 150 kDa.

| Strain | Protein | Predicted size (kDa) | No. of unique peptides | No. of total peptides | Coverage (%) |
|---|---|---|---|---|---|
| Δids strain | $\sigma^{70}$ | 71.11 | 3 | 3 | 4.05 |
| carrying pLMW101 | IdsB | 81.55 | 5 | 5 | 10.65 |
| (export active) | IdsD | 118.16 | 2 | 6 | 2.32 |
| CCS05 carrying pLMW101 (export inactive) | $\sigma^{70}$ | 71.11 | 2 | 2 | 2.91 |

Figure 2C:
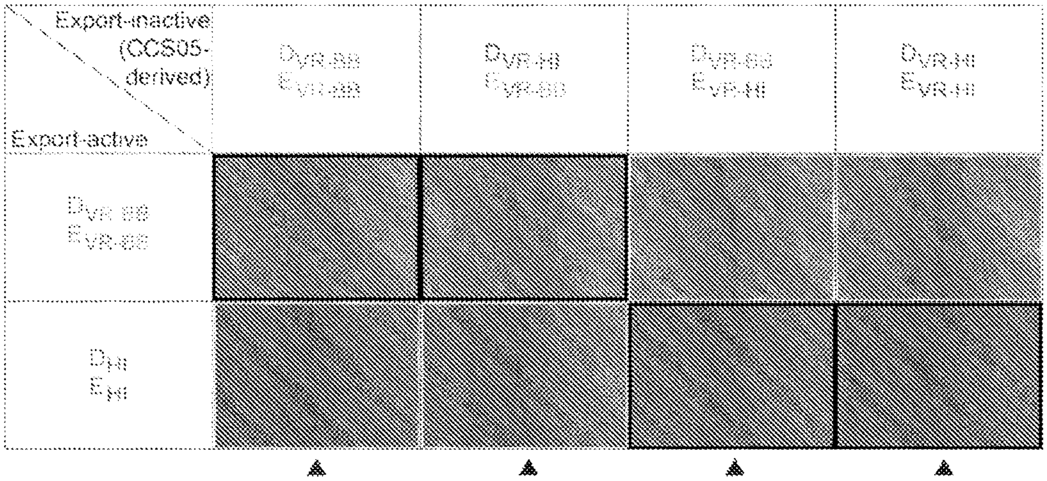

CCS05-derived strains expressing different combinations of IdsD and IdsE variants, were utilized as indicator strains to determine whether IdsD is received from a neighboring cell. Boundary formation phenotypes were determined of these CCS05-derived strains when swarmed against Δids-derived (export-active donor) strains that produced IdsD and IdsE proteins either from strain BB2000 ($D_{VR-BB}E_{VR-BB}$) or from strain HI4320 ($D_{HI}E_{HI}$). These two export active strains form a boundary against each other and are non-self (31). Swarming populations of the CCS05-derived strains producing $E_{VR-BB}$ (and either $D_{VR-BB}$ or $D_{VR-HI}$) merged with the donor strain producing $D_{VR-BB}E_{VR-BB}$ and not with the donor strain producing $D_{HI}E_{HI}$ (FIG. 2C). Conversely, CCS05-derived strains producing $E_{VR-HI}$ (and either $D_{VR-BB}$ or $D_{VR-HI}$) merged with the donor strain producing $D_{HI}E_{HI}$ (FIG. 2C). In all cases, the IdsD variant produced by the CCS05-derived, export-inactive strain did not affect the outcome (FIG. 2C). Thus, the identities of the IdsD variant in the donor strain and of the IdsE variant in the export-inactive CCS05-derived strain correlated with whether populations merged or formed a boundary.

Given these data, the observed impairment in swarm colony expansion of CCS02 and CCS03, which are the strains producing non-cognate IdsD and IdsE proteins (FIG. 1A), could be explained by the presence of unbound IdsD in recipient cells (FIG. 2A, left panel). If so, then a similar defect would be expected for strains lacking IdsE since, in a clonal population, every cell could export as well as receive IdsD and would have no IdsE to bind it. Therefore, a Δids-derived strain complemented with an ids operon that lacks the gene encoding IdsE (CCS06) was constructed to test this hypothesis.

Figure 3A:
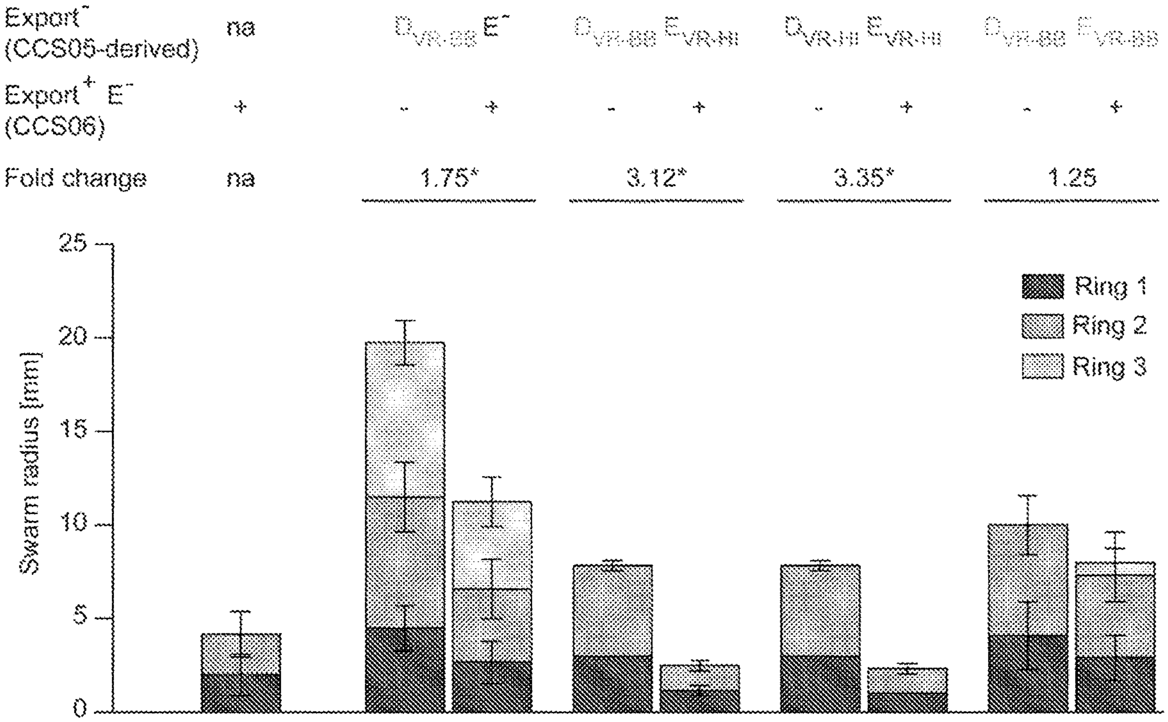
FIG. 3A-3B shows unbound IdsD in a recipient cell impairs swarm colony expansion.
Figure 5B:
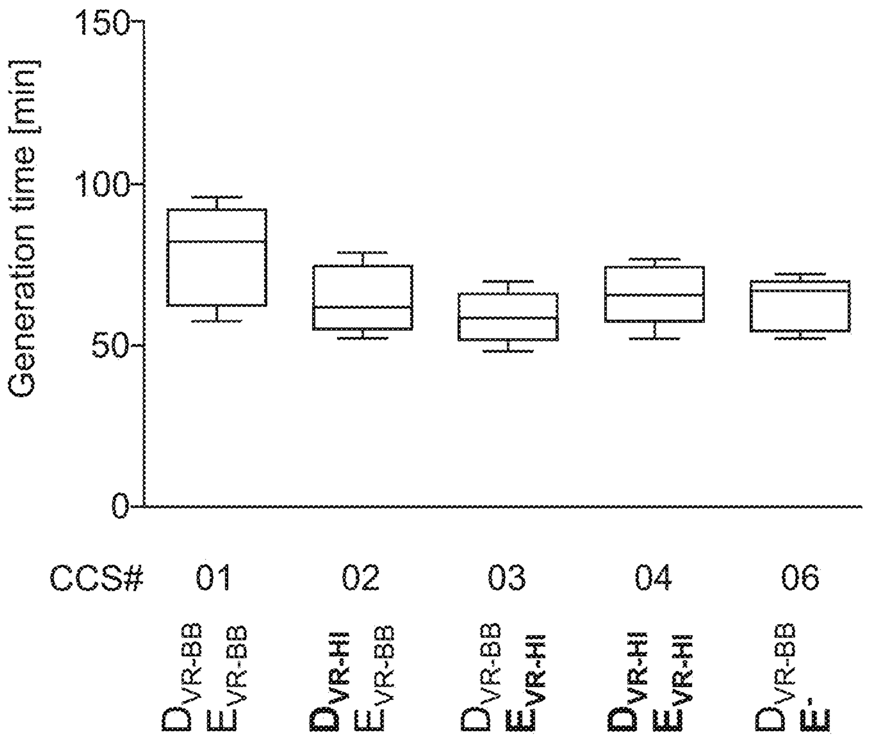

CCS06 swarms displayed colony expansion similar to that of CCS02 and CCS03 (FIG. 3A). CCS06 did not exhibit defects in swarm rings per colony (FIG. 3A), growth on surfaces (FIG. 5A), or growth in liquid (FIG. 5B). Therefore, the presence of unbound IdsD indeed impaired swarm colony expansion.

The question remained, however, whether IdsD exchange between cells is crucial for this swarm inhibition or whether unbound, self-produced IdsD could also affect self-recognition behaviors. Therefore, the swarm colony expansion of export-inactive, CCS05-derived cells lacking IdsE was examined. In this strain, cells contain self-produced IdsD but cannot export IdsD, i.e., cells do not contain a transferred IdsD. This strain exhibited a rescued swarm colony expansion phenotype (FIG. 3A). Together these results support the hypothesis that IdsD is exported and that it is transferred between cells (FIG. 2A, left panel). Moreover, transferred, unbound IdsD in recipient cells, rather than self-produced IdsD, appears to impair swarm colony expansion.

Example 3: Interactions Between Transferred IdsD and Resident IdsE Impact Swarm Colony Expansion It was hypothesized that the transfer of IdsD might be sufficient to induce impaired swarm colony expansion. This hypothesis was interrogated by examining the swarm colony expansion of 1:1 mixtures of two strains, resulting in co-swarms. Strain CCS06 (lacking IdsE) was co-swarmed with the nearly isogenic CCS05-derived recipient strain lacking both IdsE and a functional T6SS. A 1.75-fold decrease in expansion of the co-swarm colony as compared to that of a monoculture swarm of the recipient strain (FIG. 3A) was observed. These results indicate that transfer of IdsD to recipient cells restricted swarm colony expansion.

Figure 3B:
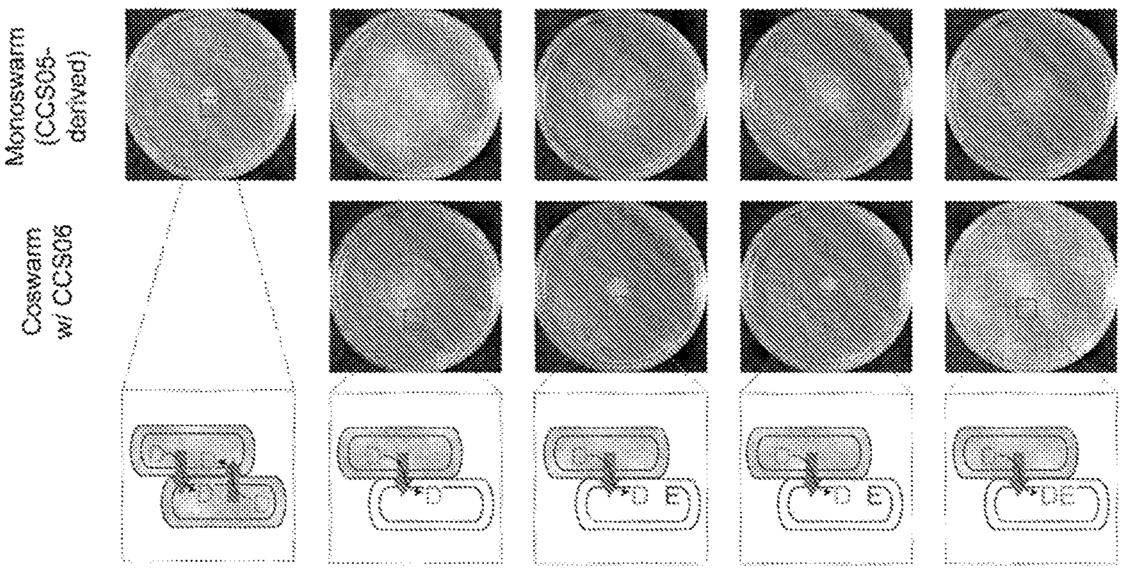

It was further hypothesized that transfer of IdsD and its resulting binding state with IdsE in the recipient cell determines whether swarm colony expansion is restricted or not. Therefore, CCS06 as a donor of $D_{VR-BB}$ was used in 1:1 mixtures with CCS05-derived (export-inactive recipient) strains that produced either $E_{VR-BB}$, which binds $D_{VR-BB}$, or $E_{VR-HI}$, which cannot bind $D_{VR-BB}$. All co-swarms were compared to monoculture swarms of the recipient strain. In coswarms of CCS06 with the recipient strain producing $D_{VR-BB}$ and $E_{VR-HI}$, a 3.12-fold reduction was observed (FIGS. 3A-3B). Likewise, a coswarm of CCS06 with the recipient strain producing $D_{VR-HI}$ and $E_{VR-HI}$ resulted in a 3.35-fold reduction in colony expansion (FIGS. 3A-3B). By contrast, mixing CCS06 with the recipient strain producing $D_{VR-BB}$ and $E_{VR-BB}$ resulted in a non-significant reduction in colony expansion (FIGS. 3A-3B). In sum, no restriction appeared when the IdsE variant in the recipient strain is capable of binding $D_{VR-BB}$ from the donor strain. However, we observed a ~2-3 fold restriction in swarm colony expansion when IdsE in the recipient strain is non-cognate to $D_{VR-BB}$. Thus, communication of IdsD from a donor to a recipient cell causes restricted swarm colony expansion. Alleviation of this swarm restriction can be achieved by the presence of a cognate IdsE in the recipient cell.

During the course of observing monoclonal swarms, it was unexpectedly noticed that the production of IdsE in recipient strains, regardless of whether a cognate IdsD was produced, resulted in a marked decrease of colony expansion (average=2.3-fold) as compared to that for an otherwise identical strain that lacked IdsE (FIG. 3A). These results raise the possibility that independently of IdsD, IdsE itself contributes to repression of swarm colony expansion.

Discussion.

Disclosed herein are results that address unresolved questions regarding the communication of Ids proteins within a colony of swarming *P. mirabilis*. The results provided herein have shown that the self-identity protein IdsD is communicated from one cell to another. Also provided herein is evidence that IdsD from donor cells likely interacts with IdsE in recipient cells and that lack of this interaction negatively impacts swarm colony expansion, but not viability. Therefore, IdsD might represent a class of non-lethal T6SS effector proteins.

Based on the prominent T6SS models for effector/inhibitor pairs, it was expected that unbound IdsD, whether in donor or recipient cells, should suffice to act as an effector. However, this was not strictly observed since unbound IdsD was only active in recipient cells. We hypothesize that one or more proteins in the donor cell might act to sequester IdsD. Alternatively, or in addition to, IdsD might not be in a folded or active state in the donor cell. Even more surprisingly, the presence of IdsE in export-impaired cells appeared to have an inhibitory effect on colony expansion (FIG. 3A). Together our observations suggest that IdsD and IdsE regulate swarm colony expansion. However, the specific molecular mechanisms remain to be determined.

It is a bit perplexing that IdsD is indeed communicated between cells in a T6SS-dependent manner as IdsD is over 100 kDa in size and contains two predicted transmembrane segments (31). Many T6SS-exported effectors are under 50 kDa, and the inner Hcp tube comprising the channel of many T6SSs has a width of 40 Å in multiple bacteria (8, 36-38). In fact, a variety of T6SS effectors bind to the inside of the Hcp tube allowing them to be exported (35). The size of the *P. mirabilis* T6SS pore has not been directly measured. However given IdsD's large size, IdsD might be communicated via the T6SS by an alternative mechanism. For example, IdsD might be exported out of the donor cell in an unfolded state and then fold into its active state before or after being received by the recipient cell. This would be consistent with the observation that IdsD transfer is required for its activity (FIG. 3A). Clearly, the macromolecular states of IdsD before, during, and after transfer remain to be resolved to explain this transfer.

Microbial communities frequently exhibit cell-to-cell communication, in many cases involving the exchange of information about kin group identity. Self versus non-self recognition allows that certain group behaviors primarily occur between closely related individuals and/or exclude non-kin cells from shared resources. Many of the mechanisms for the exchange of kin group identity can be distinguished based on their contact-dependency or effects on viability. Quorum sensing by which groups of bacteria can roughly assess cell population density is an example of contact-independent recognition. In this case, kin group identity information is encoded by the molecular structure of the quorum sensing molecule and its ability to bind its protein receptor (39-42). However, as quorum sensing molecules are often diffusible across membranes (43, 44), recognition events do not require physical contact between cells and can occur over greater spatial distances than contact-dependent mechanisms.

By contrast, contact-dependent interactions are local. These recognition events usually require cell-to-cell contact and can involve lethal attacks on non-kin members of the community. For example, contact-dependent killing mechanisms have been described for antagonistic interactions between species and even genera, e.g., T6SS-associated killing (8-10, 13, 14, 16-20, 27, 28), and within a species, e.g., contact-dependent inhibition (CDI) (45-52). From a competition perspective this could be beneficial because when susceptible competitor cells are inhibited, fewer cells will compete for resources like nutrients. However, the existence of contact dependent recognition that does not involve killing, such as demonstrated here for the self-identity proteins IdsD and IdsE, suggests that there is likely a fitness and competitive advantage to recognizing cells of the same kin group. For *P. mirabilis*, swarm expansion of the colony involves intimate interactions between individual cells (53), and so cooperation might be essential for long-range motility. One purpose of the Ids system, and specifically of the self-identity proteins, IdsD and IdsE, might be to restrict cooperative motility behavior to kin cells. As such, the transfer of IdsD and its subsequent interactions with IdsE may represent an additional form of cell-cell communication within a bacterial population.

Materials and Methods

Bacterial Strains and Media.

All strains and plasmids are described in the supplemental material (see Table 2). *P. mirabilis* strains were maintained on $LSW^-$ agar (54). CM55 blood agar base agar (Oxoid, Basingstoke, England) was used for swarm-permissive nutrient plates. Overnight cultures of all strains were grown in LB broth under aerobic conditions at 37° C. Kanamycin was used at a concentration of 35 μg/ml for plasmid maintenance and was added to all swarm and growth media.

We employed a previously published ids expression system (2) in which the entire ids locus from *P. mirabilis* strain BB2000 is expressed from a low-copy number plasmid under control of its native promoter (pIdsBB) in a BB2000-derived strain lacking the chromosomal copy of the ids operon (Δids) (2). We engineered alterations to the ids locus on the vector; hence, all strains are isogenic except for the encoded ids genes.

TABLE 2

Strains used in this disclosure.

| Strain | Name | Description | Source | Notes |
|---|---|---|---|---|
| *Proteus mirabilis* | | | | |
| BB2000 | | Produces the cognate $D_{VR\text{-}BB}E_{VR\text{-}BB}$ pair from a single allele | (59) | Wildtype |
| BB2000::Δids | Δids | | (55) | Δids::Tn-Cm(R) |
| Δids c. pIdsBB | CCS01 | Δids producing the cognate $D_{VR\text{-}BB}E_{VR\text{-}BB}$ pair | (55) | Δids::Tn-Cm(R) carrying plasmid pIdsBB containing the entire BB2000 ids operon (idsA-F) under control of its native promoter. This is strain Δids c. $pids_{BB2000}$ in (1) |
| Δids c. pIdsBB-$D_{VR\text{-}HI}$-$E_{VR\text{-}BB}$ | CCS02 | Δids producing the non-cognate $D_{VR\text{-}HI}E_{VR\text{-}BB}$ pair | (60) | Δids::Tn-Cm(R) carrying a derivative of pIdsBB in which the sequence encoding amino acids 761-865 of IdsD has been replaced with the equivalent sequence of idsD from strain HI4320 |
| Δids c. pIdsBB-$D_{VR\text{-}HI}$-$E_{VR\text{-}BB}$ | CCS03 | Δids producing the non-cognate $D_{VR\text{-}HI}E_{VR\text{-}BB}$ pair | (60) | Δids::Tn-Cm(R) carrying a derivative of pIdsBB in which the sequence encoding amino acids 147-169 from IdsE has been replaced with the equivalent sequence of idsE from strain HI4320 |
| Δids c. pIdsBB-$D_{VR\text{-}HI}$-$E_{VR\text{-}BB}$ | CCS04 | Δids producing the cognate $D_{VR\text{-}HI}E_{VR\text{-}BB}$ pair | (60) | Δids::Tn-Cm(R) carrying a derivative of pIdsBB in which the sequences encoding amino acids 761-865 from IdsD and 147-169 from IdsE have been replaced with the equivalent sequences of idsD and idsE, respectively, from strain HI4320. This is vector $pIds_{BB\text{-}idsD\text{-}BB\ to\ HI\text{-}idsE\text{-}BB\ to\ HI}$ in (6) |
| Δids c. pIdsBB-E-mt | | | (55) | Δids::Tn-Cm(R) carrying a derivative of pIdsBB in which the 102 bp SacI-AgeI fragment of idsE has been replaced by a 467 bp SacIAgeI fragment from pBBR1MCS-2 causing a frame-shift and premature stop codon at codon position 50. This strain was used to identify suppressor mutants of the impaired colony expansion phenotype. This is strain $E^-$ in (1) |
| Δids c. pKG101 | | | (61) | Δids::Tn-Cm(R) carrying plasmid pKG101, which encodes promoterless gfp |
| Δids c. pLW101 | | | (62) | Δids::Tn-Cm(R) carrying a derivative of pIdsBB in which a FLAG epitope (N-DYKDDDDK-C) was inserted immediately before the idsA stop codon |
| vipA::Tn5 c. pLW101 | | | (62) | vipA::Tn5-Cm(R) carrying pLW101. vipA::Tn5-Cm(R) is strain tssA* in (8) |
| BB2000::Δids, $vipA_{T95G}$ | CCS05 | Δids-derived strain that is deficient in T6SS mediated transport | Disclosed herein | BB2000::Δids::Tn-Cm(R), $vipA_{T95G}$ |
| CCS05 c. pLW101 | | | Disclosed herein | Δids::Tn-Cm(R), $vipA_{T95G}$ carrying pLW101 |
| Δids c. pIdsHI | | | (60) | Δids::Tn-Cm(R) carrying plasmid pIdsHI containing the entire HI4320 ids operon (idsA-F) under control of its native promoter |

TABLE 2-continued

| Strains used in this disclosure. | | | | |
|---|---|---|---|---|
| Strain | Name | Description | Source | Notes |
| CCS05 c. pIdsBB | | | Disclosed herein | Δids::Tn-Cm(R), $vipA_{T95G}$ carrying pIdsBB |
| CCS05 c. pIdsBB-$D_{VR-HI}$-$E_{VR-BB}$ | | | Disclosed herein | Δids::Tn-Cm(R), $vipA_{T95G}$ carrying pIdsBB-$D_{VR-HI}$-$E_{VR-BB}$ |
| CCS05 c. pIdsBB-$D_{VR-BB}$-$E_{VR-HI}$ | | | Disclosed herein | Δids::Tn-Cm(R), $vipA_{T95G}$ carrying pIdsBB-$D_{VR-BB}$-$E_{VR-HI}$ |
| CCS05 c. pIdsBB-$D_{VR-HI}$-$E_{VR-HI}$ | | | Disclosed herein | Δids::Tn-Cm(R), $vipA_{T95G}$ carrying pIdsBB-$D_{VR-HI}$-$E_{VR-HI}$ |
| Δids c. pIdsBB-ΔE | CCS06 | Δids (export active) cells producing $D_{VR-BB}$ and not E | Disclosed herein | Δids::Tn-Cm(R) carrying a derivative of pIdsBB in which all of idsE has been deleted leaving only the RBS for idsF |
| CCS05 c. pIdsBB-ΔE | | CCS05 (export inactive) cells producing $D_{VR-BB}$ and not E | Disclosed herein | Δids::Tn-Cm(R), $vipA_{T95G}$ carrying pIdsBB-ΔE |
| *Escherichia coli* | | | | |
| S17λpir | | | (63) | Mating strain for moving plasmids from *E. coli* into *P. mirabilis* |
| SM10λpir | | | (57) | Mating strain for moving suicide vector pKNG101 into *P. mirabilis* |

Colony Expansion and Coswarm Assays and Viable Cell Counts.

Overnight cultures were normalized to $OD_{600}$ 0.1 and swarm-permissive nutrient plates supplemented with kanamycin were inoculated with 1 microliter of normalized culture. Plates were incubated at 37° C. for 16 hours, and radii of actively migrating swarms were measured. Additionally, widths of individual swarm rings within the swarm colonies were recorded. For coswarm assays, strains were processed as described and mixed at a ratio of 1:1 where indicated. For viable cell counts after 16 hours, actively migrating swarms were resuspended in 6 milliliters of LB medium and 20 microliters of the cell suspension were used for a 10-fold dilution series. A total of 8 dilutions were prepared for each sample and 10 microliters of each dilution were spotted onto $LSW^-$ agar supplemented with kanamycin. The dilutions with countable numbers of colonies were used to determine viable cell counts of swarm colonies.

Swimming Assay.

Overnight cultures were normalized to $OD_{600}$ 0.1. An inoculation needle was used to inoculate 0.3% LB nutrient plates supplemented with kanamycin. Plates were incubated at 37° C. for 9 hours and diameters of swim colonies were measured.

Trichloroacetic Acid Precipitations, SDS-PAGE, and Western Blots.

Trichloroacetic acid precipitations were performed as previously described (5). Samples were normalized according to $OD_{600}$ of the liquid cultures at collection, separated by gel electrophoresis using 12% Tris-tricine polyacrylamide gels, transferred onto 0.45-μm nitrocellulose membranes, and probed with monoclonal rabbit-α-FLAG (Sigma-Aldrich, St. Louis, Mo.) and mouse-α-$\sigma^{70}$ primary antibodies (Thermo Fisher Scientific, Waltham, Mass.), followed by polyclonal goat-α-rabbit (KPL, Inc., Gaithersburg, Md.) and goat-α-mouse secondary antibodies (KPL, Inc., Gaithersburg, Md.), respectively. Membranes were developed with the Immun-Star HRP Substrate Kit (Bio-Rad Laboratories, Hercules, Calif.) and visualized using a Chemidoc (Bio-Rad Laboratories, Hercules, Calif.). TIFF images were exported and figures were made in Adobe Illustrator (Adobe Systems, San Jose, Calif.).

Boundary Assays.

Boundary assays were conducted as previously reported (5). Assays were carried out using swarm-permissive agar plates supplemented with kanamycin.

Plasmid and Strain Construction.

Construction of pIdsBB-ΔE. The pIdsBB-ΔE plasmid was constructed using a 390-basepair (bp) gBlock (Integrated DNA Technologies, Inc., Coralville, Iowa) containing the last 266 bp of idsD, the last 18 bp of idsE and the first 106 bp of idsF. EcoNI and KpnI restriction sites within this fragment were used to replace the sequence between EcoNI and KpnI in pIdsBB (55). Ligations were transformed into One Shot® OmniMax™ 2 T1® chemically competent *Escherichia coli* (Thermo Fisher Scientific, Waltham, Mass.).

Construction of the vipA mutation. A swarm-capable, spontaneous mutant strain of the BB2000-derived strain lacking full-length E (55) was isolated. This isolate was subjected to phenol-chloroform extractions to isolate genomic DNA (gDNA). gDNA was sheared using a Covaris S 220 (Covaris, Woburn, Mass.), and a library for whole genome sequencing was prepared using the PrepX ILM DNA Library Kit (WaferGen Biosystems, Fremont, Calif.) for the Apollo 324 NGS Library Prep System (WaferGen Biosystems, Fremont, Calif.). The library was sequenced as 100-bp, paired-end reads using an Illumina HiSeq 2500 system (Illumina, San Diego, Calif.). Reads were aligned to the *P. mirabilis* BB2000 genome (Accession number is CP004022) using Geneious (Biomatters, Auckland, New Zealand). Suppressor-specific polymorphisms were identified by aligning the assembled genome to that of the ancestral strain, BB2000::Δids. The identified mutation mapped to a gene encoding a vipA homolog [T6SS_VipA (PF05591))]. BB2000::Δlids, $vipA_{T95G}$ was then constructed by amplifying a DNA fragment using the pCS34 Forward and Reverse primers (Table 3) from gDNA of the isolated spontaneous mutant strain. Restriction digestion with ApaI and XbaI was used to introduce this sequence into the suicide vector pKNG101 (56). The resulting vector pCS34 was introduced into mating strain *E. coli* SM10λpir (57) and then mated into BB2000::Δids. Matings were subjected to antibiotic selection on $LSW^-$ agar (15 μm/ml tetracycline and 25 μm/ml streptomycin). Candidate strains were subjected to sucrose counter-selection as previously described (58). Double-recombinants were confirmed using whole genome sequencing as described above. The Bauer Core Facility at Harvard University performed all sequencing.

Phase Contrast Microscopy.

1-mm thick swarm-permissive agar pads supplemented with kanamycin were inoculated from overnight cultures. The agar pads were incubated at 37° C. in a modified humidity chamber. After 5 hours, the pads were imaged by phase contrast microscopy using a Leica DM5500B (Leica Microsystems, Buffalo Grove, Ill.) and a CoolSnap $HQ^2$ cooled CCD camera (Photometrics, Tucson, Ariz.). MetaMorph version 7.8.0.0 (Molecular Devices, Sunnyvale, Calif.) was used for image acquisition. Images were acquired every 2 seconds for 78 seconds. Image stacks were imported into Fiji (ImageJ 1.48s) (64-67) where the image stacks were cropped to show a segment of cells, combined into a single movie from four individual movies, and converted to an .AVI file with a frame rate of 5 frames per second.

TABLE 3

DNA sequence inserts and primers for plasmids constructed in this disclosure.

| Plasmid | DNA insert/amplified product | gBlock gene fragment/primer pair (5'-3') |
|---|---|---|
| pIdsBB-ΔE | gBlock gene fragment containing the last 266 bp of idsD, the last 18 bp of idsE and the first 106 bp of idsF. EcoNI and KpnI restriction sites flanking this fragment were used for cloning into pIdsBB (55). | gBlock gene fragment: GCGAACAATTAAAAATGGCAAG TGAAAAAGGTGATTGGAACCCT GAAACAGGTATATTTAAATTTA GTTTGGAAGTACAGTCTCAATTA GTAAATACATATTCTGCTTTTGG TGCACATCCTAATAGCCGTATA GGTATTGAAGATTTATATTGGTA TTATCAAGTCAATCCCGAGGTA ACAACACCGATGCGTTATATCA ATTGGGGGGGAGATACCCAAGA AAACAATCAGCTTTTAGGCTTTA TTAACAGTGAGAATATCTAAAT CAGGAGAAAGAACACCATGCGT AGTTTGGTAAACGGCAGAAAGA TTATTTTAGAAAATGATACAAC AAATACCGGCGGTACCGTACTT ACCGGCTCTTCTATTGCTAAACA AACACAAGGGG (SEQ ID NO: 17) |
| pCS34 | DNA fragment containing vipA as well as the 939 bp upstream and the 851 bp downstream regions were amplified from genomic DNA of the original suppressor mutant containing $vipA_{T95G}$ | Forward primer: CGCGGGCCCGGTATTACCCCAT AAATAGTGC (SEQ ID NO:18)<br><br>Reverse primer: CAGCTATATTTGGTTTAACTTAA GGTCTAGAGCGCGC (SEQ ID NO: 19) |

Viable Cell Counts.

Overnight cultures were normalized to $OD_{600}$ 0.1, and swarm-permissive nutrient plates containing 35 μg/ml kanamycin were inoculated with 1 microliter normalized culture. Plates were incubated at 37° C. Viable cell counts at time point 0 were determined by preparing a 10-fold dilution series of the normalized overnight cultures and spotting 10 microliters of each dilution on $LSW^-$ agar plates supplemented with kanamycin. Viable cell counts at time points 2, 4, 6 and 8 hours post-inoculation were determined by resuspending swarm colonies in 1 milliliter LB medium and preparing 10-fold dilution series. 10 microliters of each dilution were spotted onto $LSW^-$ agar supplemented with kanamycin. Dilutions with countable numbers of colonies were used to determine viable cell counts of swarm colonies.

Measuring Generation Times.

Overnight cultures were normalized to $OD_{600}$ 0.1 in LB medium supplemented with kanamycin. Normalized cultures were grown overnight at 37° C. shaking periodically in a Tecan Infinite® 200 PRO microplate reader (Tecan, Männedorf, Switzerland). Generation times were calculated from log-phase growth measurements.

REFERENCES

1. Budding A E, Ingham C J, Bitter W, Vandenbroucke-Grauls C M, Schneeberger P M. 2009. The Dienes phenomenon: competition and territoriality in swarming *Proteus mirabilis*. J Bacteriol 191:3892-3900.
2. Gibbs K A, Urbanowski M L, Greenberg E P. 2008. Genetic determinants of self-identity and social recognition in bacteria. Science 321:256-259.
3. Senior B W. 1977. The Dienes phenomenon: identification of the determinants of compatibility. J Gen Microbiol 102:235-244.
4. Dienes L. 1947. Further observations on the reproduction of bacilli from large bodies in *Proteus* cultures. Proc Soc Exp Biol Med 66:97-98.

5. Wenren L M, Sullivan N L, Cardarelli L, Septer A N, Gibbs K A. 2013. Two independent pathways for self-recognition in *Proteus mirabilis* are linked by type VI-dependent export. mBio 4.
6. Gibbs K A, Wenren L M, Greenberg E P. 2011. Identity gene expression in *Proteus mirabilis*. J Bacteriol 193: 3286-3292.
7. Alteri C J, Himpsl S D, Pickens S R, Lindner J R, Zora J S, Miller J E, Arno P D, Straight S W, Mobley H L. 2013. Multicellular bacteria deploy the type VI secretion system to preemptively strike neighboring cells. PLoS Pathog 9:e1003608.
8. Mougous J D, Cuff M E, Raunser S, Shen A, Zhou M, Gifford C A, Goodman A L, Joachimiak G, Ordonez C L, Lory S, Walz T, Joachimiak A, Mekalanos J J. 2006. A virulence locus of *Pseudomonas aeruginosa* encodes a protein secretion apparatus. Science 312:1526-1530.
9. Pukatzki S, Ma A T, Sturtevant D, Krastins B, Sarracino 317 D, Nelson W C, Heidelberg J F, Mekalanos J J. 2006. Identification of a conserved bacterial protein secretion system in *Vibrio cholerae* using the Dictyostelium host model system. Proc Natl Acad Sci USA 103:1528-1533.
10. Pukatzki S, Ma A T, Revel A T, Sturtevant D, Mekalanos J J. 2007. Type VI secretion system translocates a phage tail spike-like protein into target cells where it cross-links actin. Proc Natl Acad Sci USA 104:15508-15513.
11. Basler M, Pilhofer M, Henderson G P, Jensen G J, Mekalanos J J. 2012. Type VI secretion requires a dynamic contractile phage tail-like structure. Nature 483: 182-186.
12. Basler M, Mekalanos J J. 2012. Type 6 secretion dynamics within and between bacterial cells. Science 337:815.
13. Basler M, Ho B T, Mekalanos J J. 2013. Tit-for-tat: type VI secretion system counterattack during bacterial cell-cell interactions. Cell 152:884-894.
14. Shneider M M, Buth S A, Ho B T, Basler M, Mekalanos J J, Leiman P G. 2013. PAAR330 repeat proteins sharpen and diversify the type VI secretion system spike. Nature 500:350-353.
15. Hood R D, Singh P, Hsu F, Guvener T, Carl M A, Trinidad R R, Silverman J M, Ohlson B B, Hicks K G, Plemel R L, Li M, Schwarz S, Wang W Y, Merz A J, Goodlett D R, Mougous J D. 2010. A type VI secretion system of *Pseudomonas aeruginosa* targets a toxin to bacteria. Cell Host Microbe 7:25-37.
16. Russell A B, Hood R D, Bui N K, LeRoux M, Vollmer W, Mougous J D. 2011. Type VI secretion delivers bacteriolytic effectors to target cells. Nature 475:343-347.
17. Russell A B, LeRoux M, Hathazi K, Agnello D M, Ishikawa T, Wiggins P A, Wai S N, Mougous J D. 2013. Diverse type VI secretion phospholipases are functionally plastic antibacterial effectors. Nature 496:508-512.
18. Whitney J C, Chou S, Russell A B, Biboy J, Gardiner 340 T E, Ferrin M A, Brittnacher M, Vollmer W, Mougous J D. 2013. Identification, structure, and function of a novel type VI secretion peptidoglycan glycoside hydrolase effector-immunity pair. J Biol Chem 288:26616-26624.
19. MacIntyre D L, Miyata S T, Kitaoka M, Pukatzki S. 2010. The *Vibrio cholerae* type VI secretion system displays antimicrobial properties. Proc Natl Acad Sci USA 107:19520-19524.
20. Miyata S T, Kitaoka M, Brooks T M, McAuley S B, Pukatzki S. 2011. *Vibrio cholera* requires the type VI secretion system virulence factor VasX to kill Dictyostelium discoideum. Inf Imm 79:2941-2949.
21. Brooks T M, Unterweger D, Bachmann V, Kostiuk B, Pukatzki S. 2013. Lytic activity of the *Vibrio cholerae* type VI secretion toxin VgrG-3 is inhibited by the antitoxin TsaB. J Biol Chem 288:7618-7625.
22. Unterweger D, Miyata S T, Bachmann V, Brooks T M, Mullins T, Kostiuk B, Provenzano D, Pukatzki S 2014. The *Vibrio cholerae* type VI secretion system employs diverse effector modules for intraspecific competition. Nature Comm 5:3549.
23. Durand E, Derrez E, Audoly G, Spinelli S, Ortiz-Lombardia M, Raoult D, Cascales E, Cambillau C. 2012. Crystal structure of the VgrG1 actin cross-linking domain of the *Vibrio cholerae* type VI secretion system. J Biol Chem 287:38190-38199.
24. Brunet Y R, Espinosa L, Harchouni S, Mignot T, Cascales E. 2013. Imaging type VI secretion-mediated bacterial killing. Cell Reports 3:36-41.
25. Durand E, Nguyen V S, Zoued A, Logger L, Pehau-Arnaudet G, Aschtgen M S, Spinelli S, Desmyter A, Bardiaux B, Dujeancourt A, Roussel A, Cambillau C, Cascales E, Fronzes R. 2015. Biogenesis and structure of a type VI secretion membrane core complex. Nature 523:555-560.
26. Hachani A, Lossi N S, Hamilton A, Jones C, Bleves S, Albesa-Jove D, Filloux A. 2011. Type VI secretion system in *Pseudomonas aeruginosa*: secretion and multimerization of VgrG proteins. J Biol Chem 286:12317-12327.
27. Hachani A, Allsopp L P, Oduko Y, Filloux A. 2014. The VgrG proteins are "a la carte" delivery systems for bacterial type VI effectors. J Biol Chem 289:17872-17884.
28. Ma L S, Hachani A, Lin J S, Filloux A, Lai E M. 2014. *Agrobacterium tumefaciens* deploys a superfamily of type VI secretion DNase effectors as weapons for interbacterial competition in planta. Cell Host Microbe 16:94-104.
29. Li M, Le Trong I, Carl M A, Larson E T, Chou S, De Leon J A, Dove S L, Stenkamp R E, Mougous J D. 2012. Structural basis for type VI secretion effector recognition by a cognate immunity protein. PLoS Pathog 8:e1002613.
30. Miyata S T, Unterweger D, Rudko S P, Pukatzki S 2013. Dual expression profile of type VI secretion system immunity genes protects pandemic *Vibrio cholerae*. PLoS Pathog 9:e1003752.
31. Cardarelli L, Saak C, Gibbs K A. 2015. Two proteins form a heteromeric bacterial self recognition complex in which variable subdomains determine allele-restricted binding. mBio 6:e00251.
32. Salomon D, Kinch L N, Trudgian D C, Guo X, Klimko J A, Grishin N V, Mirzaei H, Orth K. 2014. Marker for type VI secretion system effectors. Proc Natl Acad Sci USA 111:9271-9276.
33. Bonemann G, Pietrosiuk A, Diemand A, Zentgraf H, Mogk A. 2009. Remodelling of VipA/VipB tubules by ClpV-mediated threading is crucial for type VI protein secretion. The EMBO journal 28:315-325.
34. Kapitein N, Bonemann G, Pietrosiuk A, Seyffer F, Hausser I, Locker J K, Mogk A. 2013. ClpV recycles VipA/VipB tubules and prevents non-productive tubule formation to ensure efficient type VI protein secretion. Mol Microbiol 87:1013-1028.
35. Silverman J M, Agnello D M, Zheng H, Andrews B T, Li M, Catalano C E, Gonen T, Mougous J D. 2013. Haemolysin coregulated protein is an exported receptor and chaperone of type VI secretion substrates. Mol Cell 51:584-593.
36. Ruiz F M, Santillana E, Spinola-Amilibia M, Torreira E, Culebras E, Romero A. 2015. Correction: Crystal Structure of Hcp from *Acinetobacter baumannii*: A Component of the Type VI Secretion System. PloS One 10:e0136978.

37. Osipiuk J, Xu X, Cui H, Savchenko A, Edwards A, Joachimiak A. 2011. Crystal structure of secretory protein Hcp3 from *Pseudomonas aeruginosa*. Journal Struct Funct Genomics 12:21-26.
38. Douzi B, Spinelli S, Blangy S, Roussel A, Durand E, Brunet Y R, Cascales E, Cambillau C. 2014. Crystal structure and self-interaction of the type VI secretion tail-tube protein from enteroaggregative *Escherichia coli*. PloS One 9:e86918.
39. Gray K M, Passador L, Iglewski B H, Greenberg E P. 1994. Interchangeability and specificity of components from the quorum-sensing regulatory systems of *Vibrio fischeri* and *Pseudomonas aeruginosa*. J Bacteriol 176: 3076-3080.
40. Waters C M, Bassler B L. 2005. Quorum sensing: cell-to-cell communication in bacteria. Annu Rev Cell Dev Biol 21:319-346.
41. Vannini A, Volpari C, Gargioli C, Muraglia E, Cortese R, De Francesco R, Neddermann P, Marco S D. 2002. The crystal structure of the quorum sensing protein TraR bound to its autoinducer and target DNA. The EMBO journal 21:4393-4401.
42. Zhang R G, Pappas K M, Brace J L, Miller P C, Oulmassov 409 T, Molyneaux J M, Anderson J C, Bashkin J K, Winans S C, Joachimiak A. 2002. Structure of a bacterial quorum-sensing transcription factor complexed with pheromone and DNA. Nature 417:971-974.
43. Kaplan H B, Greenberg E P. 1985. Diffusion of autoinducer is involved in regulation of the *Vibrio-Fischeri* luminescence system. J Bacteriol 163:1210-1214.
44. Pearson J P, Van Delden C, Iglewski B H. 1998. Active efflux and diffusion are involved in transport of *Pseudomonas aeruginosa* cell-to-cell signals. J Bacteriol 181:1203-1210.
45. Aoki S K, Pamma R, Hernday A D, Bickham J E, Braaten B A, Low D A. 2005. Contact dependent inhibition of growth in *Escherichia coli*. Science 309:1245-1248.
46. Aoki S K, Malinverni J C, Jacoby K, Thomas B, Pamma R, Trinh B N, Remers S, Webb J, Braaten B A, Silhavy T J, Low D A. 2008. Contact-dependent growth inhibition requires the essential outer membrane protein BamA (YaeT) as the receptor and the inner membrane transport protein AcrB. Mol Microbiol 70:323-340.
47. Aoki S K, Diner E J, de Roodenbeke C T, Burgess B R, Poole S J, Braaten B A, Jones A M, Webb J S, Hayes C S, Cotter P A, Low D A. 2010. A widespread family of polymorphic contact dependent toxin delivery systems in bacteria. Nature 468:439-442.
48. Poole S J, Diner E J, Aoki S K, Braaten B A, t'Kint de Roodenbeke C, Low D A, Hayes C S. 2011. Identification of functional toxin/immunity genes linked to contact-dependent growth inhibition (CDI) and rearrangement hotspot (Rhs) systems. PLoS Genet 7:e1002217.
49. Diner E J, Beck C M, Webb J S, Low D A, Hayes C S. 2012. Identification of a target cell permissive factor required for contact-dependent growth inhibition (CDI). Genes Dev 26:515-525.
50. Ruhe Z C, Wallace A B, Low D A, Hayes C S. 2013. Receptor polymorphism restricts contact-dependent growth inhibition to members of the same species. mBio 4.
51. Anderson M S, Garcia E C, Cotter P A. 2012. The *Burkholderia* bcpAIOB genes define unique classes of two-partner secretion and contact dependent growth inhibition systems. PLOS Genetics 8:e1002877.
52. Anderson M S, Garcia E C, Cotter P A. 2014. Kind discrimination and competitive exclusion mediated by contact-dependent growth inhibition systems shape biofilm community structure. PLOS Pathog 10:e1004076.
53. Jones B V, Young R, Mahenthiralingam E, Stickler D J. 2004. Ultrastructure of *Proteus mirabilis* swarmer cell rafts and role of swarming in catheter-associated urinary tract infection. Infect Immun 72:3941-3950.
54. Belas R, Erskine D, Flaherty D. 1991. Transposon mutagenesis in *Proteus mirabilis*. J Bacteriol 173:6289-6293.
55. Gibbs K A, Urbanowski M L, Greenberg E P. 2008. Genetic determinants of self identity and social recognition in bacteria. Science 321:256-259.
56. Kaniga K, Delor I, Cornelis G R. 1991. A wide-host-range suicide vector for improving reverse genetics in gram-negative bacteria: inactivation of the blaA gene of *Yersinia enterocolitica*. Gene 109:137-141.
57. de Lorenzo V, Herrero M, Jakubzik U, Timmis K N. 1990. Mini-Tn5 transposon derivatives for insertion mutagenesis, promoter probing, and chromosomal insertion of cloned DNA in gram-negative eubacteria. J Bacteriol 172:6568-6572.
58. Sturgill G M, Siddiqui S, Ding X, Pecora N D, Rather P N. 2002. Isolation of lacZ fusions to *Proteus mirabilis* genes regulated by intercellular signaling: potential role for the sugar phosphotransferase (Pts) system in regulation. FEMS Microbiol Lett 217:43-50.
59. Belas R, Erskine D, Flaherty D. 1991. Transposon mutagenesis in *Proteus mirabilis*. J Bacteriol 173:6289-6293.
60. Cardarelli L, Saak C, Gibbs K A. 2015. Two proteins form a heteromeric bacterial self recognition complex in which variable subdomains determine allele-restricted binding. mBio 6:e00251.
61. Gibbs K A, Wenren L M, Greenberg E P. 2011. Identity gene expression in *Proteus mirabilis*. J Bacteriol 193: 3286-3292.
62. Wenren L M, Sullivan N L, Cardarelli L, Septer A N, Gibbs K A. 2013. Two independent pathways for self-recognition in *Proteus mirabilis* are linked by type VI-dependent export. mBio 4.
63. Simon R, Priefer U, Paler A. 1983. A broad host range mobilization system for in vivo genetic engineering: transposon mutagenesis in gram negative bacteria. Nat Biotechnology 1:784-791.
64. Schneider C A, Rasband W S, Eliceiri K W. 2012. NIH Image to ImageJ: 25 years of image analysis. Nature methods 9:671-675.
65. Schindelin J, Arganda-Carreras I, Frise E, Kaynig V, Longair M, Pietzsch T, Preibisch S, Rueden C, Saalfeld S, Schmid B, Tinevez J Y, White D J, Hartenstein V, Eliceiri K, Tomancak P, Cardona A. 2012. Fiji: an open-source platform for biological-image analysis. Nature methods 9:676-682.
66. Schindelin J, Rueden C T, Hiner M C, Eliceiri K W. 2015. The ImageJ ecosystem: An open platform for biomedical image analysis. Molecular reproduction and development 82:518-529.
67. Pietzsch T, Preibisch S, Tomancak P, Saalfeld S. 2012. ImgLib2—generic image processing in Java. Bioinformatics 28:3009-3011.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A IdsD protein comprising an amino acid sequence that is at least 90% identical to a sequence as provided by SEQ ID NO:2 or SEQ ID NO:4, or a fragment thereof, wherein the IdsD protein comprises a variable region that is at least 85% identical to the amino acid sequence of IdsD protein according to SEQ ID NO:12 or at least 85% identical to the amino acid sequence of IdsD protein according to SEQ ID NO:10, wherein the amino acid sequence of the IdsD protein is not identical to SEQ ID NO:2 or SEQ ID NO:4, and is not identical to the amino acid sequence of a naturally occurring *Proteus mirabilis* IdsD protein, wherein the IdsD protein is not encoded by a nucleic acid of SEQ ID NO:1 or SEQ ID NO:3, and wherein the fragment thereof is not encoded by a nucleic acid of SEQ ID NO:11.

2. The IdsD protein of claim 1, wherein the IdsD protein or fragment thereof comprises the variable region comprising SEQ ID NO:10 or SEQ ID NO:12.

3. The IdsD protein of claim 1, wherein the variable region comprises one or more mutations.

4. The IdsD protein of claim 3, wherein the one or more mutations are mutations at amino acid residues 761 and/or 765 of SEQ ID NO:2 or SEQ ID NO:4, or the one or more mutations are mutations at amino acid residues 1 and/or 5 of SEQ ID NO:10 or SEQ ID NO:12.

5. The IdsD protein of claim 1, wherein the IdsD protein is encoded by a nucleic acid sequence that is at least 90% identical to a sequence as provided by SEQ ID NO:1 or SEQ ID NO:3.

6. The IdsD protein of claim 2, wherein the variable region is encoded by a nucleic acid sequence provided by SEQ ID NO:9.

7. A bacterial composition which secretes the IdsD protein of claim 1.

8. The bacterial composition of claim 7, wherein the bacterial composition comprises *Proteus mirabilis*, or is derived therefrom.

9. A pharmaceutical composition comprising the IdsD protein of claim 1 and a pharmaceutically acceptable carrier.

10. A pharmaceutical composition comprising the IdsD protein of claim 1 and one or more therapeutic agents.

11. A method of reducing bacterial growth and/or swarming on a surface, the method comprising contacting or coating the surface with the IdsD protein of claim 1.

12. A method for reducing the occurrence of urinary tract infections in a subject with a medical device comprising coating of a medical device with the IdsD protein of claim 1 and implanting the device in a subject.

13. The method of claim 12, wherein the subject is a human.

14. A method for treating or preventing a bacterial infection, the method comprising administering to a subject in need thereof a therapeutically effective amount of the IdsD protein of claim 1.

15. The method of claim 14, wherein the bacterial infection is a urinary tract infection.

16. The method of claim 14, wherein the bacterial infection is a *Proteus mirabilis* infection.

17. A medical device kit comprising a medical device and IdsD protein of claim 1.

18. A composition comprising:

(a) IdsD protein comprising an amino acid sequence that is at least 90% identical to a sequence as provided by SEQ ID NO:2 or SEQ ID NO:4, or a fragment thereof, wherein the IdsD protein comprises a variable region that is at least 85% identical to the amino acid sequence of IdsD protein according to SEQ ID NO:10 or SEQ ID NO:12, wherein the amino acid sequence of the IdsD protein is not identical to SEQ ID NO:2 or SEQ ID NO:4, and is not identical to the amino acid sequence of a naturally occurring *Proteus mirabilis* IdsD protein, and (b) one or more therapeutic agents.

19. The composition of claim 18, wherein the IdsD protein or fragment thereof comprises the variable region comprising SEQ ID NO:10 or SEQ ID NO:12.

20. The composition of claim 18, wherein the variable region comprises one or more mutations.

21. The composition of claim 20, wherein the one or more mutations are mutations at amino acid residues 761 and/or 765 of SEQ ID NO:2 or SEQ ID NO:4, or the one or more mutations are mutations at amino acid residues 1 and/or 5 of SEQ ID NO:10 or SEQ ID NO:12.

22. The composition of claim 18, wherein the IdsD protein is encoded by a nucleic acid sequence that is at least 90% identical to a sequence as provided by SEQ ID NO:1 or SEQ ID NO:3.

23. The IdsD protein of claim 19, wherein the variable region is encoded by a nucleic acid sequence provided by SEQ ID NO:9 or SEQ ID NO:11.

24. A bacterial composition which secretes the IdsD protein of the composition of claim 18.

25. The bacterial composition of claim 24, wherein the bacterial composition comprises *Proteus mirabilis*, or is derived therefrom.

26. A pharmaceutical composition comprising the IdsD protein of the composition of claim 18 and a pharmaceutically acceptable carrier.

* * * * *

SEQUENCE LISTING

```
<160> NUMBER OF SEQ ID NOS: 19

<210> SEQ ID NO 1
<211> LENGTH: 3105
<212> TYPE: DNA
<213> ORGANISM: Artificial Sequence
<220> FEATURE:
<223> OTHER INFORMATION: Synthetic Polynucleotide

<400> SEQUENCE: 1

atgactggag aagtgaatga gaaatattta acaccgcaag agcgcaaagc gcgtcagatg      60

gtgaaggcgg taaacgaagc gagcccacga aacttaccgg ccgacgcggt ggtatgccca     120

tgtgaaaatg aacatcgccc tgtttatccg gtgcgttatg catataccaa cttttattgt     180

gatttacatt tttctacaat tgaacaagca ccaaataaaa cgttagaagc gagtattcct     240

ccttctatta atcaattatt gaatgcgaaa gatgttactg ctagtaaagg attttctgca     300

agattattaa gacaaggttg ggtttatgtt tttgaagaag gcaattaccc tactagaagt     360
```

-continued

```
aattctagca ataaaagtta tcaagaacaa aatgttgatg caacaaaagg acgcctatta    420
gtttttcaac atcaagtgac aaccagtgat ggcaatgaaa atttcattcc atatatattt    480
aagcaattaa aaaatggggg tgtcacttta aagaaaaacg gaaatagtaa tccttattta    540
gctataccga aagatgtgaa ggaagcgact atcttattca gcgaaagtaa attatctgat    600
tacacactta aaaaaatcat ttcatcttct aagtttagat cgaaattaat gcaaaaaatc    660
aattttattg attacaataa taacgattat tgtattgagc taaataaaga taatttaaat    720
cgacttgttg aggattataa agaagaagtt gataaattta agctatttgt taaagaattc    780
acgcattcaa atataccctc ttcttttttt tctgatacca caaaaatacc cgacttacca    840
caagatgcaa ctgttttgat taatcaagta aatagtgttc tagattataa tgaaaaagcg    900
acattgctta ttttaaaaga tcccgtagga taccaaaaag atattttatc ttattataat    960
attgtaacaa aattacattt attatatcag aactattata gccatccgga taaaattggc   1020
caatttatta cgagtataca agaagctagt catcacatta aagatactga tgaaaaagaa   1080
aaaatgcaaa caatactaaa agagagtatt aatcagaatg cattagataa tgagtggaaa   1140
aatattcata aaacatttat ttttttgag aaacatcaac gtattgtatt atcattgtat   1200
gaaagcttta tgaataatcc ggcaatcatt aatgaaaacg gtggcttaaa acattatttt   1260
gattatgctt tttcatatca cgaacgtata actaaagaag atgtctttag tattgatttt   1320
tttaaggacc ttaatcaagc ttttgattta tattttgatt tagtatctcc attaatgaat   1380
tctatcgaag gacaaagaac attagataaa ttatattcaa ttaatgatga agaaaataat   1440
agcctgtggg tgggagtgac aaagaaagta attagtctta ttgctaattc aaaaattaag   1500
gacgctcttt taaatgtaca agaatatgca atgcatatcg aaaattttgt taataagctt   1560
gcatttattt gctcagatag cattggtttc gcgtttacaa aaacaagtaa ggtactttct   1620
cattacgata ttaaaaatag actaattaat actaagggta ttgactattt agcccaaaag   1680
atacttccga tgatactggc attttgcaac acaaaaattt cattaaccga gtttgttaaa   1740
ttatcgggta atgagcttaa ccagtggatg gaacaactcc gtaaattaac gggacaaata   1800
gtaccaaatc tgcaacatcc taaattaaat aagctttttt cttggaaaca aaaaataata   1860
aatctaggcg aagagactgc cgttcttatt ccgaagattg agatcataga tattactaaa   1920
aataagattt atatttatgg caaagatgca ttacaggttt ccactaagct atttttaaac   1980
ggtttcagca tgatcaccgg atcaatccaa gcttatacat tacaaggtat gagtttgtat   2040
gaacgtaatg acccattaaa actatccccc tataatctgt atacagcaca gattattgcg   2100
aatttatttg tagcaagcta cagtatttta aaagtttctc aagaggcgac aaaattatct   2160
caaacagtat cgagcaccac actgaaattc tttttagata aaataaaatt acctatgcta   2220
acaacagaag tgggaaccaa aagaatggca gcattaggta agattgcagg tgccgttggt   2280
gccgctcttg ccgctcgtga cgcattagaa gcttttcata ttggaaatta taaacaatct   2340
gtatcaaata tagctattgt gattggttct ataattttaa ttactgctgt tactggagga   2400
tgggctttat ttgctggggc acttattttg gggggattta tctcaagcca actcaccagt   2460
tggagtcatt tagaaacttt actaaaacat agtttttggg ggaatgaaaa aaggtctaat   2520
ttttgggata atgatagacc aacaccgata ggagaacaat taaaacaata tataaaagaa   2580
tttgaattct ataaacaaaa agggctaatt gaattacaag agttttataa tctattttat   2640
acagctaaaa tgactcaaga aaaaatacca aatggaaaac tccgcttatc ttttgaattt   2700
actaatttta ccccagggat ttcagaagta tattttcact ttgttacaga ggttggttat   2760
```

```
cacagcggct tggcagaaga aataaaaaca cctagttcag cttatgttct aaataaacga   2820

aaagacctct tagaaattag cgaacaatta aaaatggcaa gtgaaaaagg tgattggaac   2880

cctgaaacag gtatatttaa atttagtttg gaagtacagt ctcaattagt aaatacatat   2940

tctgcttttg gtgcacatcc taatagccgt ataggtattg aagatttata ttggtattat   3000

caagtcaatc ccgaggtaac aacaccgatg cgttatatca attggggggg agatacccaa   3060

gaaaacaatc agcttttagg ctttattaac agtgagaata tctaa                   3105
```

```
<210> SEQ ID NO 2
<211> LENGTH: 1034
<212> TYPE: PRT
<213> ORGANISM: Artificial Sequence
<220> FEATURE:
<223> OTHER INFORMATION: Synthetic Polypeptide

<400> SEQUENCE: 2

Met Thr Gly Glu Val Asn Glu Lys Tyr Leu Thr Pro Gln Glu Arg Lys
1               5                   10                  15

Ala Arg Gln Met Val Lys Ala Val Asn Glu Ala Ser Pro Arg Asn Leu
            20                  25                  30

Pro Ala Asp Ala Val Val Cys Pro Cys Glu Asn Glu His Arg Pro Val
        35                  40                  45

Tyr Pro Val Arg Tyr Ala Tyr Thr Asn Phe Tyr Cys Asp Leu His Phe
    50                  55                  60

Ser Thr Ile Glu Gln Ala Pro Asn Lys Thr Leu Glu Ala Ser Ile Pro
65                  70                  75                  80

Pro Ser Ile Asn Gln Leu Leu Asn Ala Lys Asp Val Thr Ala Ser Lys
                85                  90                  95

Gly Phe Ser Ala Arg Leu Leu Arg Gln Gly Trp Val Tyr Val Phe Glu
            100                 105                 110

Glu Gly Asn Tyr Pro Thr Arg Ser Asn Ser Ser Asn Lys Ser Tyr Gln
        115                 120                 125

Glu Gln Asn Val Asp Ala Thr Lys Gly Arg Leu Leu Val Phe Gln His
    130                 135                 140

Gln Val Thr Thr Ser Asp Gly Asn Glu Asn Phe Ile Pro Tyr Ile Phe
145                 150                 155                 160

Lys Gln Leu Lys Asn Gly Gly Val Thr Leu Lys Lys Asn Gly Asn Ser
                165                 170                 175

Asn Pro Tyr Leu Ala Ile Pro Lys Asp Val Lys Glu Ala Thr Ile Leu
            180                 185                 190

Phe Ser Glu Ser Lys Leu Ser Asp Tyr Thr Leu Lys Lys Ile Ile Ser
        195                 200                 205

Ser Ser Lys Phe Arg Ser Lys Leu Met Gln Lys Ile Asn Phe Ile Asp
    210                 215                 220

Tyr Asn Asn Asn Asp Tyr Cys Ile Glu Leu Asn Lys Asp Asn Leu Asn
225                 230                 235                 240

Arg Leu Val Glu Asp Tyr Lys Glu Glu Val Asp Lys Phe Lys Leu Phe
                245                 250                 255

Val Lys Glu Phe Thr His Ser Asn Ile Pro Ser Ser Phe Phe Ser Asp
            260                 265                 270

Thr Thr Lys Ile Pro Asp Leu Pro Gln Asp Ala Thr Val Leu Ile Asn
        275                 280                 285

Gln Val Asn Ser Val Leu Asp Tyr Asn Glu Lys Ala Thr Leu Leu Ile
    290                 295                 300
```

-continued

```
Leu Lys Asp Pro Val Gly Tyr Gln Lys Asp Ile Leu Ser Tyr Tyr Asn
305                 310                 315                 320

Ile Val Thr Lys Leu His Leu Leu Tyr Gln Asn Tyr Tyr Ser His Pro
                325                 330                 335

Asp Lys Ile Gly Gln Phe Ile Thr Ser Ile Gln Glu Ala Ser His His
            340                 345                 350

Ile Lys Asp Thr Asp Glu Lys Glu Lys Met Gln Thr Ile Leu Lys Glu
        355                 360                 365

Ser Ile Asn Gln Asn Ala Leu Asp Asn Glu Trp Lys Asn Ile His Lys
    370                 375                 380

Thr Phe Ile Phe Phe Glu Lys His Gln Arg Ile Val Leu Ser Leu Tyr
385                 390                 395                 400

Glu Ser Phe Met Asn Asn Pro Ala Ile Ile Asn Glu Asn Gly Gly Leu
                405                 410                 415

Lys His Tyr Phe Asp Tyr Ala Phe Ser Tyr His Glu Arg Ile Thr Lys
            420                 425                 430

Glu Asp Val Phe Ser Ile Asp Phe Phe Lys Asp Leu Asn Gln Ala Phe
        435                 440                 445

Asp Leu Tyr Phe Asp Leu Val Ser Pro Leu Met Asn Ser Ile Glu Gly
    450                 455                 460

Gln Arg Thr Leu Asp Lys Leu Tyr Ser Ile Asn Asp Glu Glu Asn Asn
465                 470                 475                 480

Ser Leu Trp Val Gly Val Thr Lys Lys Val Ile Ser Leu Ile Ala Asn
                485                 490                 495

Ser Lys Ile Lys Asp Ala Leu Leu Asn Val Gln Glu Tyr Ala Met His
            500                 505                 510

Ile Glu Asn Phe Val Asn Lys Leu Ala Phe Ile Cys Ser Asp Ser Ile
        515                 520                 525

Gly Phe Ala Phe Thr Lys Thr Ser Lys Val Leu Ser His Tyr Asp Ile
    530                 535                 540

Lys Asn Arg Leu Ile Asn Thr Lys Gly Ile Asp Tyr Leu Ala Gln Lys
545                 550                 555                 560

Ile Leu Pro Met Ile Leu Ala Phe Cys Asn Thr Lys Ile Ser Leu Thr
                565                 570                 575

Glu Phe Val Lys Leu Ser Gly Asn Glu Leu Asn Gln Trp Met Glu Gln
            580                 585                 590

Leu Arg Lys Leu Thr Gly Gln Ile Val Pro Asn Leu Gln His Pro Lys
        595                 600                 605

Leu Asn Lys Leu Phe Ser Trp Lys Gln Lys Ile Ile Asn Leu Gly Glu
    610                 615                 620

Glu Thr Ala Val Leu Ile Pro Lys Ile Glu Ile Ile Asp Ile Thr Lys
625                 630                 635                 640

Asn Lys Ile Tyr Ile Tyr Gly Lys Asp Ala Leu Gln Val Ser Thr Lys
                645                 650                 655

Leu Phe Leu Asn Gly Phe Ser Met Ile Thr Gly Ser Ile Gln Ala Tyr
            660                 665                 670

Thr Leu Gln Gly Met Ser Leu Tyr Glu Arg Asn Asp Pro Leu Lys Leu
        675                 680                 685

Ser Pro Tyr Asn Leu Tyr Thr Ala Gln Ile Ile Ala Asn Leu Phe Val
    690                 695                 700

Ala Ser Tyr Ser Ile Leu Lys Val Ser Gln Glu Ala Thr Lys Leu Ser
705                 710                 715                 720
```

-continued

```
Gln Thr Val Ser Ser Thr Thr Leu Lys Phe Phe Leu Asp Lys Ile Lys
            725                 730                 735

Leu Pro Met Leu Thr Thr Glu Val Gly Thr Lys Arg Met Ala Ala Leu
            740                 745                 750

Gly Lys Ile Ala Gly Ala Val Gly Ala Ala Leu Ala Ala Arg Asp Ala
        755                 760                 765

Leu Glu Ala Phe His Ile Gly Asn Tyr Lys Gln Ser Val Ser Asn Ile
    770                 775                 780

Ala Ile Val Ile Gly Ser Ile Ile Leu Ile Thr Ala Val Thr Gly Gly
785                 790                 795                 800

Trp Ala Leu Phe Ala Gly Ala Leu Ile Leu Gly Gly Phe Ile Ser Ser
            805                 810                 815

Gln Leu Thr Ser Trp Ser His Leu Glu Thr Leu Leu Lys His Ser Phe
            820                 825                 830

Trp Gly Asn Glu Lys Arg Ser Asn Phe Trp Asp Asn Asp Arg Pro Thr
        835                 840                 845

Pro Ile Gly Glu Gln Leu Lys Gln Tyr Ile Lys Glu Phe Glu Phe Tyr
    850                 855                 860

Lys Gln Lys Gly Leu Ile Glu Leu Gln Glu Phe Tyr Asn Leu Phe Tyr
865                 870                 875                 880

Thr Ala Lys Met Thr Gln Glu Lys Ile Pro Asn Gly Lys Leu Arg Leu
            885                 890                 895

Ser Phe Glu Phe Thr Asn Phe Thr Pro Gly Ile Ser Glu Val Tyr Phe
            900                 905                 910

His Phe Val Thr Glu Val Gly Tyr His Ser Gly Leu Ala Glu Glu Ile
        915                 920                 925

Lys Thr Pro Ser Ser Ala Tyr Val Leu Asn Lys Arg Lys Asp Leu Leu
    930                 935                 940

Glu Ile Ser Glu Gln Leu Lys Met Ala Ser Glu Lys Gly Asp Trp Asn
945                 950                 955                 960

Pro Glu Thr Gly Ile Phe Lys Phe Ser Leu Glu Val Gln Ser Gln Leu
            965                 970                 975

Val Asn Thr Tyr Ser Ala Phe Gly Ala His Pro Asn Ser Arg Ile Gly
            980                 985                 990

Ile Glu Asp Leu Tyr Trp Tyr Tyr  Gln Val Asn Pro Glu  Val Thr Thr
        995                 1000                 1005

Pro Met  Arg Tyr Ile Asn Trp  Gly Gly Asp Thr Gln  Glu Asn Asn
    1010                 1015                 1020

Gln Leu  Leu Gly Phe Ile Asn  Ser Glu Asn Ile
    1025                 1030


<210> SEQ ID NO 3
<211> LENGTH: 3102
<212> TYPE: DNA
<213> ORGANISM: Artificial Sequence
<220> FEATURE:
<223> OTHER INFORMATION: Synthetic Polynucleotide

<400> SEQUENCE: 3

atgactggag aagtgaatga gaaatattta acaccgcaag agcgcaaagc gcgtcagatg      60

gtgaaggcgg taaacgaagc gagcccacga aacttaccgg ccgacgcggt ggtatgccca     120

tgtgaaaatg aacatcgccc tgtttatccg gtgcgttatg catataccaa cttttattgt     180

gatttacatt tttctacaat tgaacaagca ccaaataaaa cgttagaagc gagtattcct     240

ccttctatta atcaattatt gaatgcgaaa gatgttactg ctagtaaagg attttctgca     300
```

```
agattattaa gacaaggttg ggtttatgtt tttgaagaag gcaattaccc tactagaagt    360
aattctagta ataaaagtta tcaagaacaa aatgttgatg cgacaaaagg acgcctatta    420
gtttttcaac atcaagttac aaccagtgat ggcaatgaaa atttcattcc atatatattt    480
aagcaattaa aaaatggggg tgtcacttta aagaaaaacg gaaatagtaa tccttattta    540
gctataccga aagatgtgaa ggaagcgact atcttattca gcgaaagtaa attatctgat    600
tacacactta aaaaaatcat ttcatcttct aagtttagat cgaaattaat gcaaaaaatc    660
aattttattg attacaacaa taacgattat tgtattgagc taaataaaga taatttaaat    720
cgacttgttg aggattataa agaagaagtt gataaattta agctatttgt taaagaattc    780
acgcattcaa atataccctc ttcttttttt tctgatacca caaaaatacc cgacttacca    840
caagatgcaa ctgttttgat taatcaaata aatagtgttc tagattataa tgaaaaagcg    900
acattgctta ttttaaaaga tcccgtagga taccaaaaag atgttttatc ttattataat    960
attgtaacaa aattacattt attatatcag aactattata gccatccgga taaaattggc   1020
caatttatta cgagtataca agaagctagt catcacatta aagatactga tgaaaaagaa   1080
aaaatgcaaa caatactaaa agagagtatt aatcagaatg cattagataa tgagtggaaa   1140
aatattcata aaacatttat ttttttgag aaacatcaac gtattgtatt atcattgtat    1200
gaaagcttta tgaataatcc ggcaatcatt aatgaaaacg gtggcttaaa acattatttt   1260
gattatgctt tttcatatca cgaacgtata acgaaagaag atgtctttag tattgatttt   1320
tttaaggacc ttaatcaagc ttttgattta tattttgatt taatatctcc attaatgaat   1380
tctaccgaag gacaaagaac attagataaa ttatattcaa ttaatgatga agaaaataat   1440
agcctgtggg tgggagtgac aaagaaagta attagtcttg ttgctaattc aaaaattatg   1500
gacgcacttt taaatgcaca agaatatgca gagaatatcg aaaattttgt taataagctt   1560
gcgtttattt gctcagatag cattggtttt gcatttacaa aaacaagtaa gatgctttct   1620
cattacgata ttaaaaatag actaattaat actaagggta ttgactattt agctcaaaag   1680
atacttccga tgatactggc attttgcaac acaaaaattt cattaaccga gtttgttaaa   1740
ttatcgggta atgagcttaa ccagtgggtg gaacaactcc gtaaattaac ggaacaaata   1800
gtaccaaatc tgcaacatcc taaattaaat aagctttttt cttggaaaca aaaaataata   1860
aatctaggcg aagagactgc cgttcttatt ccgaagattg agatcacaga tattactaaa   1920
aataagattt atatttatgg taaagatgca ttacaggttt ccactaagct atttttaaac   1980
ggtttcagca tgatcaccgg atcaatccaa gcttatacat tacaaggtat gagtttgtat   2040
gaacgtaatg acccattaaa actatccccc tataatctgt atacagcaca gattattgcg   2100
aatttatttg tagcaagcta cagtatttta aaagtttctc aagaggcgac aaaattatct   2160
caaacagtat cgagcaccac actgaaattc tttttagata aaataaaatt acctatgcta   2220
acaacagaag tgggaaccaa aagaatggca gcattaggta agattgcagg tgccgttggt   2280
gttgctcttg ccactcgaga tgcattagaa gcttttcata ttggaaataa taaacaaggt   2340
ttatcaaatg tagccattgc cattggttct ttcatgctaa tttttgttac agggggatgg   2400
gctctatttg caggactgct aatattagga ggcttcttct caagtcaact caccagttgg   2460
agtcatttgg aaactttgct aaggcacagt ttttggggaa atgaagaaag ttcaaatttt   2520
tgggataata atagaccaac accgatagga gaacaattaa aacaatatat aaaagaattt   2580
gaattctatg aacaaaaagg gctaattgaa ttacaagagt tttataatct attttataca   2640
```

-continued

```
gctaaaatga ctcaagaaaa aataccaaat ggaaaactcc gcttatcttt tgaatttact   2700

aattttaccc cagggatttc agaagtatat tttcactttg ttacagaggt tggttatcac   2760

agcggcttgg cagaagaaat aaaaacacct agttcagctt atgttctaaa taaacgaaaa   2820

gacctcttag aaattagcga acaattaaaa atggcaagtg aaaaaggtga ttggaaccct   2880

gaaacaggta tattgaaatt tagtttggaa gtacagtctc aattagtaaa tacatattct   2940

gcttttggtg cacatcctaa tagccgtata ggtattgaag atttatattg gtattatcaa   3000

gtcaatcccg aggtaacaac accgatgcgt tatatcaatt ggggggga ga tacccaagaa   3060

aacaatcggc ttttaggctt tattaacagt gagaatatct aa                       3102
```

<210> SEQ ID NO 4
<211> LENGTH: 1033
<212> TYPE: PRT
<213> ORGANISM: Artificial Sequence
<220> FEATURE:
<223> OTHER INFORMATION: Synthetic Polypeptide

<400> SEQUENCE: 4

```
Met Thr Gly Glu Val Asn Glu Lys Tyr Leu Thr Pro Gln Glu Arg Lys
1               5                   10                  15

Ala Arg Gln Met Val Lys Ala Val Asn Glu Ala Ser Pro Arg Asn Leu
            20                  25                  30

Pro Ala Asp Ala Val Val Cys Pro Cys Glu Asn Glu His Arg Pro Val
        35                  40                  45

Tyr Pro Val Arg Tyr Ala Tyr Thr Asn Phe Tyr Cys Asp Leu His Phe
    50                  55                  60

Ser Thr Ile Glu Gln Ala Pro Asn Lys Thr Leu Glu Ala Ser Ile Pro
65                  70                  75                  80

Pro Ser Ile Asn Gln Leu Leu Asn Ala Lys Asp Val Thr Ala Ser Lys
                85                  90                  95

Gly Phe Ser Ala Arg Leu Leu Arg Gln Gly Trp Val Tyr Val Phe Glu
            100                 105                 110

Glu Gly Asn Tyr Pro Thr Arg Ser Asn Ser Ser Asn Lys Ser Tyr Gln
        115                 120                 125

Glu Gln Asn Val Asp Ala Thr Lys Gly Arg Leu Leu Val Phe Gln His
    130                 135                 140

Gln Val Thr Thr Ser Asp Gly Asn Glu Asn Phe Ile Pro Tyr Ile Phe
145                 150                 155                 160

Lys Gln Leu Lys Asn Gly Gly Val Thr Leu Lys Lys Asn Gly Asn Ser
                165                 170                 175

Asn Pro Tyr Leu Ala Ile Pro Lys Asp Val Lys Glu Ala Thr Ile Leu
            180                 185                 190

Phe Ser Glu Ser Lys Leu Ser Asp Tyr Thr Leu Lys Lys Ile Ile Ser
        195                 200                 205

Ser Ser Lys Phe Arg Ser Lys Leu Met Gln Lys Ile Asn Phe Ile Asp
    210                 215                 220

Tyr Asn Asn Asn Asp Tyr Cys Ile Glu Leu Asn Lys Asp Asn Leu Asn
225                 230                 235                 240

Arg Leu Val Glu Asp Tyr Lys Glu Glu Val Asp Lys Phe Lys Leu Phe
                245                 250                 255

Val Lys Glu Phe Thr His Ser Asn Ile Pro Ser Ser Phe Phe Ser Asp
            260                 265                 270

Thr Thr Lys Ile Pro Asp Leu Pro Gln Asp Ala Thr Val Leu Ile Asn
        275                 280                 285
```

```
Gln Ile Asn Ser Val Leu Asp Tyr Asn Glu Lys Ala Thr Leu Leu Ile
    290                 295                 300

Leu Lys Asp Pro Val Gly Tyr Gln Lys Asp Val Leu Ser Tyr Tyr Asn
305                 310                 315                 320

Ile Val Thr Lys Leu His Leu Leu Tyr Gln Asn Tyr Tyr Ser His Pro
                325                 330                 335

Asp Lys Ile Gly Gln Phe Ile Thr Ser Ile Gln Glu Ala Ser His His
            340                 345                 350

Ile Lys Asp Thr Asp Glu Lys Glu Lys Met Gln Thr Ile Leu Lys Glu
        355                 360                 365

Ser Ile Asn Gln Asn Ala Leu Asp Asn Glu Trp Lys Asn Ile His Lys
    370                 375                 380

Thr Phe Ile Phe Phe Glu Lys His Gln Arg Ile Val Leu Ser Leu Tyr
385                 390                 395                 400

Glu Ser Phe Met Asn Asn Pro Ala Ile Ile Asn Glu Asn Gly Gly Leu
                405                 410                 415

Lys His Tyr Phe Asp Tyr Ala Phe Ser Tyr His Glu Arg Ile Thr Lys
            420                 425                 430

Glu Asp Val Phe Ser Ile Asp Phe Phe Lys Asp Leu Asn Gln Ala Phe
        435                 440                 445

Asp Leu Tyr Phe Asp Leu Ile Ser Pro Leu Met Asn Ser Thr Glu Gly
    450                 455                 460

Gln Arg Thr Leu Asp Lys Leu Tyr Ser Ile Asn Asp Glu Glu Asn Asn
465                 470                 475                 480

Ser Leu Trp Val Gly Val Thr Lys Lys Val Ile Ser Leu Val Ala Asn
                485                 490                 495

Ser Lys Ile Met Asp Ala Leu Leu Asn Ala Gln Glu Tyr Ala Glu Asn
            500                 505                 510

Ile Glu Asn Phe Val Asn Lys Leu Ala Phe Ile Cys Ser Asp Ser Ile
        515                 520                 525

Gly Phe Ala Phe Thr Lys Thr Ser Lys Met Leu Ser His Tyr Asp Ile
    530                 535                 540

Lys Asn Arg Leu Ile Asn Thr Lys Gly Ile Asp Tyr Leu Ala Gln Lys
545                 550                 555                 560

Ile Leu Pro Met Ile Leu Ala Phe Cys Asn Thr Lys Ile Ser Leu Thr
                565                 570                 575

Glu Phe Val Lys Leu Ser Gly Asn Glu Leu Asn Gln Trp Val Glu Gln
            580                 585                 590

Leu Arg Lys Leu Thr Glu Gln Ile Val Pro Asn Leu Gln His Pro Lys
        595                 600                 605

Leu Asn Lys Leu Phe Ser Trp Lys Gln Lys Ile Ile Asn Leu Gly Glu
    610                 615                 620

Glu Thr Ala Val Leu Ile Pro Lys Ile Glu Ile Thr Asp Ile Thr Lys
625                 630                 635                 640

Asn Lys Ile Tyr Ile Tyr Gly Lys Asp Ala Leu Gln Val Ser Thr Lys
                645                 650                 655

Leu Phe Leu Asn Gly Phe Ser Met Ile Thr Gly Ser Ile Gln Ala Tyr
            660                 665                 670

Thr Leu Gln Gly Met Ser Leu Tyr Glu Arg Asn Asp Pro Leu Lys Leu
        675                 680                 685

Ser Pro Tyr Asn Leu Tyr Thr Ala Gln Ile Ile Ala Asn Leu Phe Val
    690                 695                 700
```

Ala Ser Tyr Ser Ile Leu Lys Val Ser Gln Glu Ala Thr Lys Leu Ser
705 710 715 720

Gln Thr Val Ser Ser Thr Thr Leu Lys Phe Phe Leu Asp Lys Ile Lys
725 730 735

Leu Pro Met Leu Thr Thr Glu Val Gly Thr Lys Arg Met Ala Ala Leu
740 745 750

Gly Lys Ile Ala Gly Ala Val Gly Val Ala Leu Ala Thr Arg Asp Ala
755 760 765

Leu Glu Ala Phe His Ile Gly Asn Asn Lys Gln Gly Leu Ser Asn Val
770 775 780

Ala Ile Ala Ile Gly Ser Phe Met Leu Ile Phe Val Thr Gly Gly Trp
785 790 795 800

Ala Leu Phe Ala Gly Leu Leu Ile Leu Gly Gly Phe Phe Ser Ser Gln
805 810 815

Leu Thr Ser Trp Ser His Leu Glu Thr Leu Leu Arg His Ser Phe Trp
820 825 830

Gly Asn Glu Glu Ser Ser Asn Phe Trp Asp Asn Asn Arg Pro Thr Pro
835 840 845

Ile Gly Glu Gln Leu Lys Gln Tyr Ile Lys Glu Phe Glu Phe Tyr Glu
850 855 860

Gln Lys Gly Leu Ile Glu Leu Gln Glu Phe Tyr Asn Leu Phe Tyr Thr
865 870 875 880

Ala Lys Met Thr Gln Glu Lys Ile Pro Asn Gly Lys Leu Arg Leu Ser
885 890 895

Phe Glu Phe Thr Asn Phe Thr Pro Gly Ile Ser Glu Val Tyr Phe His
900 905 910

Phe Val Thr Glu Val Gly Tyr His Ser Gly Leu Ala Glu Glu Ile Lys
915 920 925

Thr Pro Ser Ser Ala Tyr Val Leu Asn Lys Arg Lys Asp Leu Leu Glu
930 935 940

Ile Ser Glu Gln Leu Lys Met Ala Ser Glu Lys Gly Asp Trp Asn Pro
945 950 955 960

Glu Thr Gly Ile Leu Lys Phe Ser Leu Glu Val Gln Ser Gln Leu Val
965 970 975

Asn Thr Tyr Ser Ala Phe Gly Ala His Pro Asn Ser Arg Ile Gly Ile
980 985 990

Glu Asp Leu Tyr Trp Tyr Tyr Gln Val Asn Pro Glu Val Thr Thr Pro
995 1000 1005

Met Arg Tyr Ile Asn Trp Gly Gly Asp Thr Gln Glu Asn Asn Arg
1010 1015 1020

Leu Leu Gly Phe Ile Asn Ser Glu Asn Ile
1025 1030

<210> SEQ ID NO 5
<211> LENGTH: 939
<212> TYPE: DNA
<213> ORGANISM: Artificial Sequence
<220> FEATURE:
<223> OTHER INFORMATION: Synthetic Polynucleotide

<400> SEQUENCE: 5
atgagtattt tttttaatcc cgctaaacac ccacatcgct taaagccaca accattaggg 60
acgcaaggcg agcactataa cgaagattgg cccatgcctg agctcgattt tttagagacc 120
gtagataaac aacagtgcat tctggttgat aaagaaatac gccgacgtga tgcgtttgct 180

-continued

```
ttccctgggt ttattaccgg tattattacc tttattatgg tgtttcattt tgtttttaca    240

gaacataatt caaagtatat ccgttttaat aaaaatcttc atgactatac attagaatat    300

aaagcccaat atgaagataa agcccaaaga gataaactac cttcatttat acttgataag    360

tacgcccctt atttcaatca agaaaaactg tctattttag attatattca tgtttatttt    420

gggggtcata ttacatcaac cccttatatt gatacttcca ttttgtctac cctactcatt    480

tcattagttt atttaattgt agtatctggc tatcaatctt ttttcaaaaa aaatccaata    540

ctcgttttta atcgtgaaag aaatctggtc tatacttggc gcaaaaaataa ggtatttatt    600

gcccgctatc ctgaaattgg tatcggtaaa attggtaaaa cacttacctt tcaattattc    660

gggttagata agtcaaaaca aactttagtt tctgaattgt tttccctaa tgtctatgtt    720

tattcagtct acaataccag tactgactat cacgaccagc gcttcattaa ttttatcaat    780

acttatatgc gcgaagggcg tgatgccatt attccattcg attatcaccg taaaaaaccc    840

aaagtgtatt ttggcaaaaa cccacctcct gctgattttg aacaacaggt cgaacaaatt    900

ttagcaaagc ttgatcagga gaaagaacac catgcgtag                           939
```

<210> SEQ ID NO 6
<211> LENGTH: 312
<212> TYPE: PRT
<213> ORGANISM: Artificial Sequence
<220> FEATURE:
<223> OTHER INFORMATION: Synthetic Polypeptide

<400> SEQUENCE: 6

```
Met Ser Ile Phe Phe Asn Pro Ala Lys His Pro His Arg Leu Lys Pro
1               5                   10                  15

Gln Pro Leu Gly Thr Gln Gly Glu His Tyr Asn Glu Asp Trp Pro Met
            20                  25                  30

Pro Glu Leu Asp Phe Leu Glu Thr Val Asp Lys Gln Gln Cys Ile Leu
        35                  40                  45

Val Asp Lys Glu Ile Arg Arg Arg Asp Ala Phe Ala Phe Pro Gly Phe
    50                  55                  60

Ile Thr Gly Ile Ile Thr Phe Ile Met Val Phe His Phe Val Phe Thr
65                  70                  75                  80

Glu His Asn Ser Lys Tyr Ile Arg Phe Asn Lys Asn Leu His Asp Tyr
                85                  90                  95

Thr Leu Glu Tyr Lys Ala Gln Tyr Glu Asp Lys Ala Gln Arg Asp Lys
            100                 105                 110

Leu Pro Ser Phe Ile Leu Asp Lys Tyr Ala Pro Tyr Phe Asn Gln Glu
        115                 120                 125

Lys Leu Ser Ile Leu Asp Tyr Ile His Val Tyr Phe Gly Gly His Ile
    130                 135                 140

Thr Ser Thr Pro Tyr Ile Asp Thr Ser Ile Leu Ser Thr Leu Leu Ile
145                 150                 155                 160

Ser Leu Val Tyr Leu Ile Val Val Ser Gly Tyr Gln Ser Phe Phe Lys
                165                 170                 175

Lys Asn Pro Ile Leu Val Phe Asn Arg Glu Arg Asn Leu Val Tyr Thr
            180                 185                 190

Trp Arg Lys Asn Lys Val Phe Ile Ala Arg Tyr Pro Glu Ile Gly Ile
        195                 200                 205

Gly Lys Ile Gly Lys Thr Leu Thr Phe Gln Leu Phe Gly Leu Asp Lys
    210                 215                 220

Ser Lys Gln Thr Leu Val Ser Glu Leu Phe Phe Pro Asn Val Tyr Val
```

```
225                 230                 235                 240

Tyr Ser Val Tyr Asn Thr Ser Thr Asp Tyr His Asp Gln Arg Phe Ile
                245                 250                 255

Asn Phe Ile Asn Thr Tyr Met Arg Glu Gly Arg Asp Ala Ile Ile Pro
            260                 265                 270

Phe Asp Tyr His Arg Lys Lys Pro Lys Val Tyr Phe Gly Lys Asn Pro
        275                 280                 285

Pro Pro Ala Asp Phe Glu Gln Gln Val Glu Gln Ile Leu Ala Lys Leu
    290                 295                 300

Asp Gln Glu Lys Glu His His Ala
305                 310
```

<210> SEQ ID NO 7
<211> LENGTH: 939
<212> TYPE: DNA
<213> ORGANISM: Artificial Sequence
<220> FEATURE:
<223> OTHER INFORMATION: Synthetic Polynucleotide

<400> SEQUENCE: 7

```
atgagtattt ttttcaatcc cgctaaacac ccacatcgct tgaagccaca accattgggg      60

gagcaaggtg agcgctataa cgaagattgg cccatgcctg agctcgattt tttagagacc     120

gtggataaac aacagtgcat tctggttgat aaagaaatac gccgacgtga tgcgtttgct     180

ttccctgggt ttattaccgg tattattacc tttattatgg tatttcattt tgtttttaca     240

gaacataatt caaagtatat ccgttttaat aaaaatcttc atgactatac attagaatat     300

aaagcgcaat atgaagataa aactcaaaga gataaactac cttcatttat acttgataag     360

tacgcccctt atttcaatca agaaaaactg tctattttag attatattca tgtttatttt     420

gggggacata ttacatcaaa accctatcaa aatacgctat tttttctttc tactttcatc     480

gcacctttct tcttaattgg cttgggtggc tatcaatctt ttttcaaaaa aaatccaata     540

ctcgttttta atcgtgaaag aaatctggtt tatacttggc gcaaaaaata ggtatttatt     600

gcccgctatc ctgaaattgg tatcggtaaa attggtaaaa cacttacctt tcaattattc     660

gggttagata agtcaaaaca aactttagtt tctgaattat ttttccctaa tgtctatgtt     720

tattcagtgt acaataccag tactgactat cacgaccagc gcttcattaa ttttatcaat     780

acttatatgc gcgaagggcg tgatgccatt attccattcg attatcaccg taaaaaaccc     840

aaagtgtatt ttggcaaaaa cccacctcct gctgattttg agcaacaggt cgaacagatt     900

ttagcaaagc ttgatcagga gaaaaaacac catgcgtag                            939
```

<210> SEQ ID NO 8
<211> LENGTH: 312
<212> TYPE: PRT
<213> ORGANISM: Artificial Sequence
<220> FEATURE:
<223> OTHER INFORMATION: Synthetic Polypeptide

<400> SEQUENCE: 8

```
Met Ser Ile Phe Phe Asn Pro Ala Lys His Pro His Arg Leu Lys Pro
1               5                   10                  15

Gln Pro Leu Gly Glu Gln Gly Glu Arg Tyr Asn Glu Asp Trp Pro Met
            20                  25                  30

Pro Glu Leu Asp Phe Leu Glu Thr Val Asp Lys Gln Gln Cys Ile Leu
        35                  40                  45

Val Asp Lys Glu Ile Arg Arg Arg Asp Ala Phe Ala Phe Pro Gly Phe
```

```
    50                  55                  60

Ile Thr Gly Ile Ile Thr Phe Ile Met Val Phe His Phe Val Phe Thr
65                  70                  75                  80

Glu His Asn Ser Lys Tyr Ile Arg Phe Asn Lys Asn Leu His Asp Tyr
                85                  90                  95

Thr Leu Glu Tyr Lys Ala Gln Tyr Glu Asp Lys Thr Gln Arg Asp Lys
            100                 105                 110

Leu Pro Ser Phe Ile Leu Asp Lys Tyr Ala Pro Tyr Phe Asn Gln Glu
        115                 120                 125

Lys Leu Ser Ile Leu Asp Tyr Ile His Val Tyr Phe Gly Gly His Ile
    130                 135                 140

Thr Ser Lys Pro Tyr Gln Asn Thr Leu Phe Phe Leu Ser Thr Phe Ile
145                 150                 155                 160

Ala Pro Phe Phe Leu Ile Gly Leu Gly Gly Tyr Gln Ser Phe Phe Lys
                165                 170                 175

Lys Asn Pro Ile Leu Val Phe Asn Arg Glu Arg Asn Leu Val Tyr Thr
            180                 185                 190

Trp Arg Lys Asn Lys Val Phe Ile Ala Arg Tyr Pro Glu Ile Gly Ile
        195                 200                 205

Gly Lys Ile Gly Lys Thr Leu Thr Phe Gln Leu Phe Gly Leu Asp Lys
    210                 215                 220

Ser Lys Gln Thr Leu Val Ser Glu Leu Phe Phe Pro Asn Val Tyr Val
225                 230                 235                 240

Tyr Ser Val Tyr Asn Thr Ser Thr Asp Tyr His Asp Gln Arg Phe Ile
                245                 250                 255

Asn Phe Ile Asn Thr Tyr Met Arg Glu Gly Arg Asp Ala Ile Ile Pro
            260                 265                 270

Phe Asp Tyr His Arg Lys Lys Pro Lys Val Tyr Phe Gly Lys Asn Pro
        275                 280                 285

Pro Pro Ala Asp Phe Glu Gln Gln Val Glu Gln Ile Leu Ala Lys Leu
    290                 295                 300

Asp Gln Glu Lys Lys His His Ala
305                 310


<210> SEQ ID NO 9
<211> LENGTH: 315
<212> TYPE: DNA
<213> ORGANISM: Artificial Sequence
<220> FEATURE:
<223> OTHER INFORMATION: Synthetic Polynucleotide

<400> SEQUENCE: 9

gccgctcttg ccgctcgtga cgcattagaa gcttttcata ttggaaatta taaacaatct      60

gtatcaaata tagctattgt gattggttct ataattttaa ttactgctgt tactggagga     120

tgggctttat ttgctggggc acttattttg gggggattta tctcaagcca actcaccagt     180

tggagtcatt tagaaacttt actaaaacat agtttttggg ggaatgaaaa aaggtctaat     240

ttttgggata atgatagacc aacaccgata ggagaacaat taaaacaata tataaaagaa     300

tttgaattct ataaa                                                      315


<210> SEQ ID NO 10
<211> LENGTH: 105
<212> TYPE: PRT
<213> ORGANISM: Artificial Sequence
<220> FEATURE:
<223> OTHER INFORMATION: Synthetic Polypeptide
```

<400> SEQUENCE: 10

Ala Ala Leu Ala Ala Arg Asp Ala Leu Glu Ala Phe His Ile Gly Asn
1 5 10 15

Tyr Lys Gln Ser Val Ser Asn Ile Ala Ile Val Ile Gly Ser Ile Ile
20 25 30

Leu Ile Thr Ala Val Thr Gly Gly Trp Ala Leu Phe Ala Gly Ala Leu
35 40 45

Ile Leu Gly Gly Phe Ile Ser Ser Gln Leu Thr Ser Trp Ser His Leu
50 55 60

Glu Thr Leu Leu Lys His Ser Phe Trp Gly Asn Glu Lys Arg Ser Asn
65 70 75 80

Phe Trp Asp Asn Asp Arg Pro Thr Pro Ile Gly Glu Gln Leu Lys Gln
85 90 95

Tyr Ile Lys Glu Phe Glu Phe Tyr Lys
100 105

<210> SEQ ID NO 11
<211> LENGTH: 315
<212> TYPE: DNA
<213> ORGANISM: Artificial Sequence
<220> FEATURE:
<223> OTHER INFORMATION: Synthetic Polynucleotide

<400> SEQUENCE: 11
gttgctcttg ccactcgaga tgcattagaa gcttttcata ttggaaataa taaacaaggt 60
ttatcaaatg tagccattgc cattggttct ttcatgctaa tttttgttac agggggatgg 120
gctctatttg caggactgct aatattagga ggcttcttct caagtcaact caccagttgg 180
agtcatttgg aaactttgct aaggcacagt ttttggggaa atgaagaaag ttcaaatttt 240
tgggataata atagaccaac accgatagga gaacaattaa aacaatatat aaaagaattt 300
gaattctatg aacaa 315

<210> SEQ ID NO 12
<211> LENGTH: 105
<212> TYPE: PRT
<213> ORGANISM: Artificial Sequence
<220> FEATURE:
<223> OTHER INFORMATION: Synthetic Polypeptide

<400> SEQUENCE: 12

Val Ala Leu Ala Thr Arg Asp Ala Leu Glu Ala Phe His Ile Gly Asn
1 5 10 15

Asn Lys Gln Gly Leu Ser Asn Val Ala Ile Ala Ile Gly Ser Phe Met
20 25 30

Leu Ile Phe Val Thr Gly Gly Trp Ala Leu Phe Ala Gly Leu Leu Ile
35 40 45

Leu Gly Gly Phe Phe Ser Ser Gln Leu Thr Ser Trp Ser His Leu Glu
50 55 60

Thr Leu Leu Arg His Ser Phe Trp Gly Asn Glu Glu Ser Ser Asn Phe
65 70 75 80

Trp Asp Asn Asn Arg Pro Thr Pro Ile Gly Glu Gln Leu Lys Gln Tyr
85 90 95

Ile Lys Glu Phe Glu Phe Tyr Glu Gln
100 105

<210> SEQ ID NO 13

<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 13

```
acccottata ttgatacttc cattttgtct accctactca tttcattagt ttatttaatt    60

gtagtatct                                                            69
```

<210> SEQ ID NO 14
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 14

```
Thr Pro Tyr Ile Asp Thr Ser Ile Leu Ser Thr Leu Leu Ile Ser Leu
1               5                   10                  15

Val Tyr Leu Ile Val Val Ser
            20
```

<210> SEQ ID NO 15
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 15

```
aaaccctatc aaaatacgct attttttctt tctactttca tcgcaccttt cttcttaatt    60

ggcttgggt                                                            69
```

<210> SEQ ID NO 16
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 16

```
Lys Pro Tyr Gln Asn Thr Leu Phe Phe Leu Ser Thr Phe Ile Ala Pro
1               5                   10                  15

Phe Phe Leu Ile Gly Leu Gly
            20
```

<210> SEQ ID NO 17
<211> LENGTH: 390
<212> TYPE: DNA
<213> ORGANISM: Artificial Sequence
<220> FEATURE:
<223> OTHER INFORMATION: Synthetic Polynucleotide

<400> SEQUENCE: 17

```
gcgaacaatt aaaaatggca agtgaaaaag gtgattggaa ccctgaaaca ggtatattta    60

aatttagttt ggaagtacag tctcaattag taaatacata ttctgctttt ggtgcacatc   120

ctaatagccg tataggtatt gaagatttat attggtatta tcaagtcaat cccgaggtaa   180

caacaccgat gcgttatatc aattgggggg gagataccca agaaaacaat cagcttttag   240

gctttattaa cagtgagaat atctaaatca ggagaaagaa caccatgcgt agtttggtaa   300

acggcagaaa gattatttta gaaaatgata caacaaatac cggcggtacc gtacttaccg   360
```

-continued

```
gctcttctat tgctaaacaa acacaagggg                              390


<210> SEQ ID NO 18
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 18

cgcgggcccg gtattacccc ataaatagtg c                             31


<210> SEQ ID NO 19
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 19

cagctatatt tggtttaact taaggtctag agcgcgc                       37
```